United States Patent
Brown

(10) Patent No.: US 9,901,563 B2
(45) Date of Patent: Feb. 27, 2018

(54) COMPOSITIONS TO IMPROVE THE THERAPEUTIC BENEFIT OF SUBOPTIMALLY ADMINISTERED CHEMICAL COMPOUNDS INCLUDING SUBSTITUTED HEXITOLS SUCH AS DIANHYDROGALACTITOL AND DIACETYLDIANHYDROGALACTITOL

(71) Applicant: DELMAR PHARMACEUTICALS, INC., Vancouver (CA)

(72) Inventor: Dennis M. Brown, Menlo Park, CA (US)

(73) Assignee: DELMAR PHARMACEUTICALS, INC., Vancouver (CA)

( * ) Notice: Subject to any disclaimer, the term of this patent is extended or adjusted under 35 U.S.C. 154(b) by 0 days.

(21) Appl. No.: 14/753,911

(22) Filed: Jun. 29, 2015

(65) Prior Publication Data
US 2015/0297553 A1    Oct. 22, 2015

Related U.S. Application Data

(63) Continuation-in-part of application No. 13/817,096, filed on Mar. 11, 2013, now Pat. No. 9,066,918.

(51) Int. Cl.
| | | |
|---|---|---|
| *A61K 31/045* | (2006.01) | |
| *A61K 31/336* | (2006.01) | |
| *A61K 33/24* | (2006.01) | |
| *A61K 45/06* | (2006.01) | |
| *A61K 31/4741* | (2006.01) | |
| *A61K 31/353* | (2006.01) | |
| *A61K 31/513* | (2006.01) | |
| *C07D 303/14* | (2006.01) | |
| *A61K 31/7088* | (2006.01) | |
| *A61K 38/19* | (2006.01) | |
| *A61K 31/12* | (2006.01) | |
| *A61K 31/155* | (2006.01) | |
| *A61K 31/216* | (2006.01) | |
| *A61K 31/352* | (2006.01) | |
| *A61K 31/4745* | (2006.01) | |
| *A61K 31/475* | (2006.01) | |
| *A61K 31/713* | (2006.01) | |
| *A61K 9/00* | (2006.01) | |
| *A61K 31/45* | (2006.01) | |

(52) U.S. Cl.
CPC .......... *A61K 31/336* (2013.01); *A61K 9/0019* (2013.01); *A61K 31/12* (2013.01); *A61K 31/155* (2013.01); *A61K 31/216* (2013.01); *A61K 31/352* (2013.01); *A61K 31/353* (2013.01); *A61K 31/475* (2013.01); *A61K 31/4741* (2013.01); *A61K 31/4745* (2013.01); *A61K 31/513* (2013.01); *A61K 31/7088* (2013.01); *A61K 31/713* (2013.01); *A61K 33/24* (2013.01); *A61K 38/19* (2013.01); *A61K 45/06* (2013.01); *C07D 303/14* (2013.01); *A61K 31/45* (2013.01)

(58) Field of Classification Search
CPC ... A61K 31/047; A61K 31/045; A61K 31/165
USPC ........................................................ 514/724
See application file for complete search history.

(56) References Cited

U.S. PATENT DOCUMENTS 6,180,824 B1    1/2001  Stamler et al.

FOREIGN PATENT DOCUMENTS

| GB | 1490649 A | 11/1977 | |
|---|---|---|---|
| WO | WO 0191741 A2 * | 12/2001 | ............. A61K 31/70 |
| WO | 2009053713 A2 | 4/2009 | |
| WO | WO 2012024367 A2 * | 2/2012 | ............. A61K 31/44 |

OTHER PUBLICATIONS

Chinese Office Action for related Chinese Patent Application No. 201180050169.2 dated Oct. 27, 2015, 9 Pages.
Zhao, "New Drugs and Clinical Evaluation", Tianjin Science and Technology Publisher, Jun. 2013, 4 Pages.
Xiao et al., "The Stability Research of DADAG", Journal of Medical Reviews, Dec. 2002, vol. 19, Chapter 6, 2 Pages.
Yang et al., "Antitumor Effect of Diacetyldianhydrogalactitol and Its Mechanism", Chinese Journal of Cancer, 2000, Issue 12, pp. 1112-1115.
Sternson et al., "Chemical Derivatization as a Strategy to Enhance Detectability of Agents Used in Cancer Management," Published in Journal of Pharmaceutical & Biomedical Analysis, vol. 6, (1988) pp. 657-668.
Järvinen et al., "Design and Pharmaceutical Applications of Prodrugs", published in Drug Discovery Handbook (S.C. Gad, ed., Wiley-Interscience, Hoboken, NJ, 2005), ch. 17, pp. 733-796.
Rowe et al., "Handbook of Pharmaceutical Excipients", published in Pharmaceutical Press & American Pharmacists Association, 5th edition, 2006, London, 3 pages.
Plenderleith, "Treating the Treatment: Toxicity of Cancer Therapy", published in Can Fam Physician vol. 36: 1827-1830, Oct. 1990, pp. 1827-1830, 4 pages.

(Continued)

*Primary Examiner* — Kevin E Weddington
(74) *Attorney, Agent, or Firm* — Ditthavong & Steiner, P.C.

(57) ABSTRACT

The present invention describes methods and compositions for improving the therapeutic efficacy of therapeutic agents previously limited by suboptimal therapeutic performance by either improving efficacy as monotherapy or reducing side effects. Such methods and compositions are particularly applicable to substituted hexitols such as dianhydrogalactitol and diacetyldianhydrogalactitol.

10 Claims, No Drawings

(56) References Cited

OTHER PUBLICATIONS

Han et al., "Targeted Prodrug Design to Optimize Drug Delivery", published in AAPS PharmSciTech 2 (Article 6), Mar. 21, 2000, pp. 1-11.
Brittain, "Developing an Appropriate Salt Form for an Active Pharmaceutical Ingredient", published in American Pharmaceutical Review, Dec. 1, 2009, retrieved on Dec. 19, 2017 from http://www.americanpharmaceuticalreview.com/Featured-Articles/117788-Developing-an-Appropriate-Salt-Form-for-an-Active-Pharmaceutical-Ingredient/, 5 pages.

* cited by examiner

COMPOSITIONS TO IMPROVE THE THERAPEUTIC BENEFIT OF SUBOPTIMALLY ADMINISTERED CHEMICAL COMPOUNDS INCLUDING SUBSTITUTED HEXITOLS SUCH AS DIANHYDROGALACTITOL AND DIACETYLDIANHYDROGALACTITOL

CROSS-REFERENCES TO RELATED APPLICATIONS

This application is a continuation-in-part application and claims the benefit of U.S. patent application Ser. No. 13/817,096 by Dennis M. Brown, Ph.D., filed Feb. 14, 2013, and entitled "Compositions and Methods to Improve the Therapeutic Benefit of Suboptimally Administered Chemical Compounds Including Substituted Hexitols Such as Dianhydrogalactitol and Diacetyldianhydrogalactitol," which in turn was a national stage and claimed the benefit of PCT Patent Application Ser. No. PCT/US2011/048031 by Dennis M. Brown, Ph.D., filed Aug. 7, 2011, which in turn claimed the benefit of: (1) U.S. Provisional Application Ser. No. 61/401,705 by Dennis M. Brown, Ph.D., filed Aug. 18, 2010, and entitled "Compositions and Methods to Improve the Therapeutic Benefit of Suboptimally Administered Chemical Compounds Including Substituted Hexitols Such as Dianhydrogalactitol for the Treatment of Benign and Neoplastic Hyperproliferative Disease Conditions"; (2) U.S. Provisional Application Ser. No. 61/401,706 by Dennis M. Brown, Ph.D., filed Aug. 18, 2010, and entitled "Compositions and Methods to Improve the Therapeutic Benefit of Suboptimally Administered Chemical Compounds Including Substituted Hexitols Such as Diacetyldianhydrogalactitol for the Treatment of Benign and Neoplastic Hyperproliferative Disease Conditions"; (3) U.S. Provisional Application Ser. No. 61/401,707 by Dennis M. Brown, Ph.D., filed Aug. 18, 2010, and entitled "Compositions and Methods to Improve the Therapeutic Benefit of Suboptimally Administered Chemical Compounds Including Substituted Hexitols Such as Diacetyldianhydrogalactitol for the Condition of Benign and Neoplastic Hyperproliferative Conditions"; (4) U.S. Provisional Application Ser. No. 61/401,709 by Dennis M. Brown, Ph.D., filed Aug. 18, 2010, and entitled "Compositions and Methods to Improve the Therapeutic Benefit of Suboptimally Administered Chemical Compounds Including Substituted Hexitols Such as Diacetyldianhydrogalactitol for the Condition of Benign and Neoplastic Hyperproliferative Conditions"; and (5) U.S. Provisional Application Ser. No. 61/401,712 by Dennis M. Brown, Ph.D., filed Aug. 18, 2010, and entitled "Compositions and Methods to Improve the Therapeutic Benefit of Suboptimally Administered Chemical Compounds Including Substituted Hexitols Such as Diacetyldianhydrogalactitol for the Condition of Benign and Neoplastic Hyperproliferative Conditions." All the above-mentioned applications are incorporated herein in their entirety by this reference.

FIELD OF THE INVENTION

The present invention relates to the general field of hyperproliferative diseases including oncology with a focus on novel methods and compositions for the improved utility of chemical agents, compounds, and dosage forms previously limited by suboptimal human therapeutic performance including substituted hexitols such as dianhydrogalactitol and diacetyldianhydrogalactitol, as well as other classes of chemical agents.

BACKGROUND OF THE INVENTION

The search for and identification of cures for many life-threatening diseases that plague humans still remains an empirical and sometimes serendipitous process. While many advances have been made from basic scientific research to improvements in practical patient management, there still remains tremendous frustration in the rational and successful discovery of useful therapies particularly for life-threatening diseases such as cancer, inflammatory conditions, infection, and other conditions.

Since the "War on Cancer" began in the early 1970's by the United States National Cancer Institute (NCI) of the National Institutes of Health (NIH), a wide variety of strategies and programs have been created and implemented to prevent, diagnose, treat and cure cancer. One of the oldest and arguably most successful programs has been the synthesis and screening of small chemical entities (<1500 MW) for biological activity against cancer. This program was organized to improve and streamline the progression of events from chemical synthesis and biological screening to preclinical studies for the logical progression into human clinical trials with the hope of finding cures for the many types of life-threatening malignant tumors. The synthesis and screening of hundreds of thousands of chemical compounds from academic and industrial sources, in addition to the screening of natural products and extracts from prokaryotes, invertebrate animals, plant collections, and other sources from all over the world has been and continues to be a major approach for the identification of novel lead structures as potential new and useful medicines. This is in addition to other programs including biotherapeutics designed to stimulate the human immune system with vaccines, therapeutic antibodies, cytokines, lymphokines, inhibitors of tumor blood vessel development (angiogenesis) or gene and antisense therapies to alter the genetic make-up of cancer cells, and other biological response modifiers.

The work supported by the NCI, other governmental agencies both domestic and foreign in academic or industrial research and development laboratories has resulted in an extraordinary body of biological, chemical and clinical information. In addition, large chemical libraries have been created, as well as highly characterized in vitro and in vivo biological screening systems that have been successfully used. However, from the tens of billions of dollars spent over the past thirty years supporting these programs both preclinically and clinically, only a small number of compounds have been identified or discovered that have resulted in the successful development of useful therapeutic products. Nevertheless, the biological systems both in vitro and in vivo and the "decision trees" used to warrant further animal studies leading to clinical studies have been validated. These programs, biological models, clinical trial protocols, and other information developed by this work remain critical for the discovery and development of any new therapeutic agent.

Unfortunately, many of the compounds that have successfully met the preclinical testing and federal regulatory requirements for clinical evaluation were either unsuccessful or disappointing in human clinical trials. Many compounds were found to have untoward or idiosyncratic side-effects that were discovered during human clinical Phase I dose-escalation studies used to determine the maximum tolerated dose (MTD) and side-effect profile. In some cases, these toxicities or the magnitude of their toxicity were not identified or predicted in preclinical toxicology studies. In other cases, chemical agents where in vitro and in vivo studies suggested a potentially unique activity against a particular tumor type, molecular target or biological pathway were not successful in human Phase II clinical trials where specific examination of particular cancer indications/types were evaluated in government sanctioned (e.g., U.S. FDA), IRB approved clinical trials. In addition, there are those cases where potential new agents were evaluated in randomized Phase III clinical trials where a significant clinical benefit could not be demonstrated; such cases have also been the cause of great frustration and disappointment. Finally, a number of compounds have reached commercialization but their ultimate clinical utility has been limited by poor efficacy as monotherapy (<25% response rates) and untoward dose-limiting side-effects (Grade III and IV) (e.g., myelosuppression, neurotoxicity, cardiotoxicity, gastrointestinal toxicities, or other significant side effects).

In many cases, after the great time and expense of developing and moving an investigational compound into human clinical trials and where clinical failure has occurred, the tendency has been to return to the laboratory to create a better analog, look for agents with different structures but potentially related mechanisms of action, or try other modifications of the drug. In some cases, efforts have been made to try additional Phase I or II clinical trials in an attempt to make some improvement with the side-effect profile or therapeutic effect in selected patients or cancer indications. In many of those cases, the results did not realize a significant enough improvement to warrant further clinical development toward product registration. Even for commercialized products, their ultimate use is still limited by suboptimal performance.

With so few therapeutics approved for cancer patients and the realization that cancer is a collection of diseases with a multitude of etiologies and that a patient's response and survival from therapeutic intervention is complex with many factors playing a role in the success or failure of treatment including disease indication, stage of invasion and metastatic spread, patient gender, age, health conditions, previous therapies or other illnesses, genetic markers that can either promote or retard therapeutic efficacy, and other factors, the opportunity for cures in the near term remains elusive. Moreover, the incidence of cancer continues to rise with an approximate 4% increase predicted for 2003 in the United States by the American Cancer Society such that over 1.3 million new cancer cases are estimated. In addition, with advances in diagnosis such as mammography for breast cancer and PSA tests for prostate cancer, more patients are being diagnosed at a younger age. For difficult to treat cancers, a patient's treatment options are often exhausted quickly resulting in a desperate need for additional treatment regimens. Even for the most limited of patient populations, any additional treatment opportunities would be of considerable value. This invention focuses on inventive compositions and methods for improving the therapeutic benefit of suboptimally administered chemical compounds including substituted hexitols such as dianhydrogalactitol.

Relevant literature includes Foye, W. O., "Cancer Chemotherapeutic Agents," American Chemical Society, 1995, and Dorr, R. T., and Von Hoff, D. D., "Cancer Chemotherapy Handbook," Appleton and Lange, 1994.

Therefore, there is a need for compositions and methods that improve the therapeutic benefit of suboptimally administered chemical compounds and therapeutic compositions.

SUMMARY OF THE INVENTION

This invention meets the needs described above for compositions and methods that improve the therapeutic benefit of suboptimally administered chemical compounds and therapeutic compositions. Specifically, this invention relates to novel compositions and methods to improve the utility of chemical agents with suboptimal performance in patients suffering with cancer. The invention describes novel improvements, pharmaceutical ingredients, dosage forms, excipients, solvents, diluents, drug delivery systems, preservatives, more accurate drug administrations, improved dose determination and schedules, toxicity monitoring and amelioration, techniques or agents to circumvent or reduce toxicity, techniques and tools to identify/predict those patients who might have a better outcome with a therapeutic agent by the use of phenotype or genotype determination through the use of diagnostic kits or pharmacokinetic or metabolism monitoring approaches. The invention also relates to the use of drug delivery systems, novel prodrugs, polymer conjugates, novel routes of administration, other agents to potentiate the activity of the compounds or inhibit the repair of suboptimal cellular effects or sublethal damage or to "push" the cell into more destructive cellular phases such as apoptosis. In some case, the use of these suboptimal therapeutics in conjunction with radiation or other conventional chemotherapeutic agents or biotherapeutic agents such as antibodies, vaccines, cytokines, lymphokines, gene and antisense therapies, or other chemotherapeutic or biotherapeutic agents, would provide novel approaches and significant improvement.

In the inventive compositions and methods, the term suboptimal therapy includes agents where Phase I toxicity precluded further human clinical evaluation. It also includes those agents from Phase II trials where limited (<25% response rates) or no significant tumor responses were identified. Also, suboptimal therapy includes those agents, the subject of Phase III clinical trials the outcome of which was either medically or statistically not significant to warrant regulatory submission or approval by government agencies for commercialization or commercialized agents whose clinical performance (i.e. response rates) as a monotherapy are less than 25%, or whose side-effects are severe enough to limit wide utility. Agents with suboptimal clinical activity include but are not limited to the following: substituted hexitols such as dianhydrogalactitol and diacetyldianhydrogalactitol, Avastin (bevacizumab), Rituxan (rituximab), Nexavar (sorafenib), dasatinib, nilotinib, Provenge (sipuleucel-T), Tarceva (erlotinib), and Iressa (gefitinib). More specifically, the inventive methods and compositions also focus on improvements for substituted hexitols including dianhydrogalactitol and diacetyldianhydrogalactitol.

One aspect of the invention is a method to improve the efficacy and/or reduce the side effects of suboptimally administered drug therapy comprising the steps of:

(i) identifying at least one factor or parameter associated with the efficacy and/or occurrence of side effects of the drug therapy; and (ii) modifying the factor or parameter to improve the efficacy and/or reduce the side effects of the drug therapy.

In this method, the factor or parameter can be selected from the group consisting of:

(i) dose modification;
(ii) route of administration;
(iii) schedule of administration;
(iv) indications for use;
(v) selection of disease stage;

(vi) other indications;
(vii) patient selection;
(viii) patient/disease phenotype;
(ix) patient/disease genotype;
(x) pre/post-treatment preparation
(xi) toxicity management;
(xii) pharmacokinetic/pharmacodynamic monitoring;
(xiii) drug combinations;
(xiv) chemosensitization;
(xv) chemopotentiation;
(xvi) post-treatment patient management;
(xvii) alternative medicine/therapeutic support;
(xviii) bulk drug product improvements;
(xix) diluent systems;
(xx) solvent systems;
(xxi) excipients;
(xxii) dosage forms;
(xxiii) dosage kits and packaging;
(xxiv) drug delivery systems;
(xxv) drug conjugate forms;
(xxvi) compound analogs;
(xxvii) prodrugs;
(xxvii) multiple drug systems;
(xxviii) biotherapeutic enhancement;
(xxix) biotherapeutic resistance modulation;
(xxx) radiation therapy enhancement;
(xxxi) novel mechanisms of action; and
(xxxii) selective target cell population therapeutics.

The drug therapy can be administered to treat a hyperproliferative disease, such as cancer.

Typically, the suboptimally administered drug therapy comprises administration of a substituted hexitol. In one alternative, preferably, the substituted hexitol is selected from the group consisting of dianhydrogalactitol and a derivative thereof. In this alternative, more preferably, the substituted hexitol is dianhydrogalactitol. In another alternative, preferably, the substituted hexitol is selected from the group consisting of diacetyldianhydrogalactitol and a derivative thereof. In this alternative, more preferably, the substituted hexitol is diacetyldianhydrogalactitol.

In yet another alternative, the suboptimally administered drug therapy comprises administration of a therapeutic agent selected from the group consisting of Avastin (bevacizumab), Rituxan (rituximab), Nexavar (sorafenib), dasatinib, nilotinib, Provenge (sipuleucel-T), Tarceva (erlotinib), and Iressa (gefitinib).

The following alternatives describe the use of dianhydrogalactitol, diacetyldianhydrogalactitol, or, in some cases as set forth below, a derivative of either dianhydrogalactitol or diacetyldianhydrogalactitol, together with a modification of a factor or parameter as described above to improve the efficacy and/or reduce the side effects of the drug therapy.

When the improvement is made by dose modification, the dose modification can be a modification selected from the group consisting of:
(a) continuous i.v. infusion for hours to days;
(b) biweekly administration;
(c) doses greater than 5 mg/m$^2$/day;
(d) progressive escalation of dosing from 1 mg/m$^2$/day based on patient tolerance;
(e) use of caffeine to modulate metabolism;
(f) use of isonazid to modulate metabolism;
(g) selected and intermittent boosting of dosage administration;
(h) administration of single and multiple doses escalating from 5 mg/m$^2$/day via bolus;
(i) oral dosages of below 30 mg/m$^2$; and
(j) oral dosages of above 130 mg/m$^2$.

When the improvement is made by the route of administration, the route of administration can be a route of administration selected from the group consisting of:
(a) topical administration;
(b) intravesicular administration for bladder cancer;
(c) oral administration;
(d) slow release oral delivery;
(e) intrathecal administration;
(f) intraarterial administration;
(g) continuous infusion; and
(h) intermittent infusion.

When the improvement is made by the schedule of administration, the schedule of administration can be a schedule of administration selected from the group consisting of:
(a) daily administration;
(b) weekly administration;
(c) weekly administration for three weeks;
(d) biweekly administration;
(e) biweekly administration for three weeks with a 1-2 week rest period;
(f) intermittent boost dose administration; and
(g) daily administration for one week for multiple weeks.

When the improvement is made by the indication for use, the indication for use can be an indication for use selected from the group consisting of:
(a) use for treatment of leukemias;
(b) use for treatment of myelodysplastic syndrome;
(c) use for treatment of angiogenic diseases;
(d) use for treatment of benign prostatic hyperplasia;
(e) use for treatment of psoriasis;
(f) use for treatment of gout;
(g) use for treatment of transplantation rejections;
(h) use for prevention of restenosis in cardiovascular disease;
(i) use for treatment of mycosis fungoides;
(j) use in bone marrow transplantation;
(k) use as an anti-infective agent;
(l) use for treatment of AIDS; and
(m) use for treatment of lymphoma.

When the improvement is made by selection of disease stage, the selection of disease stage can be selected from the group consisting of:
(a) use for the treatment of localized polyp stage colon cancer;
(b) use for leukoplakia in the oral cavity;
(c) use for angiogenesis inhibition to prevent or limit metastatic spread of a malignancy; and
(d) use for treatment of HIV with a therapy selected from the group consisting of azidothymidine (AZT), dideoxyadenosine (DDI), and reverse transcriptase inhibitors.

When the improvement is made by other indications, the other indications can be selected from the group consisting of:
(a) use as an anti-infective agent;
(b) use as an antiviral agent;
(c) use as an antibacterial agent;
(d) use as an agent to treat pleural effusion;
(e) use as an antifungal agent;
(f) use as an anti-parasitic agent;
(g) use as an agent to treat eczema;
(h) use as an agent to treat herpes zoster (shingles);

(i) use as an agent to treat condylomata;
(j) use as an agent to treat HPV; and
(k) use as an agent to treat HSV.

When the improvement is made by patient selection, the patient selection can be carried out by a criterion selected from the group consisting of:
  (a) selecting patients with a disease condition characterized by a high level of a metabolic enzyme selected from the group consisting of histone deacetylase and ornithine decarboxylase;
  (b) selecting patients with a low or high susceptibility to a condition selected from the group consisting of thrombocytopenia and neutropenia;
  (c) selecting patients intolerant of GI toxicities; and
  (d) selecting patients characterized by over- or under-expression of a gene selected from the group consisting of c-Jun, a GPCR, a signal transduction protein, VEGF, a prostate-specific gene, and a protein kinase.

Where the improvement is made by analysis of patient or disease phenotype, the analysis of patient or disease phenotype can be carried out by a method selected from the group consisting of:
  (i) use of a diagnostic tool, a diagnostic technique, a diagnostic kit, or a diagnostic assay to confirm a patient's particular phenotype;
  (ii) use of a method for measurement of a marker selected from the group consisting of histone deacetylase, ornithine decarboxylase, VEGF, a protein that is a gene product of a prostate specific gene, a protein that is a gene product of jun, a protein kinase, quantity or activity of MGMT, methylation of MGMT promoter, and mutant isocitrate dehydrogenase (IDH);
  (iii) surrogate compound dosing; and
  (iv) low dose pre-testing for enzymatic status.

When the improvement is made by analysis of patient or disease genotype, the analysis of patient or disease genotype can be carried out by a method selected from the group consisting of:
  (a) use of a diagnostic tool, a diagnostic technique, a diagnostic kit, or a diagnostic assay to confirm a patient's particular genotype;
  (b) use of a gene chip;
  (c) use of gene expression analysis;
  (d) use of single nucleotide polymorphism (SNP) analysis; and
  (e) measurement of the level of a metabolite or a metabolic enzyme.

When the improvement is made by pre/post treatment preparation, the pre/post treatment preparation can be selected from the group consisting of:
  (a) the use of colchicine or an analog thereof;
  (b) the use of a uricosuric;
  (c) the use of uricase;
  (d) the non-oral use of nicotinamide;
  (e) the use of a sustained-release form of nicotinamide;
  (f) the use of an inhibitor of poly-ADP ribose polymerase;
  (g) the use of caffeine;
  (h) the use of leucovorin rescue;
  (i) infection control; and
  (j) the use of an anti-hypertensive agent.

When the improvement is made by toxicity management, the toxicity management can be selected from the group consisting of:
  (a) the use of colchicine or an analog thereof;
  (b) the use of a uricosuric;
  (c) the use of uricase;
  (d) the non-oral use of nicotinamide;
  (e) the use of a sustained-release form of nicotinamide;
  (f) the use of an inhibitor of poly-ADP ribose polymerase;
  (g) the use of caffeine;
  (h) the use of leucovorin rescue;
  (i) the use of sustained-release allopurinol;
  (j) the non-oral use of allopurinol;
  (k) the use of bone marrow transplants;
  (l) the use of a blood cell stimulant;
  (m) the use of blood or platelet infusions;
  (n) the administration of an agent selected from the group consisting of filgrastim (Neupogen®), G-CSF, and GM-CSF;
  (o) the application of a pain management technique;
  (p) the administration of an anti-inflammatory agent;
  (q) the administration of fluids;
  (r) the administration of a corticosteroid;
  (s) the administration of an insulin control medication;
  (t) the administration of an antipyretic;
  (u) the administration of an anti-nausea treatment;
  (v) the administration of an anti-diarrheal treatment;
  (w) the administration of N-acetylcysteine; and
  (x) the administration of an antihistamine.

When the improvement is made by pharmacokinetic/pharmacodynamic monitoring, the pharmacokinetic/pharmacodynamic monitoring can be performed by a method selected from the group consisting of:
  (a) multiple determinations of blood plasma levels; and
  (b) multiple determinations of at least one metabolite in blood or urine.

When the improvement is made by drug combination, the drug combination can be selected from the group consisting of:
  (a) use with topoisomerase inhibitors;
  (b) use with fraudulent nucleosides;
  (c) use with fraudulent nucleotides;
  (d) use with thymidylate synthetase inhibitors;
  (e) use with signal transduction inhibitors;
  (f) use with cisplatin or platinum analogs;
  (g) use with alkylating agents;
  (h) use with anti-tubulin agents;
  (i) use with antimetabolites;
  (j) use with berberine;
  (k) use with apigenin;
  (l) use with amonafide;
  (m) use with vinca alkaloids;
  (n) use with 5-fluorouracil;
  (o) use with curcumin;
  (p) use with NF-κB inhibitors;
  (q) use with rosmarinic acid;
  (r) use with mitoguazone;
  (s) use with tetrandrine;
  (t) use with an inhibitor of mutant isocitrate dehydrogenase (IDH);
  (u) use with a MGMT inhibitor; and
  (v) use with an agent that inhibits NF-κB-enhanced expression of MGMT.

When the improvement is made by chemosensitization, the chemosensitization can comprise the use of dianhydrogalactitol as a chemosensitizer in combination with an agent selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin or platinum analogs;
  (g) alkylating agents;

(h) anti-tubulin agents;
(i) antimetabolites;
(j) berberine;
(k) apigenin;
(l) amonafide;
(m) vinca alkaloids;
(n) 5-fluorouracil;
(o) curcumin;
(p) NF-κB inhibitors;
(q) rosmarinic acid;
(r) mitoguazone; and
(s) tetrandrine.

When the improvement is made by chemopotentiation, the chemopotentiation can comprise the use of dianhydrogalactitol as a chemopotentiator in combination with an agent selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) vinca alkaloids;
(n) 5-fluorouracil;
(o) curcumin;
(p) NF-κB inhibitors;
(q) rosmarinic acid;
(r) mitoguazone; and
(s) tetrandrine.

When the improvement is made by post-treatment management, the post-treatment management can be selected from the group consisting of:
(a) a therapy associated with pain management;
(b) administration of an anti-emetic;
(c) an anti-nausea therapy;
(d) administration of an anti-inflammatory agent;
(e) administration of an anti-pyretic agent; and
(f) administration of an immune stimulant.

When the improvement is made by alternative medicine/therapeutic support, the alternative medicine/therapeutic support can be selected from the group consisting of:
(a) hypnosis;
(b) acupuncture;
(c) meditation;
(d) a herbal medication created either synthetically or through extraction; and
(e) applied kinesiology.

When the improvement is made by a bulk drug product improvement, the bulk drug product improvement can be selected from the group consisting of:
(a) salt formation;
(b) preparation as a homogeneous crystal structure;
(c) preparation as a pure isomer;
(d) increased purity;
(e) preparation with lower residual solvent content; and
(f) preparation with lower residual heavy metal content.

When the improvement is made by use of a diluent, the diluent can be selected from the group consisting of:
(a) an emulsion;
(b) dimethylsulfoxide (DMSO);
(c) N-methylformamide (NMF);
(d) DMF;
(e) ethanol;
(f) benzyl alcohol;
(g) dextrose-containing water for injection;
(h) Cremophor;
(i) cyclodextrin; and
(j) PEG.

When the improvement is made by a solvent system, the solvent system can be selected from the group consisting of:
(a) an emulsion;
(b) dimethylsulfoxide (DMSO);
(c) N-methylformamide (NMF);
(d) DMF;
(e) ethanol;
(f) benzyl alcohol;
(g) dextrose-containing water for injection;
(h) Cremophor;
(i) cyclodextrin; and
(j) PEG.

When the improvement is made by use of an excipient, the excipient can be selected from the group consisting of:
(a) mannitol;
(b) albumin;
(c) EDTA;
(d) sodium bisulfite;
(e) benzyl alcohol;
(f) a carbonate buffer; and
(g) a phosphate buffer.

When the improvement is made by use of a dosage form, the dosage form can be selected from the group consisting of:
(a) tablets;
(b) capsules;
(c) topical gels;
(d) topical creams;
(e) patches;
(f) suppositories; and
(g) lyophilized dosage fills.

When the improvement is made by use of dosage kits and packaging, the dosage kits and packaging can be selected from the group consisting of the use of amber vials to protect from light and the use of stoppers with specialized coatings to improve shelf-life stability.

When the improvement is made by use of a drug delivery system, the drug delivery system can be selected from the group consisting of:
(a) nanocrystals;
(b) bioerodible polymers;
(c) liposomes;
(d) slow release injectable gels; and
(e) microspheres.

When the improvement is made by use of a drug conjugate form, the drug conjugate form can be selected from the group consisting of:
(a) a polymer system;
(b) polylactides;
(c) polyglycolides;
(d) amino acids;
(e) peptides; and
(f) multivalent linkers.

When the improvement is made by use of a compound analog, the compound analog can be selected from the group consisting of:
(a) alteration of side chains to increase or decrease lipophilicity;

(b) addition of an additional chemical functionality to alter a property selected from the group consisting of reactivity, electron affinity, and binding capacity; and
(c) alteration of salt form.

When the improvement is made by use of a prodrug system, the prodrug can be selected from the group consisting of:
(a) the use of enzyme sensitive esters;
(b) the use of dimers;
(c) the use of Schiff bases;
(d) the use of pyridoxal complexes; and
(e) the use of caffeine complexes.

When the improvement is made by use of a multiple drug system, the multiple drug system can employ a mechanism selected from the group consisting of:
(a) use of multi-drug resistance inhibitors;
(b) use of specific drug resistance inhibitors;
(c) use of specific inhibitors of selective enzymes;
(d) use of signal transduction inhibitors;
(e) use of repair inhibition; and
(f) use of topoisomerase inhibitors with non-overlapping side effects.

When the improvement is made by use of biotherapeutic enhancement, the biotherapeutic enhancement can be performed by use in combination as sensitizers/potentiators with a therapeutic agent or technique selected from the group consisting of:
(a) cytokines;
(b) lymphokines;
(c) therapeutic antibodies;
(d) antisense therapies;
(e) gene therapies;
(f) ribozymes; and
(g) RNA interference.

When the improvement is made by use of biotherapeutic resistance modulation, the biotherapeutic resistance modulation can comprise use against tumors resistant to a therapeutic agent or technique selected from the group consisting of:
(a) biological response modifiers;
(b) cytokines;
(c) lymphokines;
(d) therapeutic antibodies;
(e) antisense therapies;
(f) gene therapies;
(g) ribozymes; and
(h) RNA interference.

When the improvement is made by use of radiation therapy enhancement, the radiation therapy enhancement can be performed by use of an agent or technique selected from the group consisting of:
(a) hypoxic cell sensitizers;
(b) radiation sensitizers/protectors;
(c) photosensitizers;
(d) radiation repair inhibitors;
(e) thiol depleters;
(f) vaso-targeted agents;
(g) DNA repair inhibitors;
(h) radioactive seeds;
(i) radionuclides;
(j) radiolabeled antibodies; and
(k) brachytherapy.

When the improvement is made by use of novel mechanisms of action, the novel mechanism of action can be a therapeutic interaction with a target or mechanism selected from the group consisting of:
(a) inhibitors of poly-ADP ribose polymerase;
(b) agents that affect vasculature or vasodilation;
(c) oncogenic targeted agents;
(d) signal transduction inhibitors;
(e) EGFR inhibition;
(f) protein kinase C inhibition;
(g) phospholipase C downregulation;
(h) Jun downregulation;
(i) histone genes;
(j) VEGF;
(k) ornithine decarboxylase;
(l) ubiquitin C;
(m) jun D;
(n) v-jun;
(o) GPCRs;
(p) protein kinase A;
(q) protein kinases other than protein kinase A;
(r) prostate specific genes;
(s) telomerase; and
(t) histone deacetylase.

When the improvement is made by use of selective target cell population therapeutics, the use of selective target cell population therapeutics can be a use selected from the group consisting of:
(a) use against radiation sensitive cells;
(b) use against radiation resistant cells;
(c) use against energy depleted cells; and
(d) use against endothelial cells.

Another aspect of the present invention is a composition to improve the efficacy and/or reduce the side effects of suboptimally administered drug therapy comprising an alternative selected from the group consisting of:
(i) a therapeutically effective quantity of a modified therapeutic agent or a derivative, analog, or prodrug of a therapeutic agent or modified therapeutic agent, wherein the modified therapeutic agent or the derivative, analog or prodrug of the therapeutic agent or modified therapeutic agent possesses increased therapeutic efficacy or reduced side effects as compared with an unmodified therapeutic agent;
(ii) a composition comprising:
(a) a therapeutically effective quantity of a therapeutic agent, a modified therapeutic agent or a derivative, analog, or prodrug of a therapeutic agent or modified therapeutic agent; and
(b) at least one additional therapeutic agent, therapeutic agent subject to chemosensitization, therapeutic agent subject to chemopotentiation, diluent, excipient, solvent system, or drug delivery system, wherein the composition possesses increased therapeutic efficacy or reduced side effects as compared with an unmodified therapeutic agent;
(iii) a therapeutically effective quantity of a therapeutic agent, a modified therapeutic agent, or a derivative, analog, or prodrug of a therapeutic agent or modified therapeutic agent that is incorporated into a dosage form, wherein the therapeutic agent, the modified therapeutic agent, or the derivative, analog, or prodrug of a therapeutic agent or modified therapeutic agent incorporated into the dosage form possesses increased therapeutic efficacy or reduced side effects as compared with an unmodified therapeutic agent;
(iv) a therapeutically effective quantity of a therapeutic agent, a modified therapeutic agent, or a derivative, analog, or prodrug of a therapeutic agent or modified therapeutic agent that is incorporated into a dosage kit and packaging, wherein the therapeutic agent, the modified therapeutic agent, or the derivative, analog, or prodrug of a therapeutic agent or modified therapeutic agent incorporated into the dosage kit and packaging possesses increased therapeutic efficacy or reduced side effects as compared with an unmodified therapeutic agent; and
(v) a therapeutically effective quantity of a therapeutic agent, a modified therapeutic agent, or a derivative, analog, or prodrug of a therapeutic agent or modified therapeutic agent that is subjected to a bulk drug product improvement, wherein the therapeutic agent, the modified therapeutic agent, or the derivative, analog, or prodrug of a therapeutic agent or modified therapeutic agent subject to the bulk drug product improvement possesses increased therapeutic efficacy or reduced side effects as compared with an unmodified therapeutic agent.

Typically, the composition possesses increased efficacy or reduced side effects for cancer therapy. Typically, the unmodified therapeutic agent is dianhydrogalactitol or diacetyldianhydrogalactitol.

In one alternative of a composition according to the present invention, the composition can comprise a drug combination comprising:
(i) dianhydrogalactitol; and
(ii) an additional therapeutic agent selected from the group consisting of:
   (a) topoisomerase inhibitors;
   (b) fraudulent nucleosides;
   (c) fraudulent nucleotides;
   (d) thymidylate synthetase inhibitors;
   (e) signal transduction inhibitors;
   (f) cisplatin or platinum analogs;
   (g) alkylating agents;
   (h) anti-tubulin agents;
   (i) antimetabolites;
   (j) berberine;
   (k) apigenin;
   (l) amonafide;
   (m) vinca alkaloids;
   (n) 5-fluorouracil;
   (o) curcumin;
   (p) NF-κB inhibitors;
   (q) rosmarinic acid;
   (r) mitoguazone;
   (s) tetrandrine;
   (t) an inhibitor of mutant isocitrate dehydrogenase (IDH);
   (u) a MGMT inhibitor; and
   (v) an agent that inhibits NF-κB-enhanced expression of MGMT.

In another alternative of a composition according to the present invention, the composition can comprise a drug combination comprising:
(i) diacetyldianhydrogalactitol; and
(ii) an additional therapeutic agent selected from the group consisting of:
   (a) topoisomerase inhibitors;
   (b) fraudulent nucleosides;
   (c) fraudulent nucleotides;
   (d) thymidylate synthetase inhibitors;
   (e) signal transduction inhibitors;
   (f) cisplatin or platinum analogs;
   (g) alkylating agents;
   (h) anti-tubulin agents;
   (i) antimetabolites;
   (j) berberine;
   (k) apigenin;
   (l) amonafide;
   (m) vinca alkaloids;
   (n) 5-fluorouracil;
   (o) curcumin;
   (p) NF-κB inhibitors;
   (q) rosmarinic acid;
   (r) mitoguazone;
   (s) tetrandrine;
   (t) an inhibitor of mutant isocitrate dehydrogenase (IDH);
   (u) a MGMT inhibitor; and
   (v) an agent that inhibits NF-κB-enhanced expression of MGMT.

In another alternative, the composition can comprise:
(i) dianhydrogalactitol; and
(ii) a therapeutic agent subject to chemosensitization selected from the group consisting of:
   (a) topoisomerase inhibitors;
   (b) fraudulent nucleosides;
   (c) fraudulent nucleotides;
   (d) thymidylate synthetase inhibitors;
   (e) signal transduction inhibitors;
   (f) cisplatin or platinum analogs;
   (g) alkylating agents;
   (h) anti-tubulin agents;
   (i) antimetabolites;
   (j) berberine;
   (k) apigenin;
   (l) amonafide;
   (m) vinca alkaloids;
   (n) 5-fluorouracil;
   (o) curcumin;
   (p) NF-κB inhibitors;
   (q) rosmarinic acid;
   (r) mitoguazone; and
   (s) tetrandrine;
wherein the dianhydrogalactitol acts as a chemosensitizer.

In yet another alternative, the composition can comprise:
(i) diacetyldianhydrogalactitol; and
(ii) a therapeutic agent subject to chemosensitization selected from the group consisting of:
   (a) topoisomerase inhibitors;
   (b) fraudulent nucleosides;
   (c) fraudulent nucleotides;
   (d) thymidylate synthetase inhibitors;
   (e) signal transduction inhibitors;
   (f) cisplatin or platinum analogs;
   (g) alkylating agents;
   (h) anti-tubulin agents;
   (i) antimetabolites;
   (j) berberine;
   (k) apigenin;
   (l) amonafide;
   (m) vinca alkaloids;
   (n) 5-fluorouracil;
   (o) curcumin;
   (p) NF-κB inhibitors;
   (q) rosmarinic acid;
   (r) mitoguazone; and
   (s) tetrandrine;
wherein the diacetyldianhydrogalactitol acts as a chemosensitizer.

In yet another alternative, the composition comprises:
(i) dianhydrogalactitol; and
(ii) a therapeutic agent subject to chemopotentiation selected from the group consisting of:

(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) vinca alkaloids;
(n) 5-fluorouracil;
(o) curcumin;
(p) NF-κB inhibitors;
(q) rosmarinic acid;
(r) mitoguazone;
(s) tetrandrine; and
(t) biotherapeutics;
wherein the dianhydrogalactitol acts as a chemopotentiator.

In yet another alternative, the composition comprises:
(i) diacetyldianhydrogalactitol; and
(ii) a therapeutic agent subject to chemopotentiation selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) vinca alkaloids;
(n) 5-fluorouracil;
(o) curcumin;
(p) NF-κB inhibitors;
(q) rosmarinic acid;
(r) mitoguazone;
(s) tetrandrine; and
(t) biotherapeutics;
wherein the diacetyldianhydrogalactitol acts as a chemopotentiator.

In yet another alternative of a composition according to the present invention, the therapeutic agent is dianhydrogalactitol or diacetyldianhydrogalactitol and the dianhydrogalactitol or diacetyldianhydrogalactitol is subjected to a bulk drug product improvement, wherein the bulk drug product improvement is selected from the group consisting of:
(a) salt formation;
(b) preparation as a homogeneous crystal structure;
(c) preparation as a pure isomer;
(d) increased purity;
(e) preparation with lower residual solvent content; and
(f) preparation with lower residual heavy metal content.

In still another alternative of a composition according to the present invention, the therapeutic agent is dianhydrogalactitol or diacetyldianhydrogalactitol and the composition comprises a diluent, wherein the diluent is selected from the group consisting of:
(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

In still another alternative of a composition according to the present invention, the therapeutic agent is dianhydrogalactitol or diacetyldianhydrogalactitol and the composition comprises a solvent system, wherein the solvent system is selected from the group consisting of:
(a) an emulsion;
(b) dimethylsulfoxide (DMSO);
(c) N-methylformamide (NMF);
(d) DMF;
(e) ethanol;
(f) benzyl alcohol;
(g) dextrose-containing water for injection;
(h) Cremophor;
(i) cyclodextrin; and
(j) PEG.

In still another alternative of a composition according to the present invention, the therapeutic agent is dianhydrogalactitol or diacetyldianhydrogalactitol and the composition comprises an excipient, wherein the excipient is selected from the group consisting of:
(a) mannitol;
(b) albumin;
(c) EDTA;
(d) sodium bisulfite;
(e) benzyl alcohol;
(f) a carbonate buffer; and
(g) a phosphate buffer.

In still another alternative of a composition according to the present invention, the therapeutic agent is dianhydrogalactitol or diacetyldianhydrogalactitol and the dianhydrogalactitol or diacetyldianhydrogalactitol is incorporated into a dosage form selected from the group consisting of:
(a) tablets;
(b) capsules;
(c) topical gels;
(d) topical creams;
(e) patches;
(f) suppositories; and
(g) lyophilized dosage fills.

In still another alternative of a composition according to the present invention, the therapeutic agent is dianhydrogalactitol or diacetyldianhydrogalactitol and the dianhydrogalactitol or diacetyldianhydrogalactitol is incorporated into a dosage kit and packaging selected from the group consisting of amber vials to protect from light and stoppers with specialized coatings to improve shelf-life stability.

In still another alternative of a composition according to the present invention, the therapeutic agent is dianhydrogalactitol or diacetyldianhydrogalactitol and the composition comprises a drug delivery system selected from the group consisting of:
(a) nanocrystals;
(b) bioerodible polymers;
(c) liposomes;
(d) slow release injectable gels; and
(e) microspheres.

In still another alternative of a composition according to the present invention, the therapeutic agent is dianhydrogalactitol or diacetyldianhydrogalactitol and the dianhydrogalactitol or diacetyldianhydrogalactitol is present in the composition in a drug conjugate form selected from the group consisting of:
  (a) a polymer system;
  (b) polylactides;
  (c) polyglycolides;
  (d) amino acids;
  (e) peptides; and
  (f) multivalent linkers.

In yet another alternative of a composition according to the present invention, the therapeutic agent is a modified dianhydrogalactitol or a modified diacetyldianhydrogalactitol and the modification is selected from the group consisting of:
  (a) alteration of side chains to increase or decrease lipophilicity;
  (b) addition of an additional chemical functionality to alter a property selected from the group consisting of reactivity, electron affinity, and binding capacity; and
  (c) alteration of salt form.

In yet another alternative of a composition according to the present invention, the therapeutic agent is dianhydrogalactitol or diacetyldianhydrogalactitol and the dianhydrogalactitol or diacetyldianhydrogalactitol is in the form of a prodrug system, wherein the prodrug system is selected from the group consisting of:
  (a) the use of enzyme sensitive esters;
  (b) the use of dimers;
  (c) the use of Schiff bases;
  (d) the use of pyridoxal complexes; and
  (e) the use of caffeine complexes.

In still another alternative of a composition according to the present invention, the therapeutic agent is dianhydrogalactitol or diacetyldianhydrogalactitol and the composition further comprises at least one additional therapeutic agent to form a multiple drug system, wherein the at least one additional therapeutic agent is selected from the group consisting of:
  (a) an inhibitor of multi-drug resistance;
  (b) a specific drug resistance inhibitor;
  (c) a specific inhibitor of a selective enzyme;
  (d) a signal transduction inhibitor;
  (e) an inhibitor of a repair enzyme; and
  (f) a topoisomerase inhibitor with non-overlapping side effects.

Analogous methods of use, compositions, and improvements also apply to other suboptimally administered therapeutic agents including, but not limited to, Avastin (bevacizumab), Rituxan (rituximab), Nexavar (sorafenib), dasatinib, nilotinib, Provenge (sipuleucel-T), Tarceva (erlotinib), and Iressa (gefitinib).

DETAILED DESCRIPTION OF THE INVENTION

This invention relates to novel compositions and methods to improve the utility of chemical agents including substituted hexitols such as dianhydrogalactitol or diacetyldianhydrogalactitol with suboptimal performance for patients with cancer, as well as additional therapeutic agents or agents capable of therapeutic application including, but not limited to, Avastin (bevacizumab), Rituxan (rituximab), Nexavar (sorafenib), dasatinib, nilotinib, Provenge (sipuleucel-T), Tarceva (erlotinib), Iressa (gefitinib), curcumin, berberine, and tetrandrine. The invention describes the novel development of improved pharmaceutical ingredients, dosage forms, excipients, solvents, diluents, drug delivery systems, preservatives, more accurate drug administrations, improved dose determination and schedules, toxicity monitoring and ameliorization, techniques or agents to circumvent or reduce toxicity, techniques and tools to identify/predict those patients who might have a better outcome with a therapeutic agent by the use of phenotype or genotype determination through the use of diagnostic kits or pharmacokinetic or metabolism monitoring approaches, the use of drug delivery systems, novel prodrugs, polymer conjugates, novel routes of administration, other agents to potentiate the activity of the compounds or inhibit the repair of suboptimal cellular effects or sub-lethal damage or to "push" the cell into more destructive cellular phases such as apoptosis. In some cases, the inventive examples include the use of these sub-optimal therapeutics in conjunction with radiation or other conventional chemotherapeutic agents or biotherapeutic agents such as antibodies, vaccines, cytokines, lymphokines, gene and antisense therapies, or other chemotherapeutic or biotherapeutic agents.

By definition, the term "suboptimal therapy" includes agents where Phase I toxicity precluded further human clinical evaluation. It also includes those agents from Phase II trials where limited or no significant tumor responses were identified. In addition, it also includes those agents, the subject of Phase III clinical trials, whose outcome was either medically or statistically not significant to warrant submission or approval by regulatory agencies for commercialization or commercialized agents whose response rates as a monotherapy are less than 25% or whose side-effects are severe enough to limit wider utility. Agents with suboptimal activity include but are not limited to the following: dianhydrogalactitol, diacetyldianhydrogalactitol, Avastin (bevacizumab), Rituxan (rituximab), Nexavar (sorafenib), dasatinib, nilotinib, Provenge (sipuleucel-T), Tarceva (erlotinib), and Iressa (gefitinib). More specifically, the inventive methods and compositions also focus on improvements for substituted hexitols including dianhydrogalactitol and diacetyldianhydrogalactitol.

(I) Suboptimal Therapeutics

In general, examples of compounds with suboptimal therapeutic activity include, but are not limited to, compounds of the following classes: DNA/nucleic acid binding/reactive agents, topoisomerase inhibitors, anti-tubulin agents, signal transduction inhibitors, protein synthesis inhibitors, inhibitors of DNA transcribing enzymes, DNA/RNA intercalating agents, DNA minor groove binders, drugs that block steroid hormone action, photochemically active agents, immune modifying agents, hypoxia selective cytotoxins, chemical radiation sensitizers and protectors, antisense nucleic acids, oligonucleotides and polynucleotides therapeutic agents, immune modifying agents, antitumor antibiotics, biotherapeutics, biologic agents such as cancer vaccines, antibody therapies, cytokines, lyphokines, gene therapies, nucleic acid therapies, and cellular therapies. In some cases, a compound may fall within more than one of these classes; such compounds are also within the scope of the invention.

In some cases, compounds or compositions may be in current clinical use for one or more indications, but yet be considered suboptimal for another indication, such as a different type of malignancy, either in terms of the cell type involved in the malignancy or in terms of the stage of the malignancy. Such compounds or compositions are within the scope of the invention.

Specific examples include: fluoropyrimidines; thiopurines; inhibitors of nucleoside diphosphate reductase; 2'-deoxyribonucleoside analogs; nucleosides; folic acid analogs;

methotrexate; 6-diazo-5-oxo-norleucine; L-asparaginase; N-(phosphoacetyl)-L-aspartic acid; nitrogen mustard; mechlorethamine; chlorambucil; melphalan; cyclophosphamide; estramustine; platinum complexes; nitrosoureas; BCNU; BCNU wafer (Gliadel); CCNU; streptozotocin; alkyl sulfonates; busulfan; clomesone; triazenylimidazoles and related triazenes; mitozolomide; temozolomide (Temodar); aziridines; tris(1-aziridinyl)phosphine sulfide; aziridinylphosphines; 3,6-diaziridinyl-2,5-bis(carboethoxyamino)-1,4-benzoquinone (Diaziquone) (AZQ); AZQ analogs; bendamustine (Treanada); procarbazine; hexamethylamine; topoisomerase I inhibitors, including camptothecin and camptothecin analogs; topoisomerase II inhibitors, including anthracyclines, doxorubicin, epirubicin, etoposide; DNA intercalating agents; amsacrine; CI-921 ((9-[[2-methoxy-4-[(methylsulfonyl)amino]phenyl]amino]-N,5-dimethyl-4-acridinecarboxamide 2-hydroxyethanesulfonate (1;1)), 1'-carbamate analogs of amsacrine; 9-aminoacridine-4-carboxamides; acridine carboxamide; tricyclic carboxamides; 1-nitroacridine; acridine derivatives; diacridines; triacridines; podophyllotoxins; ellipticine; merbarone; benzisoquinolinediones; etoposide; teniposide; aminoanthraquinones; inhibitors of DNA-transcribing enzymes; transcription inhibitors; replication inhibitors; RNA replication inhibitors; DNA or RNA polymerase inhibitors; rifamycins; actinomycins; DNA minor groove binding compounds; bisbenzimide (Hoechst 33258); mitomycins; CC-1065; mithramycins; chloromycins; olivomycins; phthalanilides; anthramycins; antimitotic agents; vinca alkaloids, including vinblastine and analogs and vincristine and analogs; navelbine; colchicine and analogs; bleomycin and analogs; estramustine; aromatase inhibitors; tamoxifen; LHRH antagonists and analogs porfimer; hematoporphyrins, electron-affinic oxygen mimetics; nitroaromatics; nitroheterocyclics; nitroimidazoles; tirapazamine, mitomycins; menadione and analogs; naphthoquinones; aziridoquinones; amine oxides; N-oxides; metal complexes; bioreductive agents; bioreductive alkylating agents; radiation sensitizers; radiation protectors; antisense agents; antigene agents; transcription factor inhibitors; ODN complexes; ribozymes; double-stranded RNA; antitumor antibiotics; acivicin; aclararubicin; acodazole; acronycine; adozelesin; alanosine; allopurinol; altretamine; aminoglutethimide; amonafide; amsacrine; androgens; anguidine; aphidicolin glycinate; asaley; 5-azacytidine; 5-aza-2'-deoxycytidine; azathioprine; Baker's Antifol; β-2'-deoxythioguanosine; bisantrene HCl; bleomycin sulfate; busulfan; buthionine sulfoximine (BSO); BWA 773U82; BW 502U83 HCl; BW 7U85 mesylate; caracemide; carbetimer; carboplatin; carmustine; chlorambucil; chloroquinoxaline sulfonamide; chlorozotocin; chromomycin A3; cisplatin; cladribine; carboplatin; oxaliplatin; rhodamine compounds; corticosteroids; irinotecan (CPT-11); cristanol; cyclocytidine; cyclophosphamide; cytarabine; cytembena; dabis maleate; dacarbazine; dactinomycin; daunorubicin HCl; deazauridine; dexrazoxane; diacetyldianhydrogalactitol (DADAG), dianhydrogalactitol (DAG); didemnin B; diethyldithiocarbamate; diglycoaldehyde; dihydro-5-azacytidine; doxorubicin; echinomycin; edatrexate; edelfosine; eflornithine; elsamitrucin; epirubicin; esorubicin; estramustine phosphate, estrogens; etanidazole; ethiofos; fadrazole; fazarabine; fenretinide; finasteride; flavone acetic acid; floxuridine; fludarabine phosphate; 5-fluorouracil; flutamide; gallium nitrate; gemcitabine; goserelin acetate; hepsulfam; hexamethylene bisacetamide; hydrazine sulfate; 4-hydroxyandrostenedione; hydroxyurea; idarubicin HCl; ifosfamide; 4-ipomeanol; iproplatin; isotretinoin; leuprolide acetate; levamisole; liposomal daunorubicin; liposomal doxorubicin; lomustine; lonidamine; maytansine; mechloethamine hydrochloride; menogaril; 6-mercaptopurine; mesna; N-methylformamide; mifepristone; mitoguazone; mitomycin C; mitotane; mitoxantrone hydrochloride; nabilone; nafoxidine; neocarzinostatin; octreotide acetate; ormaplatin; oxaliplatin; paclitaxe; pala; pentostatin; piperazinedione; pipobroman; pirarubicin; piritrexim; piroxantrone hydrochloride; plicamycin; porfimer sodium; predimustine; procarbazine; progestins; pyrazofurin; razoxane; sargramostim; semustine; spirogermanium; streptonigrin; streptozocin; sulofenur; suramin sodium; tamoxifen; taxotere; tegafur; teniposide; terephthalamidine; teroxirone; thioguanine; thiotepa; thymidine; tiazofurin; topotecan; tormifene; tretinoin; trifluoroperazine hydrochloride; trifluridine; trimetrexate; uracil mustard; vinblastine sulfate; vincristine sulfate; vindesine; vinorelbine; vinzolidine; Yoshi 864; zorubicin; 2-chloro-2'deoxyadenosine; 3-deazauridine; 4-nitroestrone; 6-methylmercaptopurine riboside; 9-aminocamptothecin; nitrocamptothecin; acodazole HCl; ADR-529; ICRF-187; amasacrine; aminothiadiazole; ADTA; amonafide; antibiotic FR901228; aphidicolin glycinate; AZT; bizelesin; brefeldins; wortmannins; cantharidins; bromodeoxyuridines; bryostatin; BSO; CAI; caracemide; chlorosulfaquinoxaline sulfonamide; cyclocytidine HCl; cyclodisone; cyclopentenylcytosine; deoxyspergualin; DHAC; didemnin B; dideoxy-β-fluorouracil; dideoxyadenosine; dideoxyinosine; dihydrotriazine benzene sulfonyl fluoride; dolastatin 10; ecteinascidin 743; etanidazole; ethiofos (WR-2721); fazarabine; flavopiridol; fludarabine phosphate; fostriecin; genistein; genistin; 6"-O-malonylgenistin, 6"-O-acetylgenistin; daidzein; daidzin; 6"-O-malonyldaidzin; 6"-O-acetylgenistin; glycitein; glycitin; 6"-O-malonylglycitin; 6-O-acetylglycitin; hepsulfam; HMBA; iododeoxyuridine; ipomeanol; KNI-272; leucovorin calcium; levamisole; menogaril; merbarone; misonidazole; mitoguazone; mitoxantrone HCl; mitozolomide; O6-benzylguanine; PALA; pancratistatin; penclomedine; pentamethylmelamine HCl; pentamidine isethionate; pentostatin; perillyl alcohol; phyllanthoside; pibenzimole HCl; piroxantrone; pyrazine diazohydroxide; pyrazoloacridine; quinocarmycins, rebeccamycins; rhizoxin; semustine; (methyl CCNU), suramin sodium; Nexavar; Gleevec; dasatinib (Sprycell); decitabine; 5-azacytidine (Vidaza); Homoharringtonine (HHT, omacetaxine); Taxol; temozolomide (Temodar); terephthalamidine; teroxirone; thioguanine; thymidine; tiazofurin; TMCA; topotecan; 5-fluorouracil; ras inhibitors; farnesylation inhibitors; bromodeoxyuridine, tetracycline compounds; arsenic trioxide; combretastatins; 2-methoxyestradiol; thalidomide and analogs; cephalotaxine derivatives; stributyrin; triciribine phosphate; trimetrexate; UCN-01; 7-hydroxystaurosporine; uridine; lycurium; ritrosulfan; artemisinin; artesunate; lonidamine; bromomannitol; pipobroman; phenesterin; pyrazine diazohydroxide; terephthalamidine; bufalin; FMDC; colchicine; thiocolchicine; colchicine analogs; LHRH analogs; curcumin; berberine; tetrandrine; paclitaxel; MGBG; Nexavar (sorafenib); nilotinib; Provenge (sipuleucel-T); Tarceva (erlotinib); Iressa (gefitinib); and antibody therapies such as Avastin, Herceptin, Rituxan, and Erbitux.

In particular, the invention is directed to galactitols, substituted galactitols, and derivatives thereof, including dianhydrogalactitol and diacetyldianhydrogalactitol.

The structure of dianhydrogalactitol is shown in Formula (I), below.

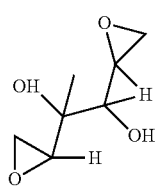

(I)

Also within the scope of the invention are derivatives of dianhydrogalactitol that, for example, have the hydrogen of the hydroxyl groups replaced with lower alkyl, have the hydrogen attached to the epoxide ring replaced with lower alkyl, or have the methyl groups attached to the same carbons that bear the hydroxyl groups replaced with lower alkyl or substituted with, for example, halo groups.

The structure of diacetyldianhydrogalactitol is shown in Formula (II), below.

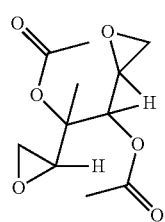

(II)

Also within the scope of the invention are derivatives of diacetyldianhydrogalactitol that, for example, have the methyl groups that are part of the acetyl moieties replaced with lower alkyl, have the hydrogen attached to the epoxide ring replaced with lower alkyl, or have the methyl groups attached to the same carbons that bear the acetyl groups replaced with lower alkyl or substituted with, for example, halo groups.

In another alternative, the invention is directed to an agent with suboptimal activity selected from the group consisting of: Avastin (bevacizumab), Rituxan (rituximab), Nexavar (sorafenib), dasatinib, nilotinib, Provenge (sipuleucel-T), Tarceva (erlotinib), and Iressa (gefitinib).

Avastin (bevacizumab) is a humanized (from mouse) monoclonal antibody that binds VEGF-A and is an angiogenesis inhibitor. It has been approved or suggested for use in combination with standard chemotherapy for metastatic colon cancer and non-small-cell lung cancer. There have been suggestions that it might be useful in metastatic breast cancer, although approval by the FDA for this specific indication was revoked. Bevacizumab has also been tried in macular degeneration, and clinical studies are also underway for bevacizumab in non-metastatic breast cancer, renal cell carcinoma, glioblastoma multiforme, ovarian cancer, hormone-refractory prostate cancer, non-metastatic unresectable liver cancer, and metastatic or unresectable locally advanced pancreatic cancer.

Rituxan (rituximab) is a chimeric mouse/human monoclonal antibody that binds CD20, which is a marker primarily found on the surface of B cells. Rituximab is used in the treatment of many leukemias and lymphomas; it is also used to treat transplant rejection and autoimmune disorders. It is being used in rheumatoid arthritis, particularly in combination with methotrexate, and is being used to some extent in multiple sclerosis, systemic lupus erythematosus, autoimmune anemias such as autoimmune hemolytic anemia, pure red cell aplasia, idiopathic thrombocytopenic purpura, Evans syndrome, vasculitis such as Wegener's granulomatosis, pemphigus, pemphigoid, Type 1 diabetes mellitus, Sjögren's syndrome, Devic's disease, and thyroid-associated opththalmopathy.

Nexavar (sorafenib) has the chemical structure 4-[4-[[4-chloro-3-(trifluoromethyl)phenyl]carbamoylamino]phenoxy]-N-methyl-pyridine-2-carboxamide and is an inhibitor of several tyrosine protein kinases (VEGFR and PDGFR) and Raf. Sorafenib targets the MAP kinase pathway (Raf/Mek/Erk pathway). It is used or suggested for use in advanced renal cancer, hepatocellular carcinoma, non-responsive thyroid cancer, and recurrent glioblastoma.

Dasatinib is an oral multi-BRC/ABL and Src family tyrosine kinase inhibitor that has the chemical structure N-(2-chloro-6-methylphenyl)-2-[[6-[4-(2-hydroxyethyl)-1-piperazinyl]-2-methyl-4-pyrimidinyl]amino]-5-thiazolecarboxamide monohydrate. It is currently used to treat chronic myelogenous leukemia and Philadelphia-chromosome-positive acute lymphoblastic leukemia, and is being evaluated for treatment of numerous other cancers.

Nilotinib is a tyrosine kinase inhibitor that inhibits BCR-ABL, KIT, LCK, EPHA3, EPHA8, DDR1, DDR2, PDGFRB, MAPK11 and ZAK kinases and has the chemical structure 4-methyl-N-[3-(4-methyl-1H-imidazol-1-yl)-5-(trifluoromethyl)phenyl]-3-[(4-pyridin-3-ylpyrimidin-2-yl)amino]benzamide hydrochloride salt. It is currently used to treat drug-resistant chronic myelogenous leukemia.

Provenge (sipuleucel-T) is a therapeutic cancer vaccine that is a protein subunit. It is currently being tried for metastatic, asymptomatic, hormone-refractory prostate cancer.

Tarceva (erlotinib) is an EGFR inhibitor that has the chemical structure N-(3-ethynylphenyl)-6,7-bis(2-methoxyethoxy)quinazolin-4-amine and is used to treat non-small-cell lung cancer, pancreatic cancer, and other types of cancer.

Iressa (gefitinib) is also an EGFR inhibitor that has the chemical structure N-(3-chloro-4-fluoro-phenyl)-7-methoxy-6-(3-morpholin-4-ylpropoxy)quinazolin-4-amine. Iressa also is effective in patients that have an EGFR mutation. Iressa is considered particularly effective in treating some types of non-small-cell lung cancer, including adenocarcinoma.

(II) Dose Modification

Improvements for suboptimal chemotherapeutics including substituted hexitols such as dianhydrogalactitol or diacetyldianhydrogalactitol are made by alterations to the time that the compound is administered, the use of dose-modifying agents that control the rate of metabolism of the compound, normal tissue protective agents, and other alterations. General examples include: variations of infusion schedules (e.g., bolus i.v. versus continuous infusion), the use of lymphokines (e.g., G-CSF, GM-CSF, EPO) to increase leukocyte count for improved immune response or for preventing anemia caused by myelosuppressive agents, or the use of rescue agents such as leucovorin for 5-FU or thiosulfate for cisplatin treatment. Specific inventive examples for substituted hexitols such as dianhydrogalactitol or diacetyldianhydrogalactitol include: continuous i.v. infusion for hours to days; biweekly administration; doses greater than 5 mg/m$^2$/day; progressive escalation of dosing from 1 mg/m$^2$/day based on patient tolerance; doses less than 1 mg/m$^2$ for greater than 14 days; use of caffeine to modulate metabolism; use of isoniazid to modulate metabolism; selected and intermittent boost dose administrations;

bolus single and multiple doses escalating from 5 mg/m$^2$; or oral doses below 30 or above 130 mg/m$^2$.

(III) Route of Administration

Improvements for suboptimal chemotherapeutics including substituted hexitols such as dianhydrogalactitol or diacetyldianhydrogalactitol are made by alterations in the route by which the compound is administered. General examples include: changing route from oral to intravenous administration and vice versa; or the use of specialized routes such as subcutaneous, intramuscular, intraarterial, intraperitoneal, intralesional, intralymphatic, intratumoral, intrathecal, intravesicular, intracranial. Specific inventive examples for substituted hexitols such as dianhydrogalactitol or diacetyldianhydrogalactitol include: topical; intravesicular for bladder cancer; oral administration; slow release oral delivery; intrathecal; intraarterial; continuous infusion; or intermittent infusion.

(IV) Schedule of Administration

Improvements for suboptimal chemotherapeutics including substituted hexitols such as dianhydrogalactitol or diacetyldianhydrogalactitol are made by alterations to the time that the compound is administered. General examples include: changing from a monthly administration to a weekly or daily dosing or variations of the schedule. Specific inventive examples for substituted hexitols such as dianhydrogalactitol or diacetyldianhydrogalactitol include: daily; weekly for three weeks, weekly for two weeks, biweekly; biweekly for three weeks with a 1-2 week rest period; intermittent boost dose administration; or daily for one week then once per week for multiple weeks.

(V) Indications for Use

Improvements for suboptimal chemotherapeutics including substituted hexitols such as dianhydrogalactitol or diacetyldianhydrogalactitol are made by alterations in the types of disease, clinical stage of disease that the compound is administered. General examples include: the use of solid tumor agents for leukemias and vice versa, the use of antitumor agents for the treatment of benign hyperproliferative disease such as psoriasis or benign prostate hypertrophy. Specific inventive examples for substituted hexitols such as dianhydrogalactitol or diacetyldianhydrogalactitol include: use for the treatment of leukemias (acute and chronic, ALL CLL, CML CLL); myelodysplastic syndrome (MDS); angiogenic diseases; benign prostate hypertrophy; psoriasis; gout; autoimmune conditions; prevention of transplantation rejection; restenosis prevention in cardiovascular disease; mycosis fungoides; use in bone marrow transplantation; as an anti-infective agent; treatment for AIDS; or treatment for lymphoma.

(VI) Disease Stages

Improvements for suboptimal chemotherapeutics including substituted hexitols such as dianhydrogalactitol or diacetyldianhydrogalactitol are made by alterations in the stage of disease at diagnosis/progression that the compound is administered. General examples include: the use of chemotherapy for non-resectable local disease, prophylactic use to prevent metastatic spread or inhibit disease progression or conversion to more malignant stages. Specific inventive examples for substituted hexitols such as dianhydrogalactitol or diacetyldianhydrogalactitol include: use for the treatment of localized polyp stage colon cancer; leukoplakia in the oral cavity; angiogenesis inhibition to prevent or limit metastatic spread; or against HIV with AZT, DDI, or reverse transcriptase inhibitors.

(VII) Other Indications

Improvements for suboptimal chemotherapeutics including substituted hexitols such as dianhydrogalactitol or diacetyldianhydrogalactitol are made by using the compound for non-malignant diseases and conditions. General examples include: premalignant conditions, benign hyperproliferative conditions, treatment of infections, parasites, usage to relieve pain, control of pleural effusions. Specific inventive examples for substituted hexitols such as dianhydrogalactitol or diacetyldianhydrogalactitol include: use as anti-infectives; use as antivirals; use as antibacterials; use for pleural effusions; use as antifungals; use as antiparasitics; use for eczema; use for shingles; use for condylomata; use as an anti-HPV agent; use as an anti-HSV agent.

(VIII) Patient Selection

Improvements for suboptimal chemotherapeutics including substituted hexitols such as dianhydrogalactitol or diacetyldianhydrogalactitol are made by alterations to the type of patient that would best tolerate or benefit from the use of the compound. General examples include: use of pediatric doses for elderly patients, altered doses for obese patients; exploitation of co-morbid disease conditions such as diabetes, cirrhosis, or other conditions that may uniquely exploit a feature of the compound. Specific inventive examples for substituted hexitols such as dianhydrogalactitol or diacetyldianhydrogalactitol include: patients with disease conditions with high levels of metabolic enzymes, histone deacetylase, protein kinases, or ornithine decarboxylase; patients with disease conditions with low levels of metabolic enzymes, histone deacetylase, protein kinases, or ornithine decarboxylase; patients with low or high susceptibility to thrombocytopenia or neutropenia; patients intolerant of GI toxicities; or over- or under-expression of jun, GPCR's and signal transduction proteins, VEGF, prostate specific genes, protein kinases, or telomerase.

(IX) Patient/Disease Phenotype

Improvements for suboptimal chemotherapeutics including substituted hexitols such as dianhydrogalactitol or diacetyldianhydrogalactitol are made by more precise identification of a patient's ability to tolerate, metabolize and exploit the use of the compound. General examples include: use of diagnostic tools and kits to better characterize a patient's ability to process/metabolize a chemotherapeutic agent or their susceptibility to toxicity caused by potential specialized cellular, metabolic, organ system phenotypes: Specific inventive examples for substituted hexitols such as dianhydrogalactitol or diacetyldianhydrogalactitol include: diagnostic tools, techniques, kits and assays to confirm a patient's particular phenotype and for the measurement of metabolism enzymes and metabolites, histone deacetylase, protein kinases, ornithine decarboxylase, VEGF, prostate specific genes, protein kinases, telomerase, jun GPCR's, quantity or activity of MGMT, methylation of MGMT promoter, and mutant isocitrate dehydrogenase (IDH); or surrogate compound dosing or low dose drug pre-testing for enzymatic status.

(X) Patient/Disease Genotype

Improvements for suboptimal chemotherapeutics including substituted hexitols such as dianhydrogalactitol or diacetyldianhydrogalactitol are made by testing and analyzing a patient's genotype for unique features that may be of value to predict efficacy, toxicity, metabolism, or other factors affecting the therapeutic efficacy of the drug. General examples include: biopsy samples of tumors or normal tissues (e.g., white blood cells) that may also be taken and analyzed to specifically tailor or monitor the use of a particular drug against a gene target; studies of unique tumor gene expression patterns; or analysis of SNP's (single nucleotide polymorphisms), to enhance efficacy or to avoid particular drug-sensitive normal tissue toxicities. Specific inventive examples for substituted hexitols such as dianhydrogalactitol or diacetyldianhydrogalactitol include: diagnostic tools, techniques, kits and assays to confirm a patient's particular genotype; gene/protein expression chips and analysis; Single Nucleotide Polymorphisms (SNP's) assessment; SNP's for histone deacetylase, ornithine decarboxylase, GPCR's, protein kinases, telomerase, or jun; or identification and the measurement of metabolism enzymes and metabolites.

(XI) Pre/Post-Treatment Preparation

Improvements for suboptimal chemotherapeutics including substituted hexitols such as dianhydrogalactitol or diacetyldianhydrogalactitol are made by specialized preparation of a patient prior to or after the use of a chemotherapeutic agent. General examples include: induction or inhibition of metabolizing enzymes, specific protection of sensitive normal tissues or organ systems. Specific inventive examples for substituted hexitols such as dianhydrogalactitol or diacetyldianhydrogalactitol include: the use of colchicine or analogs; use of diuretics such as probenecid; use of uricase; non-oral use of nicotinamide; sustained release forms of nicotinamide; use of inhibitors of polyADP ribose polymerase; use of caffeine; use of leucovorin rescue; use of infection control; or use of antihypertensives.

(XII) Toxicity Management

Improvements for suboptimal chemotherapeutics including substituted hexitols such as dianhydrogalactitol or diacetyldianhydrogalactitol are made by use of additional drugs or procedures to prevent or reduce potential side-effects or toxicities. General examples include: the use of anti-emetics, anti-nausea, hematological support agents to limit or prevent neutropenia, anemia, thrombocytopenia, vitamins, antidepressants, treatments for sexual dysfunction, and other supportive techniques. Specific inventive examples for substituted hexitols such as dianhydrogalactitol or diacetyldianhydrogalactitol include: the use of colchicine or analogs; use of diuretics such as probenecid; use of uricase; non-oral use of nicotinamide; use of sustained release forms of nicotinamide; use of inhibitors of poly ADP-ribose polymerase; use of caffeine; use of leucovorin rescue; use of sustained release allopurinol; non-oral use of allopurinol; use of bone marrow transplant stimulants, blood, platelet infusions, Neupogen, G-CSF, or GM-CSF; pain management; use of anti-inflammatories; fluids; corticosteroids; insulin control medications; anti-pyretics; anti-nausea treatments; anti-diarrhea treatment; N-acetyl cysteine; or antihistamines.

(XIII) Pharmacokinetic/Pharmacodynamic Monitoring

Improvements for suboptimal chemotherapeutics including substituted hexitols such as dianhydrogalactitol or diacetyldianhydrogalactitol are made by the use of monitoring drug levels after dosing in an effort to maximize a patient's drug plasma level, to monitor the generation of toxic metabolites, monitoring of ancillary medicines that could be beneficial or harmful in terms of drug-drug interactions. General examples include: the monitoring of drug plasma protein binding, and monitoring of other pharmacokinetic or pharmacodynamic variables. Specific inventive examples for substituted hexitols such as dianhydrogalactitol or diacetyldianhydrogalactitol include: multiple determinations of drug plasma levels; or multiple determinations of metabolites in the blood or urine.

(XIV) Drug Combinations

Improvements for suboptimal chemotherapeutics including substituted hexitols such as dianhydrogalactitol or diacetyldianhydrogalactitol are made by exploiting unique drug combinations that may provide a more than additive or synergistic improvement in efficacy or side-effect management. General examples include: alkylating agents with anti-metabolites, topoisomerase inhibitors with antitubulin agents. Specific inventive examples for substituted hexitols such as dianhydrogalactitol or diacetyldianhydrogalactitol include: in combination with topoisomerase inhibitors; use in combination with fraudulent nucleosides; use in combination with fraudulent nucleotides; use in combination with thymidylate synthetase inhibitors; use in combination with signal transduction inhibitors; use in combination with cisplatin or platinum analogs; use in combination with alkylating agents such as the nitrosoureas (BCNU, Gliadel wafers, CCNU) bendamustine (Treanda); use in combination with anti-tubulin agents; use in combination with anti-metabolites; use in combination with berberine; use in combination with apigenin; use in combination with amonafide; use in combination with colchicine and analogs; use in combination with genistein; use in combination with etoposide; use in combination with cytarabine; use in combination with camptothecins; use in combination with vinca alkaloids; use in combination with topoisomerase inhibitors; use in combination with 5-fluorouracil; use in combination with curcumin; use in combination with NF-κB inhibitors; use in combination with rosmarinic acid; use in combination with mitoguazone; use in combination with tetrandrine; use in combination with an inhibitor of mutant isocitrate dehydrogenase (IDH); use in combination with a MGMT inhibitor; use in combination with an agent that inhibits NF-κB-enhanced expression of MGMT; or use in combination with biological therapies such as antibodies such as Avastin, Rituxan, Herceptin, Erbitux.

(XV) Chemosensitization

Improvements for suboptimal chemotherapeutics including substituted hexitols such as dianhydrogalactitol or diacetyldianhydrogalactitol are made by exploiting them as chemosensitizers where no measurable activity is observed when used alone but in combination with other therapeutics a more than additive or synergistic improvement in efficacy is observed. General examples include: misonidazole with alkylating agents, or tirapazamine with cisplatin. Specific inventive examples for substituted hexitols such as dianhydrogalactitol or diacetyldianhydrogalactitol include: as a chemosensitizer in combination with topoisomerase inhibitors; as a chemosensitizer in combination with fraudulent nucleosides; as a chemosensitizer in combination with fraudulent nucleotides; as a chemosensitizer in combination with thymidylate synthetase inhibitors; as a chemosensitizer in combination with signal transduction inhibitors; as a chemosensitizer in combination with cisplatin or platinum analogs; as a chemosensitizer in combination with alkylating agents such as BCNU Gliadel wafers, CCNU, bendamustine (Treanda), temozolomide (Temodar); as a chemosensitizer in combination with anti-tubulin agents; as a chemosensitizer in combination with antimetabolites; as a chemosensitizer in combination with berberine; as a chemosensitizer in combination with apigenin; as a chemosensitizer in combination with amonafide; as a chemosensitizer in combination with colchicine and analogs; as a chemosensitizer in combination with genistein; as a chemosensitizer in combination with etoposide; as a chemosensitizer in combination with cytarabine; as a chemosensitizer in combination with camptothecins; as a chemosensitizer in combination with vinca alkaloids; as a chemosensitizer in combination with topoisomerase inhibitors; as a chemosensitizer in combination with 5-fluorouracil; as a chemosensitizer in combination with curcumin; as a chemosensitizer in combination with NF-κB inhibitors; as a chemosensitizer in combination with rosmarinic acid; as a chemosensitizer in combination with mitoguazone; or as a chemosensitizer in combination with tetrandrine.

(XVI) Chemopotentiation

Improvements for suboptimal chemotherapeutics including substituted hexitols such as dianhydrogalactitol or diacetyldianhydrogalactitol are made by exploiting them as chemopotentiators where minimal therapeutic activity is observed alone but in combination with other therapeutics unique drug a more than additive or synergistic improvement in efficacy is observed. General examples include: amonafide with cisplatin or 5-FU. Specific inventive examples for substituted hexitols such as dianhydrogalactitol or diacetyldianhydrogalactitol include: as a chemopotentiator in combination with topoisomerase inhibitors; as a chemopotentiator in combination with fraudulent nucleosides; as a chemopotentiator in combination with thymidylate synthetase inhibitors; as a chemopotentiator in combination with signal transduction inhibitors; as a chemopotentiator in combination with cisplatin or platinum analogs; as a chemopotentiator in combination with alkylating agents such as BCNU, BCNU wafers, Gliadel, or bendamustine (Treanda); as a chemopotentiator in combination with anti-tubulin agents; as a chemopotentiator in combination with antimetabolites; as a chemopotentiator in combination with berberine; as a chemopotentiator in combination with apigenin; as a chemopotentiator in combination with amonafide; as a chemopotentiator in combination with colchicine and analogs; as a chemopotentiator in combination with genistein; as a chemopotentiator in combination with etoposide; as a chemopotentiator in combination with cytarabine; as a chemopotentiator in combination with camptothecins; as a chemopotentiator in combination with vinca alkaloids; as a chemopotentiator in combination with topoisomerase inhibitors; as a chemopotentiator in combination with 5-fluorouracil; as a chemopotentiator in combination with curcumin; as a chemopotentiator in combination with NF-κB inhibitors; as a chemopotentiator in combination with rosmarinic acid; as a chemopotentiator in combination with mitoguazone; as a chemopotentiator in combination with or tetrandrine.

(XVII) Post-Treatment Patient Management

Improvements for suboptimal chemotherapeutics including substituted hexitols such as dianhydrogalactitol or diacetyldianhydrogalactitol are made by drugs, treatments and diagnostics to allow for the maximum benefit to patients treated with a compound. General examples include: pain management, nutritional support, anti-emetics, anti-nausea therapies, anti-anemia therapy, anti-inflammatories. Specific inventive examples for substituted hexitols such as dianhydrogalactitol or diacetyldianhydrogalactitol include: use with therapies associated with pain management; nutritional support; anti-emetics; anti-nausea therapies; anti-anemia therapy; anti-inflammatories: antipyretics; or immune stimulants.

(XVIII) Alternative Medicine/Therapeutic Support

Improvements for suboptimal chemotherapeutics including substituted hexitols such as dianhydrogalactitol or diacetyldianhydrogalactitol are made by the use of unapproved/non-conventional therapeutics or methods to enhance effectiveness or reduce side effects. General examples include: hypnosis, acupuncture, meditation, herbal medications and extracts, applied kinesiology, prayer. Specific inventive examples for substituted hexitols such as dianhydrogalactitol or diacetyldianhydrogalactitol include: hypnosis; acupuncture; meditation; herbal medications created either synthetically or through extraction including NF-κB inhibitors (such as parthenolide, curcumin, or rosmarinic acid); natural anti-inflammatories (including rhein or parthenolide); immunostimulants (such as those found in *Echinacea*); antimicrobials (such as berberine); flavonoids, isoflavones, and flavones (such as apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin); or applied kinesiology.

(XIX) Bulk Drug Product Improvements

Improvements for suboptimal chemotherapeutics including substituted hexitols such as dianhydrogalactitol or diacetyldianhydrogalactitol are made by alterations in the pharmaceutical bulk substance. General examples include: salt formation, homogeneous crystalline structure, pure isomers. Specific inventive examples for substituted hexitols such as dianhydrogalactitol or diacetyldianhydrogalactitol include: salt formation; homogeneous crystalline structure; pure isomers; increased purity; or lower residual solvents and heavy metals.

(XX) Diluent Systems

Improvements for suboptimal chemotherapeutics including substituted hexitols such as dianhydrogalactitol or diacetyldianhydrogalactitol are made by alterations in the diluents used to solubilize and deliver/present the compound for administration. General examples include: Cremophor-EL, cyclodextrins for poorly water soluble compounds. Specific inventive examples for substituted hexitols such as dianhydrogalactitol or diacetyldianhydrogalactitol include: use of emulsions; dimethyl sulfoxide (DMSO); N-methylformamide (NMF); dimethylformamide (DMF); dimethylacetamide (DMA); ethanol; benzyl alcohol; dextrose containing water for injection; Cremophor; cyclodextrins; or PEG.

(XXI) Solvent Systems

Improvements for suboptimal chemotherapeutics including substituted hexitols such as dianhydrogalactitol or diacetyldianhydrogalactitol are made by alterations in the solvents used or required to solubilize a compound for administration or for further dilution. General examples include: ethanol, dimethylacetamide (DMA). Specific inventive examples for substituted hexitols such as dianhydrogalactitol or diacetyldianhydrogalactitol include: the use of emulsions; DMSO; NMF; DMF; DMA; ethanol; benzyl alcohol; dextrose containing water for injection; Cremophor; or PEG.

(XXII) Excipients

Improvements for suboptimal chemotherapeutics including substituted hexitols such as dianhydrogalactitol or diacetyldianhydrogalactitol are made by alterations in the materials/excipients, buffering agents, or preservatives required to stabilize and present a chemical compound for proper administration. General examples include: mannitol, albumin, EDTA, sodium bisulfite, benzyl alcohol. Specific inventive examples for substituted hexitols such as dianhydrogalactitol or diacetyldianhydrogalactitol include: the use of mannitol; albumin; EDTA; sodium bisulfite; benzyl alcohol; carbonate buffers; or phosphate buffers.

(XXII) Dosage Forms

Improvements for suboptimal chemotherapeutics including substituted hexitols such as dianhydrogalactitol or diacetyldianhydrogalactitol are made by alterations in the potential dosage forms of the compound dependent on the route of administration, duration of effect, plasma levels required, exposure to side-effect normal tissues and metabolizing enzymes. General examples include: tablets, capsules, topical gels, creams, patches, suppositories. Specific inventive examples for substituted hexitols such as dianhydrogalactitol or diacetyldianhydrogalactitol include: the use of tablets; capsules; topical gels; topical creams; patches; suppositories; or lyophilized dosage fills.

(XXIV) Dosage Kits and Packaging

Improvements for suboptimal chemotherapeutics including substituted hexitols such as dianhydrogalactitol or diacetyldianhydrogalactitol are made by alterations in the dosage forms, container/closure systems, accuracy of mixing and dosage preparation and presentation. General examples include: amber vials to protect from light, stoppers with specialized coatings. Specific inventive examples for substituted hexitols such as dianhydrogalactitol or diacetyldianhydrogalactitol include: the use of amber vials to protect from light or stoppers with specialized coatings to improve shelf-life stability.

(XXV) Drug Delivery Systems

Improvements for suboptimal chemotherapeutics including substituted hexitols such as dianhydrogalactitol or diacetyldianhydrogalactitol are made by the use of delivery systems to improve the potential attributes of a pharmaceutical product such as convenience, duration of effect, reduction of toxicities. General examples include: nanocrystals, bioerodible polymers, liposomes, slow release injectable gels, microspheres. Specific inventive examples for substituted hexitols such as dianhydrogalactitol or diacetyldianhydrogalactitol include: the use of nanocrystals; bioerodible polymers; liposomes; slow release injectable gels; or microspheres.

(XXVI) Drug Conjugate Forms

Improvements for suboptimal chemotherapeutics including substituted hexitols such as dianhydrogalactitol or diacetyldianhydrogalactitol are made by alterations to the parent molecule with covalent, ionic, or hydrogen bonded moieties to alter the efficacy, toxicity, pharmacokinetics, metabolism, or route of administration. General examples include: polymer systems such as polyethylene glycols, polylactides, polyglycolides, amino acids, peptides, or multivalent linkers. Specific inventive examples for substituted hexitols such as dianhydrogalactitol or diacetyldianhydrogalactitol include: the use of polymer systems such as polyethylene glycols; polylactides; polyglycolides; amino acids; peptides; or multivalent linkers.

(XXVII) Compound Analogs

Improvements for suboptimal chemotherapeutics including substituted hexitols such as dianhydrogalactitol or diacetyldianhydrogalactitol are made by alterations to the parent structure of a molecule with additional chemical functionalities that may alter efficacy, or reduce toxicity, pharmacological performance, route of administration, or another relevant factor for therapeutic efficacy. General examples include: alteration of side chains to increase or decrease lipophilicity, additional chemical functionalities to alter reactivity, electron affinity, binding capacity, salt forms. Specific inventive examples for substituted hexitols such as dianhydrogalactitol or diacetyldianhydrogalactitol include: alteration of side chains to increase or decrease lipophilicity; additional chemical functionalities to alter reactivity; electron affinity; binding capacity; or salt forms.

(XXVIII) Prodrugs

Improvements for suboptimal chemotherapeutics including substituted hexitols such as dianhydrogalactitol or diacetyldianhydrogalactitol are made by alterations to the molecule such that improved pharmaceutical performance is gained with a variant of the active molecule in that after introduction into the body a portion of the molecule is cleaved to reveal the preferred active molecule. General examples include: enzyme sensitive esters, dimers, Schiff bases. Specific inventive examples for substituted hexitols such as dianhydrogalactitol or diacetyldianhydrogalactitol include: the use of enzyme sensitive esters; dimers; Schiff bases; pyridoxal complexes; or caffeine complexes.

(XXIX) Multiple Drug Systems

Improvements for suboptimal chemotherapeutics including substituted hexitols such as dianhydrogalactitol or diacetyldianhydrogalactitol are made by the use of additional compounds, biological agents that when administered in the proper fashion, a unique and beneficial effect can be realized. General examples include: inhibitors of multi-drug resistance, specific drug resistance inhibitors, specific inhibitors of selective enzymes, signal transduction inhibitors, repair inhibition. Specific inventive examples for substituted hexitols such as dianhydrogalactitol or diacetyldianhydrogalactitol include: the use of inhibitors of multi-drug resistance; specific drug resistance inhibitors; specific inhibitors of selective enzymes; signal transduction inhibitors; repair inhibition; or topoisomerase inhibitors with non-overlapping side effects.

(XXX) Biotherapeutic Enhancement

Improvements for suboptimal chemotherapeutics including substituted hexitols such as dianhydrogalactitol or diacetyldianhydrogalactitol are made by their use in combination as sensitizers/potentiators with biological response modifiers. General examples include: use in combination as sensitizers/poteniators with biological response modifiers, cytokines, lymphokines, therapeutic antibodies, antisense therapies, gene therapies. Specific inventive examples for substituted hexitols such as dianhydrogalactitol or diacetyldianhydrogalactitol include: use in combination as sensitizers/potentiators with biological response modifiers; cytokines; lymphokines; therapeutic antibodies; antisense therapies; therapies such as Avastin, Herceptin, Rituxan, and Erbitux; gene therapies; ribozymes; or RNA interference.

(XXXI) Biotherapeutic Resistance Modulation

Improvements for suboptimal chemotherapeutics including substituted hexitols such as dianhydrogalactitol or diacetyldianhydrogalactitol are made by exploiting their selective use to overcome developing or complete resistance to the efficient use of biotherapeutics. General examples include: tumors resistant to the effects of biological response modifiers, cytokines, lymphokines, therapeutic antibodies, antisense therapies, gene therapies. Specific inventive examples for substituted hexitols such as dianhydrogalactitol or diacetyldianhydrogalactitol include: the use against tumors resistant to the effects of biological response modifiers; cytokines; lymphokines; therapeutic antibodies; antisense therapies; therapies such as Avastin, Rituxan, Herceptin, and Erbitux; gene therapies; ribozymes; or RNA interference.

(XXXII) Radiation Therapy Enhancement

Improvements for suboptimal chemotherapeutics including substituted hexitols such as dianhydrogalactitol or diacetyldianhydrogalactitol are made by exploiting their use in combination with ionizing radiation, phototherapies, heat therapies, or radio-frequency generated therapies. General examples include: hypoxic cell sensitizers, radiation sensitizers/protectors, photosensitizers, radiation repair inhibitors. Specific inventive examples for substituted hexitols such as dianhydrogalactitol or diacetyldianhydrogalactitol include: the use with hypoxic cell sensitizers; radiation sensitizers/protectors; photosensitizers; radiation repair inhibitors; thiol depletion; vaso-targeted agents; use with radioactive seeds, radionuclides, radiolabeled antibodies; or brachytherapy.

(XXXIII) Novel Mechanisms of Action

Improvements for suboptimal chemotherapeutics including substituted hexitols such as dianhydrogalactitol or diacetyldianhydrogalactitol are made by optimizing their utility by determining the various mechanisms of action, biological targets of a compound for greater understanding and precision to better exploit the utility of the molecule. General examples include: Gleevec for chronic myelocytic leukemia (CML), arsenic trioxide for acute promyelocytic leukemia (APL), retinoic acid for APL. Specific inventive examples for substituted hexitols such as dianhydrogalactitol or diacetyldianhydrogalactitol include: the use with inhibitors of poly-ADP ribose polymerase; agents that effect vasculature; vasodilation; oncogenic targeted agents; signal transduction inhibitors; EGFR inhibition; Protein Kinase C inhibition; Phospholipase C down-regulation; jun down-regulation; histone genes; VEGF; ornithine decarboxylase; jun D; v-jun; GPCRs; protein kinase A; telomerase, prostate specific genes; protein kinases; or histone deacetylase.

(XXXIV) Selective Target Cell Population Therapeutics

Improvements for suboptimal chemotherapeutics including substituted hexitols such as dianhydrogalactitol or diacetyldianhydrogalactitol are made by more precise identification and exposure of the compound to those select cell populations where the compound's effect can be maximally exploited. General examples include: tirapazamine and mitomycin C for hypoxic cells, vinca alkaloids for cells entering mitosis. Specific inventive examples for substituted hexitols such as dianhydrogalactitol or diacetyldianhydrogalactitol include: use against radiation sensitive cells; radiation resistant cells; energy depleted cells; or endothelial cells.

Accordingly, one aspect of the present invention is a method to improve the efficacy and/or reduce the side effects of suboptimally administered drug therapy comprising the steps of:

(1) identifying at least one factor or parameter associated with the efficacy and/or occurrence of side effects of the drug therapy; and (2) modifying the factor or parameter to improve the efficacy and/or reduce the side effects of the drug therapy.

Typically, the factor or parameter is selected from the group consisting of:

(1) dose modification;
(2) route of administration;
(3) schedule of administration;
(4) indications for use;
(5) selection of disease stage;
(6) other indications;
(7) patient selection;
(8) patient/disease phenotype;
(9) patient/disease genotype;
(10) pre/post-treatment preparation
(11) toxicity management;
(12) pharmacokinetic/pharmacodynamic monitoring;
(13) drug combinations;
(14) chemosensitization;
(15) chemopotentiation;
(16) post-treatment patient management;
(17) alternative medicine/therapeutic support;
(18) bulk drug product improvements;
(19) diluent systems;
(20) solvent systems;
(21) excipients;
(22) dosage forms;
(23) dosage kits and packaging;
(24) drug delivery systems;
(25) drug conjugate forms;
(26) compound analogs;
(27) prodrugs;
(28) multiple drug systems;
(29) biotherapeutic enhancement;
(30) biotherapeutic resistance modulation;
(31) radiation therapy enhancement;
(32) novel mechanisms of action; and
(33) selective target cell population therapeutics.

Typically, the hyperproliferative disease is cancer. Methods according to the present invention are applicable to many forms of cancer, including, but not limited to: (A) breast cancer, including: (1) ductal carcinoma, including ductal carcinoma in situ (DCIS) (comedocarcinoma, cribriform, papillary, micropapillary), infiltrating ductal carcinoma (IDC), tubular carcinoma, mucinous (colloid) carcinoma, papillary carcinoma, metaplastic carcinoma, and inflammatory carcinoma; (2) lobular carcinoma, including lobular carcinoma in situ (LCIS) and invasive lobular carcinoma; and (3) Paget's disease of the nipple; (B) cancers of the female reproductive system, including: (1) cancers of the cervix uteri, including cervical intraepithelial neoplasia (Grade I), cervical intraepithelial neoplasia (Grade II), cervical intraepithelial neoplasia (Grade III) (squamous cell carcinoma in situ), keratinizing squamous cell carcinoma, nonkeratinizing squamous cell carcinoma, verrucous carcinoma, adenocarcinoma in situ, adenocarcinoma in situ, endocervical type, endometrioid adenocarcinoma, clear cell adenocarcinoma, adenosquamous carcinoma, adenoid cystic carcinoma, small cell carcinoma, and undifferentiated carcinoma; (2) cancers of the corpus uteri, including endometrioid carcinoma, adenocarcinoma, adenocanthoma (adenocarcinoma with squamous metaplasia), adenosquamous carcinoma (mixed adenocarcinoma and squamous cell carcinoma, mucinous adenocarcinoma, serous adenocarcinoma, clear cell adenocarcinoma, squamous cell adenocarcinoma, and undifferentiated adenocarcinoma; (3) cancers of the ovary, including serous cystadenoma. serous cystadenocarcinoma, mucinous cystadenoma, mucinous cystadenocarcinoma, endometrioid tumor, endometrioid adenocarcinoma, clear cell tumor, clear cell cystadenocarcinoma, and unclassified tumor; (4) cancers of the vagina, including squamous cell carcinoma and adenocarcinoma; and (5) cancers of the vulva, including vulvar intraepithelial neoplasia (Grade I), vulvar intraepithelial neoplasia (Grade II), vulvar intraepithelial neoplasia (Grade III) (squamous cell carcinoma in situ); squamous cell carcinoma, verrucous carcinoma, Paget's disease of the vulva, adenocarcinoma (NOS), basal cell carcinoma (NOS), and Bartholin's gland carcinoma; (C) cancers of the male reproductive system, including: (1) cancers of the penis, including squamous cell carcinoma; (2) cancers of the prostate, including adenocarcinoma, sarcoma, and transitional cell carcinoma of the prostate; (3) cancers of the testis, including seminomatous tumor, nonseminomatous tumor, teratoma, embryonal carcinoma, yolk sac tumor, and Choriocarcinoma; (D) cancers of the cardiac system, including sarcoma (angiosarcoma, fibrosarcoma, rhabdomyosarcoma, liposarcoma), myxoma, rhabdomyoma, fibroma, lipoma and teratoma; (E) cancers of the respiratory system, including squamous cell carcinoma of the larynx, primary pleural mesothelioma, and squamous cell carcinoma of the pharynx; (F) cancers of the lung, including squamous cell carcinoma (epidermoid carcinoma), variants of squamous cell carcinoma, spindle cell carcinoma, small cell carcinoma, carcinoma of other cells, carcinoma of intermediate cell type, combined oat cell carcinoma, adenocarcinoma, acinar adenocarcinoma, papillary adenocarcinoma, bronchiolo-alveolar carcinoma, solid carcinoma with mucus formation, large cell carcinoma, giant cell carcinoma, clear cell carcinoma, and sarcoma; (G) cancers of the gastrointestinal tract, including: (1) cancers of the ampulla of Vater, including primary adenocarcinoma, carcinoid tumor, and lymphoma; (2) cancers of the anal canal, including adenocarcinoma, squamous cell carcinoma, and melanoma; (3) cancers of the extrahepatic bile ducts, including carcinoma in situ, adenocarcinoma, papillary adenocarcinoma, adenocarcinoma, intestinal type, mucinous adenocarcinoma, clear cell adenocarcinom, segnet-ring cell carcinoma, adenosquamous carcinoma, squamous cell carcinoma, small cell (oat) carcinoma, undifferentiated carcinoma, carcinoma (NOS), sarcoma, and carcinoid tumor; (4) cancers of the colon and rectum, including adenocarcinoma in situ, adenocarcinoma, mucinous adenocarcinoma (colloid type; greater than 50% mucinous carcinoma), signet ring cell carcinoma (greater than 50% signet ring cell), squamous cell (epidermoid) carcinoma, adenosquamous carcinoma, small cell (oat cell) carcinoma, undifferentiated carcinoma, carcinoma (NOS), sarcoma, lymphoma, and carcinoid tumor; (5) cancers of the esophagus, including squamous cell carcinoma, adenocarcinoma, leiomyosarcoma, and lymphoma; (6) cancers of the gallbladder, including adenocarcinoma, adenocarcinoma, intestinal type, adenosquamous carcinoma, carcinoma in situ, carcinoma (NOS), clear cell adenocarcinoma, mucinous adenocarcinoma, papillary adenocarcinoma, signet-ring cell carcinoma, small cell (oat cell) carcinoma, squamous cell carcinoma, and undifferentiated carcinoma; (7) cancers of the lip and oral cavity, including squamous cell carcinoma; (8) cancers of the liver, including hepatoma (hepatocellular carcinoma), cholangiocarcinoma, hepatoblastoma, angiosarcoma, hepatocellular adenoma, and hemangioma; (9) cancers of the exocrine pancreas, including duct cell carcinoma, pleomorphic giant cell carcinoma, giant cell carcinoma, osteoclastoid type, adenocarcinoma, adenosquamous carcinoma, mucinous (colloid) carcinoma, cystadenocarcinoma, acinar cell carcinoma, papillary carcinoma, small cell (oat cell) carcinoma, mixed cell typed, carcinoma (NOS), undifferentiated carcinoma, endocrine cell tumors arising in the islets of langerhans, and carcinoid; (10) cancers of the salivary glands, including acinic (acinar) cell carcinoma, adenoid cystic carcinoma (cylindroma), adenocarcinoma, squamous cell carcinoma, carcinoma in pleomorphic adenoma (malignant mixed tumor), mucoepidermoid carcinoma (well differentiated or low grade), and mucoepidermoid carcinoma (poorly differentiated or high grade); (11) cancers of the stomach, including adenocarcinoma, papillary adenocarcinoma, tubular adenocarcinoma, mucinous adenocarcinoma, signet ring cell carcinoma, adenosquamous carcinoma, squamous cell carcinoma, small cell carcinoma, undifferentiated carcinoma, lymphoma, sarcoma, and carcinoid tumor; and (12) cancers of the small intestine, including adenocarcinoma, lymphoma, carcinoid tumors, Kaposi's sarcoma, leiomyoma, hemangioma, lipoma, neurofibroma, and fibroma; (H) cancers of the urinary system, including: (1) cancers of the kidney, including renal cell carcinoma, carcinoma of Bellini's collecting ducts, adenocarcinoma, papillary carcinoma, tubular carcinoma, granular cell carcinoma, clear cell carcinoma (hypernephroma), sarcoma of the kidney, and nephroblastoma; (2) cancers of the renal pelvis and ureter, including transitional cell carcinoma, papillary transitional cell carcinoma, squamous cell carcinoma, and adenocarcinoma; (3) cancers of the urethra, including transitional cell carcinoma, squamous cell carcinoma, and adenocarcinoma; and (4) cancers of the urinary bladder, including carcinoma in situ, transitional urothelial cell carcinoma, papillary transitional cell carcinoma, squamous cell carcinoma, adenocarcinoma, undifferentiated; (I) cancers of muscle, bone, and soft tissue, including: (1) cancers of bone, including: (a) bone-forming: osteosarcoma; (b) cartilage-forming: chondrosarcoma and mesenchymal chondrosarcoma; (c) diant cell tumor, malignant; (d) Ewing's sarcoma; (e) vascular tumors: hemangioendothelioma, hemangiopericytoma, and angiosarcoma; (f) connective tissue tumors: fibrosarcoma, liposarcoma, malignant mesenchymoma, and undifferentiated sarcoma; and (g) other tumors: chordoma and adamantinoma of long bones; (2) cancers of soft tissues, including: alveolar soft-part sarcoma, angiosarcoma, epithelioid sarcoma, extraskeletal chondrosarcoma, fibrosarcoma, leiomyosarcoma, liposarcoma, malignant fibrous histiocytoma, malignant hemangiopericytoma, malignant mesenchymoma, malignant schwannoma, rhabdomyosarcoma, synovial sarcoma, and sarcoma (NOS); (3) cancers of the nervous system, including cancers of the skull (osteoma, hemangioma, granuloma, xanthoma, osteitis deformans), cancers of the meninges (meningioma, meningiosarcoma, gliomatosis), cancers of the brain (astrocytoma, medulloblastoma, glioma, ependymoma, germinoma (pilealoma), glioblastoma multiform, oligodendroglioma, schwannoma, retinoblastoma, congenital tumors), and cancers of the spinal cord neurofibroma, meningioma, glioma, sarcoma); (4) hematologic cancers, including myeloid leukemia (acute and chronic), acute lymphloblastic leukemia, chronic lymphocytic leukemia, myeloproliferative diseases, multiple myeloma; myelodysplastic syndrome), Hodgkin's disease, and non-Hodgkin's lymphoma (malignant lymphoma); (5) cancers of the endocrine system, including: (a) cancers of the thyroid gland, including papillary carcinoma (including those with follicular foci), follicular carcinoma, medullary carcinoma, and undifferentiated (anaplastic) carcinoma; and (b) neuroblastomas, including sympathicoblastoma, sympathicogonioma, malignant ganglioneuroma, gangliosympathicoblastoma, and ganglioneuroma; (6) cancers of the skin, including squamous cell carcinoma, spindle cell variant of squamous cell carcinoma, basal cell carcinoma, adenocarcinoma developing from sweat or sebaceous gland, and malignant melanoma; (7) cancers of the eye, including: (a) cancers of the conjunctiva, including carcinoma of the conjunctiva; (b) cancers of the eyelid, including basal cell carcinoma, squamous cell carcinoma, melanoma of the eyelid, and sebaceous cell carcinoma; (c) cancers of the lacrimal gland, including adenocarcinoma, adenoid cystic carcinoma, carcinoma in pleomorphic adenoma, mucoepidermoid carcinoma, and squamous cell carcinoma; (d) cancers of the uvea, including spindle cell melanoma, mixed cell melanoma, and epithelioid cell melanoma; (e) cancers of the orbit, including sarcoma of the orbit, soft tissue tumor, and sarcoma of bone; and (f) retinoblastoma. In particular, methods according to the present invention and compositions suitable for use according to those methods are applicable to lower grade astrocytomas and other primary central nervous system tumors besides glioblastoma multiforme (GBM), as well as to central nervous system metastases of other tumors including solid tumors and hematologic tumors (e.g., breast, lung, bladder, and bowel tumors, leukemias, and lymphomas), in addition to squamous cell non-small cell lung cancer. In addition, methods according to the present invention and compositions suitable for use according to those methods are applicable to melanoma, breast lymphoma (both Hodgkins and non-Hodgkins), colorectal cancer, acute lymphoblastic leukemia, and for lowering the incidence of central nervous system leukemia, non-small cell lung cancer, cervical carcinoma, bladder carcinoma, and metastatic hemangiopericytoma.

In one alternative, preferably, the substituted hexitol is selected from the group consisting of dianhydrogalactitol and a derivative thereof. In this alternative, more preferably, the substituted hexitol is dianhydrogalactitol. In another alternative, preferably, the substituted hexitol is selected from the group consisting of diacetyldianhydrogalactitol and a derivative thereof. In this alternative, more preferably, the substituted hexitol is diacetyldianhydrogalactitol. Derivatives of dianhydrogalactitol and of diacetyldianhydrogalactitol are described above.

The following improvements all apply either to dianhydrogalactitol, diacetyldianhydrogalactitol, or derivatives of either dianhydrogalactitol or diacetyldianhydrogalactitol, as indicated with respect to the specific improvement described below.

When the improvement is dose modification, the dose modification can be, but is not limited to, at least one dose modification selected from the group consisting of:
  (a) continuous i.v. infusion for hours to days;
  (b) biweekly administration;
  (c) doses greater than 5 mg/m$^2$/day;
  (d) progressive escalation of dosing from 1 mg/m$^2$/day based on patient tolerance;
  (e) use of caffeine to modulate metabolism;
  (f) use of isonazid to modulate metabolism;
  (g) selected and intermittent boosting of dosage administration;
  (h) administration of single and multiple doses escalating from 5 mg/m$^2$/day via bolus;
  (i) oral dosages of below 30 mg/m$^2$; and
  (j) oral dosages of above 130 mg/m$^2$.

When the improvement is made by route of administration, the route of administration can be, but is not limited to, at least one route of administration selected from the group consisting of:
  (a) topical administration;
  (b) intravesicular administration for bladder cancer;
  (c) oral administration;
  (d) slow release oral delivery;
  (e) intrathecal administration;
  (f) intraarterial administration;
  (g) continuous infusion; and
  (h) intermittent infusion.

When the improvement is made by schedule of administration, the schedule of administration can be, but is not limited to, at least one schedule of administration selected from the group consisting of:
  (a) daily administration;
  (b) weekly administration;
  (c) weekly administration for three weeks;
  (d) biweekly administration;
  (e) biweekly administration for three weeks with a 1-2 week rest period;
  (f) intermittent boost dose administration; and
  (g) daily administration for one week for multiple weeks.

When the improvement is made by indication for use, the indication for use can be, but is not limited to, at least one indication for use selected from the group consisting of:
  (a) use for treatment of leukemias;
  (b) use for treatment of myelodysplastic syndrome;
  (c) use for treatment of angiogenic diseases;
  (d) use for treatment of benign prostatic hyperplasia;
  (e) use for treatment of psoriasis;
  (f) use for treatment of gout;
  (g) use for treatment of transplantation rejections;
  (h) use for prevention of restenosis in cardiovascular disease;
  (i) use for treatment of mycosis fungoides;
  (j) use in bone marrow transplantation;
  (k) use as an anti-infective agent;
  (l) use for treatment of AIDS; and
  (m) use for treatment of lymphoma.

When the improvement is made by selection of disease stage, the selection of disease stage can be, but is not limited to, at least one selection of disease stage selected from the group consisting of:
  (a) use for the treatment of localized polyp stage colon cancer;
  (b) use for leukoplakia in the oral cavity;
  (c) use for angiogenesis inhibition to prevent or limit metastatic spread of a malignancy; and
  (d) use for treatment of HIV with a therapy selected from the group consisting of azidothymidine (AZT), dideoxyadenosine (DDI), and reverse transcriptase inhibitors.

When the improvement is made by other indications, the other indications can be, but are not limited, to at least one other indication selected from the group consisting of:
  (a) use as an anti-infective agent;
  (b) use as an antiviral agent;
  (c) use as an antibacterial agent;
  (d) use as an agent to treat pleural effusion;
  (e) use as an antifungal agent;
  (f) use as an anti-parasitic agent;
  (g) use as an agent to treat eczema;
  (h) use as an agent to treat herpes zoster (shingles);
  (i) use as an agent to treat condylomata;
  (j) use as an agent to treat human papilloma virus (HPV); and
  (k) use as an agent to treat herpes simplex virus (HSV).

When the improvement is made by patient selection, the patient selection can be, but is not limited to, a patient selection carried out by a criterion selected from the group consisting of:
  (a) selecting patients with a disease condition characterized by a high level of a metabolic enzyme selected from the group consisting of histone deacetylase and ornithine decarboxylase;
  (b) selecting patients with a low or high susceptibility to a condition selected from the group consisting of thrombocytopenia and neutropenia;
  (c) selecting patients intolerant of GI toxicities; and
  (d) selecting patients characterized by over- or under-expression of a gene selected from the group consisting of c-Jun, a GPCR, a signal transduction protein, VEGF, a prostate-specific gene, and a protein kinase.

The cellular proto-oncogene c-Jun encodes a protein that, in combination with c-Fos, forms the AP-1 early response transcription factor. This proto-oncogene plays a key role in transcription and interacts with a large number of proteins affecting transcription and gene expression. It is also involved in proliferation and apoptosis of cells that form part of a number of tissues, including cells of the endometrium and glandular epithelial cells. G-protein coupled receptors (GPCRs) are important signal transducing receptors. The superfamily of G protein coupled receptors includes a large number of receptors. These receptors are integral membrane proteins characterized by amino acid sequences that contain seven hydrophobic domains, predicted to represent the transmembrane spanning regions of the proteins. They are found in a wide range of organisms and are involved in the transmission of signals to the interior of cells as a result of their interaction with heterotrimeric G proteins. They respond to a diverse range of agents including lipid analogues, amino acid derivatives, small molecules such as epinephrine and dopamine, and various sensory stimuli. The properties of many known GPCR are summarized in S. Watson & S. Arkinstall, "The G-Protein Linked Receptor Facts Book" (Academic Press, London, 1994), incorporated herein by this reference. GPCR receptors include, but are not limited to, acetylcholine receptors, β-adrenergic receptors, β₃-adrenergic receptors, serotonin (5-hydroxytryptamine) receptors, dopamine receptors, adenosine receptors, angiotensin Type II receptors, bradykinin receptors, calcitonin receptors, calcitonin gene-related receptors, cannabinoid receptors, cholecystokinin receptors, chemokine receptors, cytokine receptors, gastrin receptors, endothelin receptors, γ-aminobutyric acid (GABA) receptors, galanin receptors, glucagon receptors, glutamate receptors, luteinizing hormone receptors, choriogonadotrophin receptors, follicle-stimulating hormone receptors, thyroid-stimulating hormone receptors, gonadotrophin-releasing hormone receptors, leukotriene receptors, Neuropeptide Y receptors, opioid receptors, parathyroid hormone receptors, platelet activating factor receptors, prostanoid (prostaglandin) receptors, somatostatin receptors, thyrotropin-releasing hormone receptors, vasopressin and oxytocin receptors.

When the improvement is made by analysis of patient or disease phenotype, the analysis of patient or disease phenotype can be, but is not limited to, a method of analysis of patient or disease phenotype carried out by a method selected from the group consisting of:
  (a) use of a diagnostic tool, a diagnostic technique, a diagnostic kit, or a diagnostic assay to confirm a patient's particular phenotype;
  (b) use of a method for measurement of a marker selected from the group consisting of histone deacetylase, ornithine decarboxylase, VEGF, a protein that is a gene product of a prostate specific gene, a protein that is a gene product of jun, a protein kinase, quantity or activity of MGMT, methylation of MGMT promoter, and mutant isocitrate dehydrogenase (IDH);
  (c) surrogate compound dosing; and
  (d) low dose pre-testing for enzymatic status.

The role of $O^6$-methylguanine DNA methyltransferase (MGMT) in human cancer has been described in M. Esteller & J. G. Herman, "Generating Mutations but Providing Chemosensitivity: The Role of $O^6$-Methylguanine DNA Methyltransferase in Human Cancer," *Oncology* 23: 1-8 (2004), incorporated herein by this reference. MGMT is a DNA repair protein that removes mutagenic and cytotoxic adducts from $O^6$-guanine in DNA. Alkylation of DNA at the $O^6$ position of guanine is an important step in the formation of mutations associated with malignancies, primarily due to the tendency of the $O^6$-methylguanine to pair with thymine during replication, resulting in the conversion of guanine-cytosine to adenine-thymine pairs (i.e., transversion mutations) in DNA. Furthermore, the $O^6$-alkylguanine-DNA adduct (especially the $O^6$-chloroethylguanine) may cross-link with the opposite cytosine residues, blocking DNA replication, which requires separation of the two nucleotide strands of the double helix. MGMT protects cells against these lesions, transferring the alkyl group from the $O^6$-guanine in DNA to an active cysteine within its own sequence in a reaction that inactivates one MGMT molecule for each lesion repaired. The alkylated MGMT protein then becomes detached from DNA and is targeted for degradation by ubiquitination, which marks the ubiquitinated protein for degradation. Accordingly, the ability of a cell to withstand such damage is directly related to the number of MGMT molecules that it contains and to the rate of de novo synthesis of MGMT in the cell.

Although MGMT can act at different rates on a wide variety of $O^6$-alkyl groups (and even in a minor degree on $O^4$-methylthymine which is an alkylation product of the pyrimidine thymine), the majority of studies have focused on the endogenous substrate $O^6$-methylguanine. Of the more than 12 different types of nitrogen and oxygen adducts of purine and pyrimidine bases produced by alkylating agents, $O^6$-methylguanine is, in fact, one of the least abundant, but of great importance in cancer biology. $O^6$-methylguanine affects cytosine methylation, the binding of transcription factors, recombinogenic capacity, and may inhibit DNA replication or cleavage if located at a replication origin or at a topoisomerase I site.

Amounts of MGMT protein in cells vary according to cellular type. In healthy cells, the level and activity of MGMT are regulated by protein phosphorylation status, binding of the E6 papillomavirus oncoprotein, and the action of the tumor suppressor p53, glucocorticoid hormone, and other transcription factors over its 5'-CpG island, which includes a classical promoter without TATA and CAAT boxes and a 59 by enhancer element located at the first exon-intron boundary. Mutations in the MGMT gene, including point mutations, have been described in association with esophageal cancer in Chinese patients (L. Wang et al., "Mutations of $O^6$-Methylguanine-DNA Methyltransferase Gene in Esophageal Cancer Tissues from Northern China," *Int. J. Cancer* 71: 719-723 (1997), incorporated herein by this reference), but the significance of these mutations is not established.

The MGMT protein is decreased in some tumors with respect to their normal tissue counterpart; a subset of tumor cell lines, termed Mer-, completely lack MGMT activity. However, in most cases, loss of expression is not commonly due to deletion, mutation or rearrangement of the MGMT gene or instability of mRNA transcribed from the MGMT gene, so it is believed that other causes for loss of MGMT activity are involved in the majority of cases where it occurs. Methylation of cytosine in CpG dinucleotides is the main epigenetic modification of DNA in normal mammalian cells. The human MGMT gene possesses a CpG island in the 5' portion of the gene. Hypermethylation of normally unmethylated CpG islands in the promoter regions of many genes, including $p16^{INK4a}$, $p14^{ARF}$, VHL, BRCA1, hMLH1 and E-cadherin, correlates with loss of transcription of the genes involved. Hypermethylation of the MGMT CpG island as the cause of MGMT transcriptional silencing in cell lines defective in $O^6$-methylguanine repair has been demonstrated. As for other genes inactivated by CpG island methylation, hypermethylation of the promoter region is accompanied by histone hypoacetylation and methylation, binding of specific methyl-binding proteins, and loss of normal nucleosome positioning. All of these alterations can result in a "closed" chromatin state that prevents gene transcription. It has also been shown that in vitro treatment of cancer cells with demethylation-inducing drugs restores MGMT expression.

Typically, in cancer, the loss of MGMT function is associated with hypermethylation of the promoter region in a wide spectrum of human tumors; these tumors include gliomas, lymphomas, colon, head and neck and non-small-cell lung carcinomas. This aberrant MGMT promoter methylation has been correlated with loss of MGMT protein, lack of mRNA expression, and loss of enzymatic activity. The promoter hypermethylation is considered to be an early event in carcinogenesis.

The causes of mutations in oncogenes and tumor suppressor genes are multifactorial. Exogenous and endogenous compounds are known to cause damage in DNA, including deletions, insertions and base substitutions, either transversions (change of purine to pyrimidine or vice versa) or transitions, change or purine to another purine or pyrimidine to another pyrimidine. A number of well-known reactions have been shown to generate point mutations. These reactions include: deamination of cytosine and 5-methylcytosine to uracil and thymine, respectively; depurination; DNA polymerase infidelity; and oxidative damage from endogenously produced free radicals. Other sources for mutations include abnormalities in DNA repair or replication. Several mechanisms can be invoked to contribute to the infidelity of DNA synthesis, including imbalances in deoxynucleotide triphosphate pools, mutations in DNA polymerase-α and slippage of DNA polymerase at nucleotide repeats.

In particular, one mutator pathway has been defined in human cancer. Germline mutations in the two DNA mismatch repair (MMR) genes hMLH1 and hMSH2 are the genetic abnormalities responsible for the vast majority of hereditary nonpolyposis colorectal carcinoma cases; in these cancers, the presence of deletions and insertions in microsatellite sequences is a common hallmark. However, in the nonfamilial cases, the presence of microsatellite instability is attributable to methylation-associated silencing of hMLH1 as indicated by the extremely tight association between both phenomena, the restoration of MMR activity using demethylating agents, and the early (premalignant) appearance of hMLH1 hypermethylation. The resulting epigenetic silencing of hMLH1 then leads to mutations in target genes such as BAX or TGFRβII.

Methylation-mediated silencing of MGMT causes another strong and important mutator pathway in human cancer; this mutator pathway is considered to be more prevalent than microsatellite instability. The persistence of $O^6$-methylguanine adducts, resulting from alkylating agents, may cause DNA polymerase to misread base pairing according to the normal Watson-Crick scheme because of the altered hydrogen-bonding properties of a base that contains an additional methyl or ethyl group. Thus, $O^6$-methylguanine is read as an adenine and mispairs with thymine. Supporting these data, the most common mutations caused by alkylating agents are G:C to A:T transitions exemplified in the frequent generation of G to A transitions in the oncogene K-ras when the carcinogen N-methylnitrosourea, a mutagen that forms $O^6$-methylguanine adducts, is used in experimentally induced tumor systems. The mutagenic effect is avoided if functional MGMT activity is present, and MGMT expression has been shown to protect mammalian cell lines from spontaneous G:C to A:T transitions in the aprt gene. MGMT inactivation is also strongly associated with K-ras mutations in human tumors. K-ras mutation is rare in human primary breast carcinomas, but occurs in approximately half of colorectal carcinomas. This mutation distribution strongly resembles the pattern of MGMT promoter hypermethylation described; while MGMT aberrant methylation is not present in breast carcinomas where K-ras mutations are extremely rare, it occurs in approximately 40% of cases of colorectal carcinomas associated with loss of MGMT expression, and is also frequent in non-small-cell lung carcinoma. Mutations that could be reversed by the activity of MGMT are also frequently found in the p53 gene; typically, these are again G:C to A:T transitions, and their occurrence is strongly associated with hypermethylation of the MGMT promoter; these mutations have been found in colon cancer, gliomas, and non-small-cell lung carcinomas.

However, a reduction in functional MGMT activity is also associated with increased sensitivity to alkylating agents, a number of which result in the generation of alkylation at the $O^6$ position of guanine. Thus, hypermethylation of the MGMT promoter can be associated with enhanced sensitivity of tumors with such hypermethylation to alkylating agents. However, there is no associated enhanced sensitivity for cisplatin, but there is for cyclophosphamide.

It is important to note that MGMT hypermethylation alone, without treatment with an alkylating agent, is not a good prognostic factor. In fact, it is a poor prognostic factor, probably due to the finding that patients with epigenetic silencing of MGMT accumulate more mutations in genes such as p53 and K-ras. This is an example of the difference between predictive and prognostic markers. Prognostic markers suggest a difference in outcome that is independent of the treatment received, including the possibility of no treatment. Predictive markers, on the other hand, predict a response, and thereby often survival differences, related to a specific form of therapy. Thus, while both types of markers can predict differences in survival, predictive markers potentially provide information leading to treatment decisions. MGMT methylation is definitively a negative prognostic marker, but a positive predictive marker. Therefore, an analysis of the existence or lack of hypermethylation of the MGMT promoter can be used in determination of chemotherapeutic strategies. It is also possible to promote sensitivity of tumors to alkylating agents by administration of the MGMT inhibitor $O^6$-benzylguanine.

U.S. Pat. No. 9,050,280 to Vlassenbroeck et al., incorporated herein by this reference, discloses a method of detecting the presence and/or amount of a methylated or unmethylated gene of interest in a DNA-containing sample that comprises the steps of: (i) contacting the DNA-containing sample with a reagent which selectively modifies unmethylated cytosine residues in the DNA to produce detectable modified residues but which does not modify methylated cytosine residues; (ii) amplifying at least a portion of the methylated or unmethylated gene of interest using at least one primer pair, at least one primer of which is designed to bind only to the sequence of methylated or unmethylated DNA following treatment with the reagent, wherein at least one primer in the primer pair produces a detectable fluorescence signal during amplification which is detected in real-time; and (iii) quantifying the results of the real-time detection against a standard curve for the methylated or unmethylated gene of interest to produce an output of gene copy number. Preferred reagents that selectively modify unmethylated cytosine residues in the DNA to produce detectable modified residues but which do not modify methylated cytosine residues include bisulfites, such as sodium bisulfite. The method can employ fluorescence resonance energy transfer (FRET) for detection. This method can be used for determination of the methylation status of the MGMT promoter.

United States Patent Application Publication No. 2007/0264672 by Dasmahapatra et al., incorporated herein by this reference, discloses methods for assaying MGMT activity, including an immunoassay method, a method employing labeled $O^6$-benzylguanine, and a fluorescence polarization method.

Isocitrate dehydrogenase (IDH) is an enzyme that normally catalyzes the oxidative decarboxylation of isocitrate, producing α-ketoglutarate and $CO_2$. This is a two-step process, which involves oxidation of isocitrate (a secondary alcohol) to oxalosuccinate (a ketone), followed by the decarboxylation of the carboxyl group β to the ketone, forming α-ketoglutarate. In humans, IDH exists in three isoforms: IDH3 catalyzes the third step of the citric acid cycle while converting NAD⁺ to NADH in the mitochondria. The isoforms IDH1 and IDH2 catalyze the same reaction outside the context of the citric acid cycle and use NADP⁺ as a cofactor instead of NAD⁺. They localize to the cytosol as well as the mitochondrion and peroxisome. In the context of cancer therapy, the significant isoforms are IDH1 and IDH2, especially IDH1. Specific mutations in the isocitrate dehydrogenase gene IDH1 have been found in several brain tumors including astrocytoma, oligodendroglioma, and glioblastoma multiforme, with mutations found in nearly all cases of secondary glioblastomas, which develop from lower-grade gliomas, but rarely in primary high-grade glioblastoma multiforme (F. E. Bleeker et al., "Recent Advances in the Molecular Understanding of Glioblastoma," *J. Neurooncol.* 108: 11-27 (2012), incorporated herein by this reference). Patients whose tumor had an IDH1 mutation had longer survival. Furthermore, mutations of IDH2 and IDH1 were found in up to 20% of cytogenetically normal acute myeloid leukemia (AML) (P. S. Ward et al., "The Common Feature of Leukemia-Associated IDH1 and IDH2 Mutations is a Neomorphic Enzyme Activity Converting α-Ketoglutarate to 2-Hydroxyglutarate," *Cancer Cell* 17: 225-234 (2010), incorporated herein by this reference). These mutations are known to produce (D)-2-hydroxyglutarate, an abnormal product, from α-ketoglutarate. (D)-2-hydroxyglutarate can then accumulate to very high concentrations, which inhibits the function of enzymes that are dependent on α-ketoglutarate. This leads to a hypermethylated state of DNA and histones, which results in different gene expression that can activate oncogenes and inactivate tumor-suppressor genes. Ultimately, this may lead to the types of cancer described above (R. J. Molenaar et al., "The Driver and Passenger Effects of Isocitrate Dehydrogenase 1 and 2 Mutations in Oncogenesis and Survival Prolongation," *Biochim. Biophys. Acta* 1846: 326-341 (2014), incorporated herein by this reference).

U.S. Pat. No. 8,883,438 to Cantley et al., incorporated herein by this reference, discloses methods of diagnosing a subject having a cell proliferation-related disorder or suspected of having a cell proliferation-related disorder characterized by: (i) the presence, distribution, or level of an isocitrate dehydrogenase 1 enzyme having a mutation at residue 97 wherein the glycine residue has been replaced with an aspartic acid residue (IDH1-G97D), which has 2-hydroxyglutarate (2HG) neoactivity, wherein 2HG neoactivity is the ability to convert α-ketoglutarate to 2-hydroxyglutarate, or (ii) elevated levels of 2HG due to the presence of IDH1-G97D mutant enzyme having 2HG neoactivity, wherein the method comprises analyzing the presence, distribution, or level of 2HG in a tissue, product, or bodily fluid of said subject by a chromatographic method, wherein an increased presence, distribution, or level of 2HG indicates the presence of the cell proliferation-related disorder, thereby diagnosing the subject for the cell proliferation-related disorder. The chromatographic method can be LC-MS or GC-MS. Alternatively, a mutation can be an IDH2-137 mutation. A method for treating a malignancy characterized by a mutation in IDH can include administration of a cellular structural analog of an α-hydroxy neoactivity product of Formula (S-II):

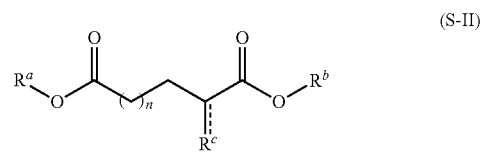

wherein: (i) each $R^a$ and $R^b$ is independently hydrogen, a metal ion, or a negative charge; (ii) $R^c$ is a hydrogen bond donor or acceptor, and can be bound to the carbon chain by a single or double bond, as indicated by the dashed line; and (iii) n is 0, 1, or 2. Alternatively, an inhibitor of the neoactivity can be administered.

U.S. Pat. No. 8,685,660 to Vogelstein et al., incorporated herein by this reference, discloses clinically significant mutations in IDH1 and IDH2, including: R132H in IDH1, R132S in IDH1, R132C in IDH1, R132L in IDH1, R132G in IDH1, R172M in IDH2, R172K in IDH2, and R172G in IDH2.

When the improvement is made by analysis of patient or disease genotype, the analysis of patient or disease genotype can be, but is not limited to, a method of analysis of patient or disease genotype carried out by a method selected from the group consisting of:
  (a) use of a diagnostic tool, a diagnostic technique, a diagnostic kit, or a diagnostic assay to confirm a patient's particular genotype;
  (b) use of a gene chip;
  (c) use of gene expression analysis;
  (d) use of single nucleotide polymorphism (SNP) analysis; and
  (e) measurement of the level of a metabolite or a metabolic enzyme.

The use of gene chips is described in A. J. Lee & S. Ramaswamy, "DNA Microarrays in Biological Discovery and Patient Care" in *Essentials of Genomic and Personalized Medicine* (G. S. Ginsburg & H. F. Willard, eds., Academic Press, Amsterdam, 2010), ch. 7, pp. 73-88, incorporated herein by this reference.

When the method is the use of single nucleotide polymorphism (SNP) analysis, the SNP analysis can be carried out on a gene selected from the group consisting of histone deacetylase, ornithine decarboxylase, VEGF, a prostate specific gene, c-Jun, and a protein kinase. The use of SNP analysis is described in S. Levy and Y.-H. Rogers, "DNA Sequencing for the Detection of Human Genome Variation" in *Essentials of Genomic and Personalized Medicine* (G. S. Ginsburg & H. F. Willard, eds., Academic Press, Amsterdam, 2010), ch. 3, pp. 27-37, incorporated herein by this reference.

Still other genomic techniques such as copy number variation analysis and analysis of DNA methylation can be employed. Copy number variation analysis is described in C. Lee et al., "Copy Number Variation and Human Health" in *Essentials of Genomic and Personalized Medicine* (G. S. Ginsburg & H. F. Willard, eds., Academic Press, Amsterdam, 2010), ch. 5, pp. 46-59, incorporated herein by this reference. DNA methylation analysis is described in S. Cottrell et al., "DNA Methylation Analysis: Providing New Insight into Human Disease" in *Essentials of Genomic and Personalized Medicine* (G. S. Ginsburg & H. F. Willard, eds., Academic Press, Amsterdam, 2010), ch. 6, pp. 60-72, incorporated herein by this reference.

When the improvement is made by pre/post-treatment preparation, the pre/post-treatment preparation can be, but is not limited to, a method of pre/post treatment preparation selected from the group consisting of:
(a) the use of colchicine or an analog thereof;
(b) the use of a uricosuric;
(c) the use of uricase;
(d) the non-oral use of nicotinamide;
(e) the use of a sustained-release form of nicotinamide;
(f) the use of an inhibitor of poly-ADP ribose polymerase;
(g) the use of caffeine;
(h) the use of leucovorin rescue;
(i) infection control; and
(j) the use of an anti-hypertensive agent.

Uricosurics include, but are not limited to, probenecid, benzbromarone, and sulfinpyrazone. A particularly preferred uricosuric is probenecid. Uricosurics, including probenecid, may also have diuretic activity.

Poly-ADP ribose polymerase inhibitors are described in G. J. Southan & C. Szabó, "Poly(ADP-Ribose) Inhibitors," *Curr. Med. Chem.* 10: 321-240 (2003), incorporated herein by this reference, and include nicotinamide, 3-aminobenzamide, substituted 3,4-dihydroisoquinolin-1(2H)-ones and isoquinolin-1(2H)-ones, benzimidazoles, indoles, phthalazin-1(2H)-ones, quinazolinones, isoindolinones, phenanthridinones, and other compounds.

Leucovorin rescue comprises administration of folinic acid (leucovorin) to patients in which methotrexate has been administered. Leucovorin is a reduced form of folic acid that bypasses dihydrofolate reductase and restores hematopoietic function. Leucovorin can be administered either intravenously or orally.

In one alternative, wherein the pre/post treatment is the use of a uricosuric, the uricosuric is probenecid or an analog thereof.

When the improvement is made by toxicity management, the toxicity management can be, but is not limited to, a method of toxicity management selected from the group consisting of:
(a) the use of colchicine or an analog thereof;
(b) the use of a uricosuric;
(c) the use of uricase;
(d) the non-oral use of nicotinamide;
(e) the use of a sustained-release form of nicotinamide;
(f) the use of an inhibitor of poly-ADP ribose polymerase;
(g) the use of caffeine;
(h) the use of leucovorin rescue;
(i) the use of sustained-release allopurinol;
(j) the non-oral use of allopurinol;
(k) the use of bone marrow transplants;
(l) the use of a blood cell stimulant;
(m) the use of blood or platelet infusions;
(n) the administration of an agent selected from the group consisting of filgrastim (Neupogen®), G-CSF, and GM-CSF;
(o) the application of a pain management technique;
(p) the administration of an anti-inflammatory agent;
(q) the administration of fluids;
(r) the administration of a corticosteroid;
(s) the administration of an insulin control medication;
(t) the administration of an antipyretic;
(u) the administration of an anti-nausea treatment;
(v) the administration of an anti-diarrheal treatment;
(w) the administration of N-acetylcysteine; and
(x) the administration of an antihistamine.

Filgrastim is a granulocytic colony-stimulating factor (G-CSF) analog produced by recombinant DNA technology that is used to stimulate the proliferation and differentiation of granulocytes and is used to treat neutropenia; G-CSF can be used in a similar manner. GM-CSF is granulocyte macrophage colony-stimulating factor and stimulates stem cells to produce granulocytes (eosinophils, neutrophils, and basophils) and monocytes; its administration is useful to prevent or treat infection.

Anti-inflammatory agents are well known in the art and include corticosteroids and non-steroidal anti-inflammatory agents (NSAIDs). Corticosteroids with anti-inflammatory activity include, but are not limited to, hydrocortisone, cortisone, beclomethasone dipropionate, betamethasone, dexamethasone, prednisone, methylprednisolone, triamcinolone, fluocinolone acetonide, and fludrocortisone. Nonsteroidal anti-inflammatory agents include, but are not limited to, acetylsalicylic acid (aspirin), sodium salicylate, choline magnesium trisalicylate, salsalate, diflunisal, sulfasalazine, olsalazine, acetaminophen, indomethacin, sulindac, tolmetin, diclofenac, ketorolac, ibuprofen, naproxen, flurbiprofen, ketoprofen, fenoprofin, oxaprozin, mefenamic acid, meclofenamic acid, piroxicam, meloxicam, nabumetone, rofecoxib, celecoxib, etodolac, nimesulide, aceclofenac, alclofenac, alminoprofen, amfenac, ampiroxicam, apazone, araprofen, azapropazone, bendazac, benoxaprofen, benzydamine, bermoprofen, benzpiperylon, bromfenac, bucloxic acid, bumadizone, butibufen, carprofen, cimicoxib, cinmetacin, cinnoxicam, clidanac, clofezone, clonixin, clopirac, darbufelone, deracoxib, droxicam, eltenac, enfenamic acid, epirizole, esflurbiprofen, ethenzamide, etofenamate, etoricoxib, felbinac, fenbufen, fenclofenac, fenclozic acid, fenclozine, fendosal, fentiazac, feprazone, filenadol, flobufen, florifenine, flosulide, flubichin methanesulfonate, flufenamic acid, flufenisal, flunixin, flunoxaprofen, fluprofen, fluproquazone, furofenac, ibufenac, imrecoxib, indoprofen, isofezolac, isoxepac, isoxicam, licofelone, lobuprofen, lomoxicam, lonazolac, loxaprofen, lumaricoxib, mabuprofen, miroprofen, mofebutazone, mofezolac, morazone, nepafanac, niflumic acid, nitrofenac, nitroflurbiprofen, nitronaproxen, orpanoxin, oxaceprol, oxindanac, oxpinac, oxyphenbutazone, pamicogrel, parcetasal, parecoxib, parsalmide, pelubiprofen, pemedolac, phenylbutazone, pirazolac, pirprofen, pranoprofen, salicin, salicylamide, salicylsalicylic acid, satigrel, sudoxicam, suprofen, talmetacin, talniflumate, tazofelone, tebufelone, tenidap, tenoxicam, tepoxalin, tiaprofenic acid, tiaramide, tilmacoxib, tinoridine, tiopinac, tioxaprofen, tolfenamic acid, triflusal, tropesin, ursolic acid, valdecoxib, ximoprofen, zaltoprofen, zidometacin, and zomepirac, and the salts, solvates, analogues, congeners, bioisosteres, hydrolysis products, metabolites, precursors, and prodrugs thereof.

The clinical use of corticosteroids is described in B. P. Schimmer & K. L. Parker, "Adrenocorticotropic Hormone; Adrenocortical Steroids and Their Synthetic Analogs; Inhibitors of the Synthesis and Actions of Adrenocortical Hormones" in *Goodman & Gilman's The Pharmacological Basis of Therapeutics* (L. L. Brunton, ed., 11$^{th}$ ed., McGraw-Hill, New York, 2006), ch. 59, pp. 1587-1612, incorporated herein by this reference.

Anti-nausea treatments include, but are not limited to, ondansetron, metoclopramide, promethazine, cyclizine, hyoscine, dronabinol, dimenhydrinate, diphenhydramine, hydroxyzine, medizine, dolasetron, granisetron, palonosetron, ramosetron, domperidone, haloperidol, chlorpromazine, fluphenazine, perphenazine, prochlorperazine, betamethasone, dexamethasone, lorazepam, and thiethylperazine.

Anti-diarrheal treatments include, but are not limited to, diphenoxylate, difenoxin, loperamide, codeine, racecadotril, octreoside, and berberine.

N-acetylcysteine is an antioxidant and mucolytic that also provides biologically accessible sulfur.

When the improvement is made by pharmacokinetic/pharmacodynamic monitoring, the pharmacokinetic/pharmacodynamic monitoring can be, but is not limited to a method selected from the group consisting of:
(a) multiple determinations of blood plasma levels; and
(b) multiple determinations of at least one metabolite in blood or urine.

Typically, determination of blood plasma levels or determination of at least one metabolite in blood or urine is carried out by immunoassays. Methods for performing immunoassays are well known in the art, and include radioimmunoassay, ELISA (enzyme-linked immunosorbent assay), competitive immunoassay, immunoassay employing lateral flow test strips, and other assay methods.

When the improvement is made by drug combination, the drug combination can be, but is not limited to, a drug combination selected from the group consisting of:
(a) use with topoisomerase inhibitors;
(b) use with fraudulent nucleosides;
(c) use with fraudulent nucleotides;
(d) use with thymidylate synthetase inhibitors;
(e) use with signal transduction inhibitors;
(f) use with cisplatin or platinum analogs;
(g) use with alkylating agents;
(h) use with anti-tubulin agents;
(i) use with antimetabolites;
(j) use with berberine;
(k) use with apigenin;
(l) use with amonafide;
(m) use with vinca alkaloids;
(n) use with 5-fluorouracil;
(o) use with curcumin;
(p) use with NF-κB inhibitors;
(q) use with rosmarinic acid;
(r) use with mitoguazone;
(s) use with tetrandrine;
(t) use with an inhibitor of mutant isocitrate dehydrogenase (IDH);
(u) use with a MGMT inhibitor; and
(v) use with an agent that inhibits NF-κB-enhanced expression of MGMT.

Topoisomerase inhibitors include, but are not limited to, irinotecan, topotecan, camptothecin, lamellarin D, amsacrine, etoposide, etoposide phosphate, teniposide, doxorubicin, and ICRF-193.

Fraudulent nucleosides include, but are not limited to, cytosine arabinoside, gemcitabine, and fludarabine; other fraudulent nucleosides are known in the art.

Fraudulent nucleotides include, but are not limited to, tenofovir disoproxil fumarate and adefovir dipivoxil; other fraudulent nucleotides are known in the art.

Thymidylate synthetase inhibitors include, but are not limited to, raltitrexed, pemetrexed, nolatrexed, ZD9331, GS7094L, fluorouracil, and BGC 945.

Signal transduction inhibitors are described in A. V. Lee et al., "New Mechanisms of Signal Transduction Inhibitor Action: Receptor Tyrosine Kinase Down-Regulation and Blockade of Signal Transactivation," *Clin. Cancer Res.* 9: 516s (2003), incorporated herein in its entirety by this reference.

Alkylating agents include, but are not limited to, Shionogi 254-S, aldo-phosphamide analogues, altretamine, anaxirone, Boehringer Mannheim BBR-2207, bendamustine, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, melphalan, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin and trimelamol, as described in U.S. Pat. No. 7,446,122 by Chao et al., incorporated herein by this reference.

Anti-tubulin agents include, but are not limited to, vinca alkaloids, taxanes, podophyllotoxin, halichondrin B, and homohalichondrin B.

Antimetabolites include, but are not limited to: methotrexate, pemetrexed, 5-fluorouracil, capecitabine, cytarabine, gemcitabine, 6-mercaptopurine, and pentostatin, alanosine, AG2037 (Pfizer), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrill-Dow DDFC, deazaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

Berberine has antibiotic activity and prevents and suppresses the expression of pro-inflammatory cytokines and E-selectin, as well as increasing adiponectin expression.

Apigenin is a flavone that can reverse the adverse effects of cyclosporine and has chemoprotective activity, either alone or derivatized with a sugar.

Amonafide is a topoisomerase inhibitor and DNA intercalator that has anti-neoplastic activity.

Curcumin is believed to have anti-neoplastic, anti-inflammatory, antioxidant, anti-ischemic, anti-arthritic, and anti-amyloid properties and also has hepatoprotective activity.

NF-κB inhibitors include, but are not limited to, bortezomib.

Rosmarinic acid is a naturally-occurring phenolic antioxidant that also has anti-inflammatory activity.

Mitoguazone is an inhibitor of polyamine biosynthesis through competitive inhibition of S-adenosylmethionine decarboxylase.

Tetrandrine has the chemical structure 6,6',7,12-tetramethoxy-2,2'-dimethyl-1 β-berbaman and is a calcium channel blocker that has anti-inflammatory, immunologic, and antiallergenic effects, as well as an anti-arrhythmic effect similar to that of quinidine. It has been isolated from *Stephania tetranda* and other Asian herbs.

In one alternative, when the drug combination is use with an alkylating agent, the alkylating agent can be selected from the group consisting of BCNU, BCNU wafers (Gliadel), and CCNU.

Inhibitors of mutant isocitrate dehydrogenase (IDH) are known in the art.

U.S. Pat. No. 8,957,068 to Caferro et al., incorporated herein by this reference, discloses 3-pyrimidin-4-yl-oxazolidin-2-ones as inhibitors of mutant IDH, including compounds of Formula (S-I):

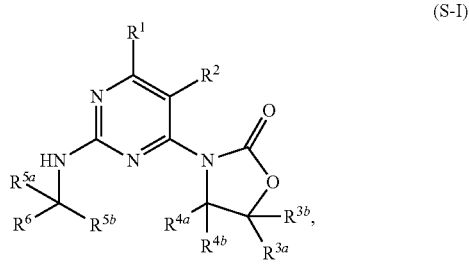

(S-I)

wherein:
(i) $R^1$ and $R^2$ are each independently hydrogen, deuterium, halo, hydroxyl, $NH_2$, aryl, heteroaryl, or optionally substituted $C_1$-$C_4$ alkyl, wherein $C_1$-$C_4$ alkyl is optionally substituted with one to three substituents each independently selected from the group consisting of: halo, hydroxyl, and $NH_2$;
(ii) $R^{3a}$ is hydrogen, deuterium, $C_1$-$C_6$ alkyl, phenyl, or benzyl;
(iii) $R^{3b}$ is hydrogen, deuterium, $C_1$-$C_6$ alkyl; or $R^{3a}$ and $R^{3b}$ are joined together forming an optionally substituted 3-7 membered cycloalkyl ring or an optionally substituted 4-7 membered heterocyclic ring, wherein said cycloalkyl and heterocyclic rings are each optionally substituted with one or two substituents each independently selected from the group consisting of: halo, hydroxyl, oxo, $NH_2$, and $C_1$-$C_3$ alkyl;
(iv) $R^{4a}$ is hydrogen, $C_1$-$C_6$ alkyl, optionally substituted phenyl, optionally substituted benzyl, optionally substituted heteroaryl, or methylene-dibenzene, wherein said phenyl, benzyl, and heteroaryl rings are optionally substituted with one to three substituents each independently selected from the group consisting of: halo, hydroxyl, cyano, nitro, $C_1$-$C_4$ alkoxy, $C_1$-$C_3$ haloalkyl, $C_1$-$C_3$ haloalkoxy, $C_1$-$C_6$ alkyl, $C_3$-$C_6$ cycloalkyl, phenyl, 5-6 membered heteroaryl, 5-6 membered heterocyclic, phenoxy, —$COOR^b$, —$SO_2R^b$, —$NHC(O)R^b$, and —$NR^bR^b$;
(v) $R^{4b}$ is hydrogen, deuterium, or $C_1$-$C_3$ alkyl, or $R^{4a}$ and $R^{4b}$ are joined together forming an optionally substituted 3-7 membered cycloalkyl ring or an optionally substituted 4-7 membered heterocyclic ring, wherein said cycloalkyl and heterocyclic rings are optionally substituted with one or two substituents each independently selected from the group consisting of: halo, hydroxyl, oxo, $NH_2$, and $C_1$-$C_3$ alkyl, provided that only one of $R^{3a}$ and $R^{3b}$ and $R^{4a}$ and $R^{4b}$ are joined together forming a ring;
(vi) $R^{5a}$ is hydrogen or deuterium;
(vii) $R^{5b}$ is hydrogen, deuterium, methyl, ethyl, $CD_3$, $CF_3$, $CH_2F$, or $CHF_2$ and
(viii) $R^6$ is optionally substituted $C_1$-$C_6$ alkyl, optionally substituted aryl, optionally substituted heteroaryl, optionally substituted heterocyclyl, or optionally substituted $C_3$-$C_{10}$ cycloalkyl;
(viii) wherein said $C_1$-$C_6$ alkyl is optionally substituted with one substituent selected from the group consisting of hydroxyl, $C_1$-$C_3$ alkoxy and —$OR^a$;

(ix) wherein said aryl, heteroaryl, heterocyclic and $C_3$-$C_{10}$ cycloalkyl are optionally substituted with one to three substituents each independently selected from the group consisting of: halo; hydroxyl; cyano; nitro; $C_1$-$C_4$ alkoxy; $C_1$-$C_3$ haloalkyl; $C_1$-$C_3$ haloalkoxy; $C_1$-$C_6$ alkyl; $C_3$-$C_6$ cycloalkyl optionally substituted with one to three substituents each independently selected from the group consisting of: hydroxyl, cyano, $C_1$-$C_3$ alkyl, $C_1$-$C_3$ alkoxy, and $C_1$-$C_3$ haloalkyl; phenyl optionally substituted with one to three substituents each independently selected from the group consisting of: halo, hydroxyl, cyano, nitro, $C_1$-$C_3$ alkoxy, $C_1$-$C_3$ haloalkyl, $C_1$-$C_3$ haloalkoxy, $C_1$-$C_6$ alkyl, $C_3$-$C_6$ cycloalkyl, 5-6 membered heteroaryl, 5-6 membered heterocyclic, phenoxy, —$COOR^b$, —$SO_2R^b$, —$NHC(O)R^b$, and —$NR^bR^b$; 5-6 membered heteroaryl optionally substituted with one to three substituents each independently selected from the group consisting of: halo, hydroxyl, cyano, $C_1$-$C_3$ alkyl, $C_1$-$C_3$ alkoxy; 5-6 membered heterocyclyl optionally substituted with one to three substituents each independently selected from the group consisting of: halo, hydroxyl, oxo, $NH_2$, and $C_1$-$C_3$ alkyl; —$CH_2R^a$; —$OR^a$; —$C(O)R^a$; —$NR^aR^b$; —$COOR^a$; —$SO_2R^a$; —$SO_2R^b$; $NHC(O)R^a$; —$NHC(O)R^b$; —$C(O)NR^aR^b$; —$C(O)NHR^b$; and —$SO^2NR^bR^b$; or (x) $R^{5b}$ and $R^6$ are joined together forming an optionally substituted $C_3$-$C_7$ cycloalkyl group or an optionally substituted group of Formula (S-I(a)):

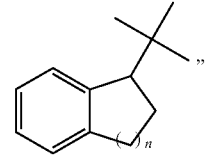

(S-I(a))

wherein n is 1, 2, or 3; and
(xii) said $C_3$-$C_7$ cycloalkyl and group of formula (a) are optionally substituted with one to three substituents each independently selected from the group consisting of: halo, hydroxyl, cyano, nitro, $C_1$-$C_3$ alkoxy, $C_1$-$C_3$ haloalkyl, $C_1$-$C_3$ haloalkoxy, $C_1$-$C_6$ alkyl, $C_3$-$C_6$ cycloalkyl, 5-6 membered heteroaryl, 5-6 membered heterocyclyl, benzyloxy, —$COOR^b$, —$SO_2R^b$, —$NHC(O)R^b$, and —$NR^bR^b$;
(xiii) each $R^a$ is independently optionally substituted phenyl, optionally substituted heteroaryl, optionally substituted heterocyclic, or optionally substituted $C_3$-$C_7$ cycloalkyl,
(xiv) wherein said phenyl and heteroaryl are optionally substituted with one to three substituents each independently selected from the group consisting of halo, hydroxyl, cyano, nitro, $C_1$-$C_3$ alkoxy, $C_1$-$C_3$ haloalkyl, $C_1$-$C_3$ haloalkoxy, and $C_1$-$C_3$ alkyl,
(xv) wherein said heterocyclic is optionally substituted with one to three substituents each independently selected from the group consisting of halo, hydroxyl, oxo, $C_1$-$C_3$ alkoxy, $C_1$-$C_3$ haloalkyl, $C_1$-$C_3$ haloalkoxy, $C_1$-$C_4$ alkyl, $C_3$-$C_5$ cycloalkyl, —$C(O)R^b$, and —$NR^bR^b$; and
(xvi) wherein said $C_3$-$C_7$ cycloalkyl is optionally substituted with one to three substituents each independently selected from the group consisting of halo, hydroxyl, oxo, $C_1$-$C_3$ alkoxy, $C_1$-$C_3$ haloalkyl, $C_1$-$C_3$ haloalkoxy, and $C_1$-$C_3$ alkyl; and (xvii) each $R^b$ is independently hydrogen or $C_1$-$C_6$ alkyl.

U.S. Pat. No. 8,883,438 to Cantley et al., incorporated herein by this reference, discloses methods of diagnosing a subject having a cell proliferation-related disorder or suspected of having a cell proliferation-related disorder characterized by: (i) the presence, distribution, or level of an isocitrate dehydrogenase 1 enzyme having a mutation at residue 97 wherein the glycine residue has been replaced with an aspartic acid residue (IDH1-G97D), which has 2-hydroxyglutarate (2HG) neoactivity, wherein 2HG neoactivity is the ability to convert α-ketoglutarate to 2-hydroxyglutarate, or (ii) elevated levels of 2HG due to the presence of IDH1-G97D mutant enzyme having 2HG neoactivity, wherein the method comprises analyzing the presence, distribution, or level of 2HG in a tissue, product, or bodily fluid of said subject by a chromatographic method, wherein an increased presence, distribution, or level of 2HG indicates the presence of the cell proliferation-related disorder, thereby diagnosing the subject for the cell proliferation-related disorder. The chromatographic method can be LC-MS or GC-MS. Alternatively, a mutation can be an IDH2-137 mutation. A method for treating a malignancy characterized by a mutation in IDH can include administration of a cellular structural analog of an α-hydroxy neoactivity product of Formula (S-II):

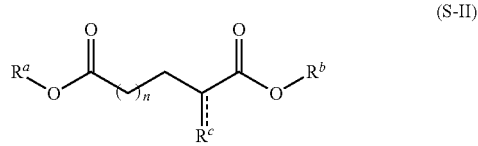

(S-II)

wherein: (i) each $R^a$ and $R^b$ is independently hydrogen, a metal ion, or a negative charge; (ii) $R^c$ is a hydrogen bond donor or acceptor, and can be bound to the carbon chain by a single or double bond, as indicated by the dashed line; and (iii) n is 0, 1, or 2. Alternatively, an inhibitor of the neoactivity can be administered.

United States Patent Application Publication No. 2014/0100223 by Hussain et al., incorporated herein by this reference, discloses compounds and methods for the treatment of isocitrate-dehydrogenase-related diseases, including compounds of Formula (S-III):

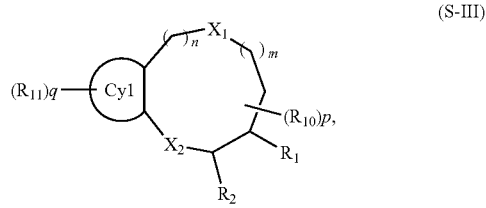

(S-III)

wherein:
(i) each n and m is independently 0, 1, 2 or 3;
(ii) each p and q is independently 0, 1, 2, 3, 4, 5, 6 or 7;
(iii) $X_1$ is —C(O)N($R_A$)— or —C(S)N($R_A$)—, wherein $R_A$ is independently hydrogen, aliphatic, substituted aliphatic, heteroaryl, substituted heteroaryl, aryl or substituted aryl;

(iv) $X_2$ is —S— —O—, —S(O)$_2$— —C($R_{20}$)($R_{21}$)— or —N($R_B$)—, wherein $R_B$ is independently hydrogen, aliphatic, substituted aliphatic, heteroaryl, substituted heteroaryl, aryl or substituted aryl;

(v) each $R_1$ and $R_2$ is independently hydrogen, halogen, aliphatic, substituted aliphatic, aryl or substituted aryl;

(vi) $R_3$ is hydrogen, halogen, aliphatic, substituted aliphatic, aryl or substituted aryl;

(vii) each $R_{10}$, and $R_{28}$ is independently absent, hydrogen, halogen, —O$R_{20}$, —S$R_{20}$, —N$R_{20}R_{21}$, —CF$_3$, —CN, —NO$_2$, —N$_3$, —C(O)O$R_{20}$, —C(O)$R_{20}$, —C(O)N$R_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl, or alternatively two of $R_{10}$ groups together with the atoms to which they are attached and any intervening atoms may form an additional optionally substituted, 3, 4, 5, 6 or 7 membered ring, wherein each $R_{20}$ and $R_{21}$ is independently hydrogen, halogen, aliphatic, substituted aliphatic, aryl or substituted aryl;

(viii) each $R_{11}$ is independently absent, hydrogen, halogen, —O$R_{20}$, —S$R_{20}$, —N$R_{20}R_{21}$, —CF$_3$, —CN, —NO$_2$, —N$_3$, —C(O)$R_{20}$, —C(O)O$R_{20}$, —C(O)N$R_{20}R_{21}$, acyl, alkoxy, substituted alkoxy, alkylamino, substituted alkylamino, dialkylamino, substituted dialkylamino, substituted or unsubstituted alkylthio, substituted or unsubstituted alkylsulfonyl, aliphatic, substituted aliphatic, aryl or substituted aryl, or alternatively two of $R_{11}$ groups together with the atoms to which they are attached and any intervening atoms may form an additional optionally substituted, 3, 4, 5, 6 or 7 membered ring; and (ix) Cyl is an optionally substituted aryl or optionally substituted heteroaryl.

United States Patent Application Publication No. 2014/0094503 by Ma et al., incorporated herein by this reference, discloses RNA-interference-mediated interference with expression of IDH1, including interference mediated by small nucleic acid molecules such as short interfering nucleic acid (siNA), short interfering RNA (sRNA), double-stranded RNA (dsRNA), micro-RNA (miRNA), and short hairpin RNA (shRNA) molecules.

United States Patent Application Publication No. 2013/0109643 by Riggins et al., incorporated herein by this reference, discloses methods for treating various forms of cancer, including a malignant low-grade glioma, a secondary glioblastoma, a transforming myeloproliferative disorder (tMPD), and an acute myelogenous leukemia (AML), with glutaminase inhibitors, including, but not limited to:

(A) glutaminase inhibitors of Formula (S-IV):

(I)

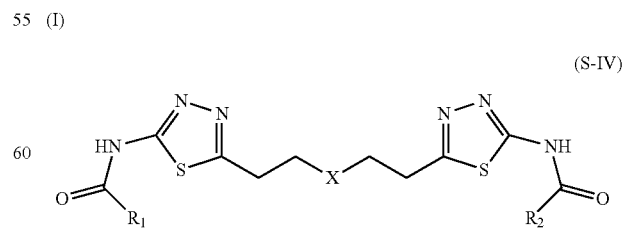

(S-IV)

wherein X is sulfur or oxygen; $R_1$ and $R_2$ are independently selected from the group consisting of lower alkyl, lower alkoxyl, aryl, thiophenyl and —(CH$_2$)$_n$-aryl; wherein n is 0 or 1, and aryl is a monocyclic aromatic or heteroaromatic group, having ring atoms selected from the group consisting of carbon, nitrogen, oxygen, and sulfur, and having at most three non-carbon ring atoms, which group may be unsubstituted or substituted with one or more substituents selected from the group consisting of halogen, lower alkyl, lower alkoxyl, amino, lower alkyl amino, amino(lower alkyl), or halo(lower alkyl); and (B) a compound selected from the group consisting of 6-diazo-5-oxo-L-norleucine, acivicin, N-ethylmaleimide, p-chloromercuriphenylsulfonate, L-2-amino-4-oxo-5-chloropentoic acid, azaserine, and 5-(3-bromo-4-(dimethylamino)phenyl)-2,2-dimethyl-2,3,5,6-tetrahydrobenzo[a]phenanthridin-4(1H)-one; and pharmaceutically acceptable salts thereof; a particularly preferred compound is bis-2-(5-phenylacetamido-1,2,4-thiadiazol-2-yl)ethyl sulfide.

MGMT inhibitors are known in the art.

U.S. Pat. No. 8,791,081 to Liu et al., incorporated herein by this reference, discloses the use of MGMT inhibitors for the treatment of neoplastic disorders. The MGMT inhibitors can include, but are not limited to, $O^6$-substituted guanine derivatives or glucose conjugates thereof. Suitable MGMT inhibitors include $O^6$-benzylguanine, $O^6$-2-fluoropyridinylmethyl guanine, $O^6$-3-iodobenzyl guanine, $O^6$-4-bromophenylguanine, $O^6$-5-iodothenylguanine, $O^6$-benzyl-8-oxoguanine, $O^6$-(p-chlorobenzyl)guanine, $O^6$-(p-methylbenzyl) guanine, $O^6$-(p-bromobenzyl)guanine, $O^6$-(p-isopropylbenzyl)guanine, $O^6$-(3,5-dimethylbenzyl)guanine, $O^6$-(p-n-butylbenzyl)guanine, $O^6$-(p-hydroxymethybenzyl) guanine, $O^6$-benzylhypoxanthine, $N^2$-acetyl-$O^6$-benzylguanine, $N^2$-acetyl-$O^6$-benzyl-8-oxo-guanine, 2-amino-6-(p-methyl-benzyl-thio)purine, 2-amino-6-(benzyloxy)-9-[(ethoxycarbonyl)methyl]purine, 2-amino-6-(benzyloxy)-9-(pivaloyloxymethyl)purine, 2-amino-6-(benzyl-thio)purine, $O^6$-benzyl-7,8-dihydro-8-oxoguanine, 2,4,5-triamino-6-benzyloxyprimidine, $O^6$-benzyl-9-[(3-oxo-5α-androstan-17β-yloxycarbonyl)methyl]guanine, $O^6$-benzyl-9-[(3-oxo-4-androsten-17β-yloxycarbonyl)methylguanine], and 8-amino-$O^6$-benzylguanine, as well as C8-linker-glucose-conjugates thereof.

Inhibitors of NF-κB-enhanced expression of MGMT are known in the art.

U.S. Pat. No. 8,299,237 to Lavon, incorporated herein by this reference, discloses nucleic acid sequences and modified nucleotides comprising NF-κB binding sites within the MGMT promoter region that are useful as decoy molecules for inhibiting NF-κB-enhanced expression of MGMT. Modified nucleotides can include, for example, bicyclic nucleotide analogs, nucleotide analogs that are intercalator pseudonucleotide molecules, and peptide analogs of nucleotides with repeating N-(2-aminoethyl)-glycine units linked by peptide bonds in place of deoxyribose or ribose sugar backbones.

When the improvement is made by chemosensitization, the chemosensitization can comprise, but is not limited to, the use of dianhydrogalactitol or diacetyldianhydrogalactitol as a chemosensitizer in combination with an agent selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) vinca alkaloids;
(n) 5-fluorouracil;
(o) curcumin;
(p) NF-κB inhibitors;
(q) rosmarinic acid;
(r) mitoguazone; and
(s) tetrandrine.

When the improvement is made by chemopotentiation, the chemopotentiation can comprise, but is not limited to, the use of dianhydrogalactitol or diacetyldianhydrogalactitol as a chemopotentiator in combination with an agent selected from the group consisting of:
(a) topoisomerase inhibitors;
(b) fraudulent nucleosides;
(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) vinca alkaloids;
(n) 5-fluorouracil;
(o) curcumin;
(p) NF-κB inhibitors;
(q) rosmarinic acid;
(r) mitoguazone; and
(s) tetrandrine.

In one alternative, when the chemopotentiation involves chemopotentiation of an alkylating agent by the activity of dianhydrogalactitol or diacetyldianhydrogalactitol. the alkylating agent can be selected from the group consisting of BCNU, BCNU wafers (Gliadel), CCNU, bendamustine (Treanda), and temozolimide (Temodar).

When the improvement is made by post-treatment management, the post-treatment management can be, but is not limited to, a method selected from the group consisting of:
(a) a therapy associated with pain management;
(b) administration of an anti-emetic;
(c) an anti-nausea therapy;
(d) administration of an anti-inflammatory agent;
(e) administration of an anti-pyretic agent; and
(f) administration of an immune stimulant.

When the improvement is made by alternative medicine/post-treatment support, the alternative medicine/post-treatment support can be, but is not limited to, a method selected from the group consisting of:
(a) hypnosis;
(b) acupuncture;
(c) meditation;
(d) a herbal medication created either synthetically or through extraction; and
(e) applied kinesiology.

In one alternative, when the method is a herbal medication created either synthetically or through extraction, the herbal medication created either synthetically or through extraction can be selected from the group consisting of:
(a) a NF-κB inhibitor;
(b) a natural anti-inflammatory;

(c) an immunostimulant;
(d) an antimicrobial; and
(v) a flavonoid, isoflavone, or flavone.

When the herbal medication created either synthetically or through extraction is a NF-κB inhibitor, the NF-κB inhibitor can be selected from the group consisting of parthenolide, curcumin, and rosmarinic acid. When the herbal medication created either synthetically or through extraction is a natural anti-inflammatory, the natural anti-inflammatory can be selected from the group consisting of rhein and parthenolide. When the herbal medication created either synthetically or through extraction is an immunostimulant, the immunostimulant can be a product found in or isolated from *Echinacea*. When the herbal medication created either synthetically or through extraction is an anti-microbial, the anti-microbial can be berberine. When the herbal medication created either synthetically or through extraction is a flavonoid or flavone, the flavonoid, isoflavone, or flavone can be selected from the group consisting of apigenin, genistein, apigenenin, genistein, genistin, 6"-O-malonylgenistin, 6"-O-acetylgenistin, daidzein, daidzin, 6"-O-malonyldaidzin, 6"-O-acetylgenistin, glycitein, glycitin, 6"-O-malonylglycitin, and 6-O-acetylglycitin.

When the improvement is made by a bulk drug product improvement, the bulk drug product improvement can be, but is not limited to, a bulk drug product improvement selected from the group consisting of:
(a) salt formation;
(b) preparation as a homogeneous crystal structure;
(c) preparation as a pure isomer;
(d) increased purity;
(e) preparation with lower residual solvent content; and
(f) preparation with lower residual heavy metal content.

When the improvement is made by use of a diluent, the diluent can be, but is not limited to, a diluent selected from the group consisting of:
(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

When the improvement is made by use of a solvent system, the solvent system can be, but is not limited to, a solvent system selected from the group consisting of:
(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

When the improvement is made by use of an excipient, the excipient can be, but is not limited to, an excipient selected from the group consisting of: group consisting of:
(a) mannitol;
(b) albumin;
(c) EDTA;
(d) sodium bisulfite;
(e) benzyl alcohol;
(f) a carbonate buffer; and
(g) a phosphate buffer.

When the improvement is made by use of a dosage form, the dosage form can be, but is not limited to, a dosage form selected from the group consisting of:
(a) tablets;
(b) capsules;
(c) topical gels;
(d) topical creams;
(e) patches;
(f) suppositories; and
(g) lyophilized dosage fills.

Formulation of pharmaceutical compositions in tablets, capsules, and topical gels, topical creams or suppositories is well known in the art and is described, for example, in United States Patent Application Publication No. 2004/0023290 by Griffin et al., incorporated herein by this reference.

Formulation of pharmaceutical compositions as patches such as transdermal patches is well known in the art and is described, for example, in U.S. Pat. No. 7,728,042 to Eros et al., incorporated herein by this reference.

Lyophilized dosage fills are also well known in the art. One general method for the preparation of such lyophilized dosage fills, applicable to dianhydrogalactitol and derivatives thereof and to diacetyldianhydrogalactitol and derivatives thereof, comprises the following steps:

(1) Dissolve the drug in water for injection precooled to below 10° C. Dilute to final volume with cold water for injection to yield a 40 mg/mL solution.

(2) Filter the bulk solution through an 0.2-μm filter into a receiving container under aseptic conditions. The formulation and filtration should be completed in 1 hour.

(3) Fill nominal 1.0 mL filtered solution into sterilized glass vials in a controlled target range under aseptic conditions.

(4) After the filling, all vials are placed with rubber stoppers inserted in the "lyophilization position" and loaded in the prechilled lyophilizer. For the lyophilizer, shelf temperature is set at +5° C. and held for 1 hour; shelf temperature is then adjusted to −5° C. and held for one hour, and the condenser, set to −60° C., turned on.

(5) The vials are then frozen to 30° C. or below and held for no less than 3 hours, typically 4 hours.

(6) Vacuum is then turned on, the shelf temperature is adjusted to −5° C., and primary drying is performed for 8 hours; the shelf temperature is again adjusted to −5° C. and drying is carried out for at least 5 hours.

(7) Secondary drying is started after the condenser (set at −60° C.) and vacuum are turned on. In secondary drying, the shelf temperature is controlled at +5° C. for 1 to 3 hours, typically 1.5 hours, then at 25° C. for 1 to 3 hours, typically 1.5 hours, and finally at 35-40° C. for at least 5 hours, typically for 9 hours, or until the product is completely dried.

(8) Break the vacuum with filtered inert gas (e.g., nitrogen). Stopper the vials in the lyophilizer.

(9) Vials are removed from the lyophilizer chamber and sealed with aluminum flip-off seals. All vials are visually inspected and labeled with approved labels.

When the improvement is made by use of dosage kits and packaging, the dosage kits and packaging can be, but are not limited to, dosage kits and packaging selected from the group consisting of the use of amber vials to protect from light and the use of stoppers with specialized coatings to improve shelf-life stability.

When the improvement is made by use of a drug delivery system, the drug delivery system can be, but is not limited to, a drug delivery system selected from the group consisting of:

(a) nanocrystals;
(b) bioerodible polymers;
(c) liposomes;
(d) slow release injectable gels; and
(e) microspheres.

Nanocrystals are described in U.S. Pat. No. 7,101,576 to Hovey et al., incorporated herein by this reference.

Bioerodible polymers are described in U.S. Pat. No. 7,318,931 to Okumu et al., incorporated herein by this reference. A bioerodible polymer decomposes when placed inside an organism, as measured by a decline in the molecular weight of the polymer over time. Polymer molecular weights can be determined by a variety of methods including size exclusion chromatography (SEC), and are generally expressed as weight averages or number averages. A polymer is bioerodible if, when in phosphate buffered saline (PBS) of pH 7.4 and a temperature of 37° C., its weight-average molecular weight is reduced by at least 25% over a period of 6 months as measured by SEC. Useful bioerodible polymers include polyesters, such as poly(caprolactone), poly(glycolic acid), poly(lactic acid), and poly(hydroxybutyrate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly(alkylene oxalate); poly(alkylene succinate); polyhydroxycellulose; chitin; chitosan; and copolymers and mixtures thereof.

Liposomes are well known as drug delivery vehicles. Liposome preparation is described in European Patent Application Publication No. EP 1332755 by Weng et al., incorporated herein by this reference.

Slow release injectable gels are known in the art and are described, for example, in B. Jeong et al., "Drug Release from Biodegradable Injectable Thermosensitive Hydrogel of PEG-PLGA-PEG Triblock Copolymers," *J. Controlled Release* 63: 155-163 (2000).

The use of microspheres for drug delivery is known in the art and is described, for example, in H. Okada & H. Taguchi, "Biodegradable Microspheres in Drug Delivery," *Crit. Rev. Ther. Drug Carrier Sys.* 12: 1-99 (1995), incorporated herein by this reference.

When the improvement is made by use of a drug conjugate form, the drug conjugate form can be, but is not limited to, a drug conjugate form selected from the group consisting of:

(a) a polymer system;
(b) polylactides;
(c) polyglycolides;
(d) amino acids;
(e) peptides; and
(f) multivalent linkers.

Polylactide conjugates are well known in the art and are described, for example, in R. Tong & C. Cheng, "Controlled Synthesis of Camptothecin-Polylactide Conjugates and Nanoconjugates," *Bioconjugate Chem.* 21: 111-121 (2010), incorporated by this reference.

Polyglycolide conjugates are also well known in the art and are described, for example, in PCT Patent Application Publication No. WO 2003/070823 by Elmaleh et al., incorporated herein by this reference.

Multivalent linkers are known in the art and are described, for example, in United States Patent Application Publication No. 2007/0207952 by Silva et al., incorporated herein by this reference. For example, multivalent linkers can contain a thiophilic group for reaction with a reactive cysteine, and multiple nucleophilic groups (such as NH or OH) or electrophilic groups (such as activated esters) that permit attachment of a plurality of biologically active moieties to the linker.

Suitable reagents for cross-linking many combinations of functional groups are known in the art. For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150, incorporated herein by this reference. The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the ϵ-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the .epsilon.-amino group of the side chain of lysine. Many other electrophilic reagents are known that will react with the ϵ-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146, incorporated herein by this reference. Additionally, electrophilic reagents are known that will react with carboxylate side chains such as those of aspartate and glutamate, such as diazoalkanes and diazoacetyl compounds, carbonyldiimidazole, and carbodiimides. These are described in G. T. Hermanson, "Bioconjugate Techniques" (Academic Press, San Diego, 1996), pp. 152-154, incorporated herein by this reference. Furthermore, electrophilic reagents are known that will react with hydroxyl groups such as those in the side chains of serine and threonine, including reactive haloalkane derivatives. These are described in G. T. Hermanson, "Bioconjugate Techniques," (Academic Press, San Diego, 1996), pp. 154-158, incorporated herein by this reference. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail.

Additional combinations of reactive groups for cross-linking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, or carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996), incorporated herein by this reference.

When the improvement is made by use of a compound analog, the compound analog can be, but is not limited to, a compound analog selected from the group consisting of:
  (a) alteration of side chains to increase or decrease lipophilicity;
  (b) addition of an additional chemical functionality to alter a property selected from the group consisting of reactivity, electron affinity, and binding capacity; and
  (c) alteration of salt form.

When the improvement is made by use of a prodrug system, the prodrug system can be, but is not limited to, a prodrug system selected from the group consisting of:
  (a) the use of enzyme sensitive esters;
  (b) the use of dimers;
  (c) the use of Schiff bases;
  (d) the use of pyridoxal complexes; and
  (e) the use of caffeine complexes.

The use of prodrug systems is described in T. Jarvinen et al., "Design and Pharmaceutical Applications of Prodrugs" in *Drug Discovery Handbook* (S. C. Gad, ed., Wiley-Interscience, Hoboken, N.J., 2005), ch. 17, pp. 733-796, incorporated herein by this reference. This publication describes the use of enzyme sensitive esters as prodrugs. The use of dimers as prodrugs is described in U.S. Pat. No. 7,879,896 to Allegretti et al., incorporated herein by this reference. The use of peptides in prodrugs is described in S. Prasad et al., "Delivering Multiple Anticancer Peptides as a Single Prodrug Using Lysyl-Lysine as a Facile Linker," *J. Peptide Sci.* 13: 458-467 (2007), incorporated herein by this reference. The use of Schiff bases as prodrugs is described in U.S. Pat. No. 7,619,005 to Epstein et al., incorporated herein by this reference. The use of caffeine complexes as prodrugs is described in U.S. Pat. No. 6,443,898 to Unger et al., incorporated herein by this reference.

When the improvement is made by use of a multiple drug system, the multiple drug system can be, but is not limited to, a multiple drug system selected from the group consisting of:
  (a) use of multi-drug resistance inhibitors;
  (b) use of specific drug resistance inhibitors;
  (c) use of specific inhibitors of selective enzymes;
  (d) use of signal transduction inhibitors;
  (e) use of repair inhibition; and
  (f) use of topoisomerase inhibitors with non-overlapping side effects.

Multi-drug resistance inhibitors are described in U.S. Pat. No. 6,011,069 to Inomata et al., incorporated herein by this reference.

Specific drug resistance inhibitors are described in T. Hideshima et al., "The Proteasome Inhibitor PS-341 Inhibits Growth, Induces Apoptosis, and Overcomes Drug Resistance in Human Multiple Myeloma Cells," *Cancer Res.* 61: 3071-3076 (2001), incorporated herein by this reference.

Repair inhibition is described in N. M. Martin, "DNA Repair Inhibition and Cancer Therapy," *J. Photochem. Photobiol. B* 63: 162-170 (2001), incorporated herein by this reference.

When the improvement is made by biotherapeutic enhancement, the biotherapeutic enhancement can be performed by use in combination as sensitizers/potentiators with a therapeutic agent or technique that can be, but is not limited to, a therapeutic agent or technique selected from the group consisting of:
  (a) cytokines;
  (b) lymphokines;
  (c) therapeutic antibodies;
  (d) antisense therapies;
  (e) gene therapies;
  (f) ribozymes; and
  (g) RNA interference.

Antisense therapies are described, for example, in B. Weiss et al., "Antisense RNA Gene Therapy for Studying and Modulating Biological Processes," *Cell. Mol. Life Sci.* 55: 334-358 (1999), incorporated herein by this reference.

Ribozymes are described, for example, in S. Pascolo, "RNA-Based Therapies" in *Drug Discovery Handbook* (S. C. Gad, ed., Wiley-Interscience, Hoboken, N.J., 2005), ch. 27, pp. 1273-1278, incorporated herein by this reference.

RNA interference is described, for example, in S. Pascolo, "RNA-Based Therapies" in *Drug Discovery Handbook* (S. C. Gad, ed., Wiley-Interscience, Hoboken, N.J., 2005), ch. 27, pp. 1278-1283, incorporated herein by this reference.

When the biotherapeutic enhancement is use in combination as sensitizers/potentiators with a therapeutic antibody, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by use of biotherapeutic resistance modulation, the biotherapeutic resistance modulation can be, but is not limited to, use against tumors resistant to a therapeutic agent or technique selected from the group consisting of:
  (a) biological response modifiers;
  (b) cytokines;
  (c) lymphokines;
  (d) therapeutic antibodies;
  (e) antisense therapies;
  (f) gene therapies;
  (g) ribozymes; and
  (h) RNA interference.

When the biotherapeutic resistance modulation is use against tumors resistant to therapeutic antibodies, the therapeutic antibody can be, but is not limited to, a therapeutic antibody selected from the group consisting of bevacizumab (Avastin), rituximab (Rituxan), trastuzumab (Herceptin), and cetuximab (Erbitux).

When the improvement is made by radiation therapy enhancement, the radiation therapy enhancement can be, but is not limited to, a radiation therapy enhancement agent or technique selected from the group consisting of:

(a) hypoxic cell sensitizers;
(b) radiation sensitizers/protectors;
(c) photosensitizers;
(d) radiation repair inhibitors;
(e) thiol depleters;
(f) vaso-targeted agents;
(g) DNA repair inhibitors;
(h) radioactive seeds;
(i) radionuclides;
(j) radiolabeled antibodies; and
(k) brachytherapy.

Hypoxic cell sensitizers are described in C. C. Ling et al., "The Effect of Hypoxic Cell Sensitizers at Different Irradiation Dose Rates," *Radiation Res.* 109: 396-406 (1987), incorporated herein by this reference. Radiation sensitizers are described in T. S. Lawrence, "Radiation Sensitizers and Targeted Therapies," *Oncology* 17 (Suppl. 13) 23-28 (2003), incorporated herein by this reference. Radiation protectors are described in S. B. Vuyyuri et al., "Evaluation of D-Methionine as a Novel Oral Radiation Protector for Prevention of Mucositis," *Clin. Cancer Res.* 14: 2161-2170 (2008), incorporated herein by this reference. Photosensitizers are described in R. R. Allison & C. H. Sibata, "Oncologic Photodynamic Therapy Photosensitizers: A Clinical Review," *Photodiagnosis Photodynamic Ther.* 7: 61-75 (2010), incorporated herein by this reference. Radiation repair inhibitors and DNA repair inhibitors are described in M. Hingorani et al., "Evaluation of Repair of Radiation-Induced DNA Damage Enhances Expression from Replication-Defective Adenoviral Vectors," *Cancer Res.* 68: 9771-9778 (2008), incorporated herein by this reference. Thiol depleters are described in K. D. Held et al., "Postirradiation Sensitization of Mammalian Cells by the Thiol-Depleting Agent Dimethyl Fumarate," *Radiation Res.* 127: 75-80 (1991), incorporated herein by this reference. Vaso-targeted agents are described in A. L. Seynhaeve et al., "Tumor Necrosis Factor α Mediates Homogeneous Distribution of Liposomes in Murine Melanoma that Contributes to a Better Tumor Response," *Cancer Res.* 67: 9455-9462 (2007).

When the improvement is by use of a novel mechanism of action, the novel mechanism of action can be, but is not limited to, a novel mechanism of action that is a therapeutic interaction with a target or mechanism selected from the group consisting of:

(a) inhibitors of poly-ADP ribose polymerase;
(b) agents that affect vasculature or vasodilation;
(c) oncogenic targeted agents;
(d) signal transduction inhibitors;
(e) EGFR inhibition;
(f) protein kinase C inhibition;
(g) phospholipase C downregulation;
(h) Jun downregulation;
(i) histone genes;
(j) VEGF;
(k) ornithine decarboxylase;
(l) ubiquitin C;
(m) Jun D;
(n) v-Jun;
(o) GPCRs;
(p) protein kinase A;
(q) protein kinases other than protein kinase A;
(r) prostate specific genes;
(s) telomerase; and
(t) histone deacetylase.

EGFR inhibition is described in G. Giaccone & J. A. Rodriguez, "EGFR Inhibitors: What Have We Learned from the Treatment of Lung Cancer," *Nat. Clin. Pract. Oncol.* 11: 554-561 (2005), incorporated herein by this reference. Protein kinase C inhibition is described in N. C. Swannie & S. B. Kaye, "Protein Kinase C Inhibitors," *Curr. Oncol. Rep.* 4: 37-46 (2002), incorporated herein by this reference. Phospholipase C downregulation is described in A. M. Martelli et al., "Phosphoinositide Signaling in Nuclei of Friend Cells: Phospholipase C β Downregulation Is Related to Cell Differentiation," *Cancer Res.* 54: 2536-2540 (1994), incorporated herein by this reference. Downregulation of Jun (specifically, c-Jun) is described in A. A. P. Zada et al., "Downregulation of c-Jun Expression and Cell Cycle Regulatory Molecules in Acute Myeloid Leukemia Cells Upon CD44 Ligation," *Oncogene* 22: 2296-2308 (2003), incorporated herein by this reference. The role of histone genes as a target for therapeutic intervention is described in B. Calabretta et al., "Altered Expression of G1-Specific Genes in Human Malignant Myeloid Cells," *Proc. Natl. Acad. Sci. USA* 83: 1495-1498 (1986), incorporated herein by this reference. The role of VEGF as a target for therapeutic intervention is described in A. Zielke et al., "VEGF-Mediated Angiogenesis of Human Pheochromocytomas Is Associated to Malignancy and Inhibited by anti-VEGF Antibodies in Experimental Tumors," *Surgery* 132: 1056-1063 (2002), incorporated herein by this reference. The role of ornithine decarboxylase as a target for therapeutic intervention is described in J. A. Nilsson et al., "Targeting Ornithine Decarboxylase in Myc-Induced Lymphomagenesis Prevents Tumor Formation," *Cancer Cell* 7: 433-444 (2005), incorporated herein by this reference. The role of ubiquitin C as a target for therapeutic intervention is described in C. Aghajanian et al., "A Phase I Trial of the Novel Proteasome Inhibitor PS341 in Advanced Solid Tumor Malignancies," *Clin. Cancer Res.* 8: 2505-2511 (2002), incorporated herein by this reference. The role of Jun D as a target for therapeutic intervention is described in M. M. Caffarel et al., "JunD Is Involved in the Antiproliferative Effect of $\Delta^9$-Tetrahydrocannibinol on Human Breast Cancer Cells," *Oncogene* 27: 5033-5044 (2008), incorporated herein by this reference. The role of v-Jun as a target for therapeutic intervention is described in M. Gao et al., "Differential and Antagonistic Effects of v-Jun and c-Jun," *Cancer Res.* 56: 4229-4235 (1996), incorporated herein by this reference. The role of protein kinase A as a target for therapeutic intervention is described in P. C. Gordge et al., "Elevation of Protein Kinase A and Protein Kinase C in Malignant as Compared With Normal Breast Tissue," *Eur. J. Cancer* 12: 2120-2126 (1996), incorporated herein by this reference. The role of telomerase as a target for therapeutic intervention is described in E. K. Parkinson et al., "Telomerase as a Novel and Potentially Selective Target for Cancer Chemotherapy," *Ann. Med.* 35: 466-475 (2003), incorporated herein by this reference. The role of histone deacetylase as a target for therapeutic intervention is described in A. Melnick & J. D. Licht, "Histone Deacetylases as Therapeutic Targets in Hematologic Malignancies," *Curr. Opin. Hematol.* 9: 322-332 (2002), incorporated herein by this reference.

When the improvement is made by use of selective target cell population therapeutics, the use of selective target cell population therapeutics can be, but is not limited to, a use selected from the group consisting of:

(a) use against radiation sensitive cells;
(b) use against radiation resistant cells;
(c) use against energy depleted cells; and
(d) use against endothelial cells.

As described above, the present invention also encompasses methods and compositions to improve the efficacy and/or reduce the side effects of suboptimally administered drug therapy of additional therapeutic agents, including, but not limited to, Avastin (bevacizumab), Rituxan (rituximab), Nexavar (sorafenib), dasatinib, nilotinib, Provenge (sipuleucel-T), Tarceva (erlotinib), and Iressa (gefitinib).

Avastin (bevacizumab) has a number of side effects associated with interference with angiogenesis, including hypertension and increased risk of bleeding. This suggests possible use with antihypertensives, administration of platelets, or agents to improve wound healing.

Rituxan (rituximab) has side effects that include cardiac arrest, infections, including viral infections and hepatitis B reactivation, progressive multifocal encephalopathy, and tumor lysis syndrome. This suggests possible use with anti-virals, antibiotics, probenecid (to treat hyperuricemia).

Nexavar (sorafenib) has side effects that include skin rash, skin reactions, diarrhea, and hypertension. This suggests possible use with antihypertensives or anti-inflammatory agents.

Dasatinib has side effects that include neutropenia, myelosuppression, pleural effusions, headache, diarrhea, and peripheral edema. This suggests possible use with anti-inflammatory agents or agents that promote immune function. Dasatinib has the property that patients with the T315L mutation in BCR/ABL show resistance to dasatinib. This suggests genotypic analysis of patients to whom dasatinib might be administered.

Nilotinib has side effects that include possible heart complications. Nilotinib also has the property that patients with the T315L mutation in BCR/ABL show resistance to nilotinib. This suggests genotypic analysis of patients to whom nilotinib might be administered.

Provenge (sipuleucel-T) has side effects that include chills, fever, fatigue, nausea, headache, and rare cardiovascular events. This suggests possible use with anti-inflammatory agents, anti-nausea agents, and anti-emetics.

Tarceva (erlotinib) has side effects that include rash, diarrhea, loss of appetite, fatigue, and interstitial pneumonitis. This suggests possible use with anti-inflammatory agents and anti-diarrhea agents. Tarceva only works with patients that have an EGFR mutation, which suggests genotypic analysis of patents to whom Tarceva might be administered. Additionally, Tarceva has been found to be a potent inhibitor of the JAK2V617F mutant of the JAK2 tyrosine kinase, and this mutation has been found to exist in most patients with polycythemia vera and many patients with other myeloproliferative disorders, including idiopathic myelofibrosis and essential thrombocythemia.

Iressa (gefitinib) is also an EGFR inhibitor, and thus its mechanism of action is similar to Tarceva. Similarly, this works with patients that have an EGFR mutation. This drug is particularly used in some types of non-small-cell lung cancer, including adenocarcinoma. Side effects include acne, diarrhea, nausea, vomiting, anorexia, stomatitis, interstitial lung disease, and other effects. Again, this suggests use with anti-inflammatory agents, anti-diarrhea agents, and anti-emetics.

Another aspect of the present invention is a composition to improve the efficacy and/or reduce the side effects of suboptimally administered drug therapy comprising an alternative selected from the group consisting of:
(i) a therapeutically effective quantity of a modified therapeutic agent or a derivative, analog, or prodrug of a therapeutic agent or modified therapeutic agent, wherein the modified therapeutic agent or the derivative, analog or prodrug of the therapeutic agent or modified therapeutic agent possesses increased therapeutic efficacy or reduced side effects as compared with an unmodified therapeutic agent;
(ii) a composition comprising:
 (a) a therapeutically effective quantity of a therapeutic agent, a modified therapeutic agent or a derivative, analog, or prodrug of a therapeutic agent or modified therapeutic agent; and
 (b) at least one additional therapeutic agent, therapeutic agent subject to chemosensitization, therapeutic agent subject to chemopotentiation, diluent, excipient, solvent system, or drug delivery system, wherein the composition possesses increased therapeutic efficacy or reduced side effects as compared with an unmodified therapeutic agent;
(iii) a therapeutically effective quantity of a therapeutic agent, a modified therapeutic agent, or a derivative, analog, or prodrug of a therapeutic agent or modified therapeutic agent that is incorporated into a dosage form, wherein the therapeutic agent, the modified therapeutic agent, or the derivative, analog, or prodrug of a therapeutic agent or modified therapeutic agent incorporated into the dosage form possesses increased therapeutic efficacy or reduced side effects as compared with an unmodified therapeutic agent;
(iv) a therapeutically effective quantity of a therapeutic agent, a modified therapeutic agent, or a derivative, analog, or prodrug of a therapeutic agent or modified therapeutic agent that is incorporated into a dosage kit and packaging, wherein the therapeutic agent, the modified therapeutic agent, or the derivative, analog, or prodrug of a therapeutic agent or modified therapeutic agent incorporated into the dosage kit and packaging possesses increased therapeutic efficacy or reduced side effects as compared with an unmodified therapeutic agent; and
(v) a therapeutically effective quantity of a therapeutic agent, a modified therapeutic agent, or a derivative, analog, or prodrug of a therapeutic agent or modified therapeutic agent that is subjected to a bulk drug product improvement, wherein the therapeutic agent, the modified therapeutic agent, or the derivative, analog, or prodrug of a therapeutic agent or modified therapeutic agent subject to the bulk drug product improvement possesses increased therapeutic efficacy or reduced side effects as compared with an unmodified therapeutic agent.

Typically, the composition possesses increased efficacy or reduced side effects for cancer therapy. Typically, the unmodified therapeutic agent is dianhydrogalactitol or diacetyldianhydrogalactitol, as described above. Alternatively, the unmodified therapeutic agent can be selected from the group consisting of Avastin (bevacizumab), Rituxan (rituximab), Nexavar (sorafenib), dasatinib, nilotinib, Provenge (sipuleucel-T), Tarceva (erlotinib), and Iressa (gefitinib).

In one alternative, the composition comprises a drug combination comprising:
(i) dianhydrogalactitol; and
(ii) an additional therapeutic agent selected from the group consisting of:
 (a) topoisomerase inhibitors;
 (b) fraudulent nucleosides;
 (c) fraudulent nucleotides;
 (d) thymidylate synthetase inhibitors;
 (e) signal transduction inhibitors;

(f) cisplatin or platinum analogs;
(g) alkylating agents;
(h) anti-tubulin agents;
(i) antimetabolites;
(j) berberine;
(k) apigenin;
(l) amonafide;
(m) vinca alkaloids;
(n) 5-fluorouracil;
(o) curcumin;
(p) NF-κB inhibitors;
(q) rosmarinic acid;
(r) mitoguazone;
(s) tetrandrine; and
(t) an inhibitor of mutant isocitrate dehydrogenase (IDH);
(u) a MGMT inhibitor; and
(v) an agent that inhibits NF-κB-enhanced expression of MGMT.

In another alternative of a composition according to the present invention, the composition can comprise a drug combination comprising:
(i) diacetyldianhydrogalactitol; and
(ii) an additional therapeutic agent selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin or platinum analogs;
  (g) alkylating agents;
  (h) anti-tubulin agents;
  (i) antimetabolites;
  (j) berberine;
  (k) apigenin;
  (l) amonafide;
  (m) vinca alkaloids;
  (n) 5-fluorouracil;
  (o) curcumin;
  (p) NF-κB inhibitors;
  (q) rosmarinic acid;
  (r) mitoguazone;
  (s) tetrandrine;
  (t) an inhibitor of mutant isocitrate dehydrogenase (IDH);
  (u) a MGMT inhibitor; and
  (v) an agent that inhibits NF-κB-enhanced expression of MGMT.

In these alternatives, when the additional therapeutic agent is an alkylating agent, the alkylating agent can be, but is not limited to, an alkylating agent selected from the group consisting of BCNU, BCNU wafers, CCNU, bendamustine (Treanda), and temozolomide (Temodar).

In another alternative, the composition comprises:
(i) dianhydrogalactitol; and
(ii) a therapeutic agent subject to chemosensitization selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin or platinum analogs;
  (g) alkylating agents;
  (h) anti-tubulin agents;
  (i) antimetabolites;
  (j) berberine;
  (k) apigenin;
  (l) amonafide;
  (m) vinca alkaloids;
  (n) 5-fluorouracil;
  (o) curcumin;
  (p) NF-κB inhibitors;
  (q) rosmarinic acid;
  (r) mitoguazone; and
  (s) tetrandrine;
wherein the dianhydrogalactitol acts as a chemosensitizer.

In yet another alternative, the composition can comprise:
(i) diacetyldianhydrogalactitol; and
(ii) a therapeutic agent subject to chemosensitization selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin or platinum analogs;
  (g) alkylating agents;
  (h) anti-tubulin agents;
  (i) antimetabolites;
  (j) berberine;
  (k) apigenin;
  (l) amonafide;
  (m) vinca alkaloids;
  (n) 5-fluorouracil;
  (o) curcumin;
  (p) NF-κB inhibitors;
  (q) rosmarinic acid;
  (r) mitoguazone; and
  (s) tetrandrine;
wherein the diacetyldianhydrogalactitol acts as a chemosensitizer.

In still another alternative, the composition comprises:
(i) dianhydrogalactitol; and
(ii) a therapeutic agent subject to chemopotentiation selected from the group consisting of:
  (a) topoisomerase inhibitors;
  (b) fraudulent nucleosides;
  (c) fraudulent nucleotides;
  (d) thymidylate synthetase inhibitors;
  (e) signal transduction inhibitors;
  (f) cisplatin or platinum analogs;
  (g) alkylating agents;
  (h) anti-tubulin agents;
  (i) antimetabolites;
  (j) berberine;
  (k) apigenin;
  (l) amonafide;
  (m) vinca alkaloids;
  (n) 5-fluorouracil;
  (o) curcumin;
  (p) NF-κB inhibitors;
  (q) rosmarinic acid;
  (r) mitoguazone;
  (s) tetrandrine; and
  (t) biotherapeutics;
wherein the dianhydrogalactitol acts as a chemopotentiator.

In yet another alternative, the composition comprises:
(i) diacetyldianhydrogalactitol; and
(ii) a therapeutic agent subject to chemopotentiation selected from the group consisting of:
  (a) topoisomerase inhibitors;
  (b) fraudulent nucleosides;

(c) fraudulent nucleotides;
(d) thymidylate synthetase inhibitors;
(e) signal transduction inhibitors;
(f) cisplatin or platinum analogs;
(g) alkylating agents;
(h) anti-tubulin agents;
(i) antimetabolites;
(j) berberine;
(k) apigenin;
(l) amonafide;
(m) vinca alkaloids;
(n) 5-fluorouracil;
(o) curcumin;
(p) NF-κB inhibitors;
(q) rosmarinic acid;
(r) mitoguazone;
(s) tetrandrine; and
(t) biotherapeutics;
wherein the diacetyldianhydrogalactitol acts as a chemopotentiator.

In these alternatives, wherein the additional therapeutic agent is a biotherapeutic, the biotherapeutic can be, but is not limited to, a biotherapeutic selected from the group consisting of Avastin, Herceptin, Rituxan, and Erbitux.

In yet another alternative, the therapeutic agent is dianhydrogalactitol or diacetyldianhydrogalactitol and the dianhydrogalactitol or diacetyldianhydrogalactitol is subjected to a bulk drug product improvement, wherein the bulk drug product improvement is selected from the group consisting of:
(a) salt formation;
(b) preparation as a homogeneous crystal structure;
(c) preparation as a pure isomer;
(d) increased purity;
(e) preparation with lower residual solvent content; and
(f) preparation with lower residual heavy metal content.

In still another alternative, the therapeutic agent is dianhydrogalactitol or diacetyldianhydrogalactitol and the composition comprises a diluent, wherein the diluent is selected from the group consisting of:
(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

In still another alternative, the therapeutic agent is dianhydrogalactitol or diacetyldianhydrogalactitol and the composition comprises a solvent system, wherein the solvent system is selected from the group consisting of:
(a) an emulsion;
(b) dimethylsulfoxide (DMSO);
(c) N-methylformamide (NMF)
(d) DMF;
(e) ethanol;
(f) benzyl alcohol;
(g) dextrose-containing water for injection;
(h) Cremophor;
(i) cyclodextrin; and
(j) PEG.

In yet another alternative, the therapeutic agent is dianhydrogalactitol or diacetyldianhydrogalactitol and the composition comprises an excipient, wherein the excipient is selected from the group consisting of:
(a) mannitol;
(b) albumin;
(c) EDTA;
(d) sodium bisulfite;
(e) benzyl alcohol;
(f) a carbonate buffer; and
(g) a phosphate buffer.

In still another alternative, the therapeutic agent is dianhydrogalactitol or diacetyldianhydrogalactitol and the dianhydrogalactitol or diacetyldianhydrogalactitol is incorporated into a dosage form selected from the group consisting of:
(a) tablets;
(b) capsules;
(c) topical gels;
(d) topical creams;
(e) patches;
(f) suppositories; and
(g) lyophilized dosage fills.

In yet another alternative, the therapeutic agent is dianhydrogalactitol or diacetyldianhydrogalactitol and the dianhydrogalactitol or diacetyldianhydrogalactitol is incorporated into a dosage kit and packaging selected from the group consisting of amber vials to protect from light and stoppers with specialized coatings to improve shelf-life stability.

In still another alternative, the therapeutic agent is dianhydrogalactitol or diacetyldianhydrogalactitol and the composition comprises a drug delivery system selected from the group consisting of:
(a) nanocrystals;
(b) bioerodible polymers;
(c) liposomes;
(d) slow release injectable gels; and
(e) microspheres.

In still another alternative, the therapeutic agent is dianhydrogalactitol or diacetyldianhydrogalactitol and the dianhydrogalactitol or diacetyldianhydrogalactitol is present in the composition in a drug conjugate form selected from the group consisting of:
(a) a polymer system;
(b) polylactides;
(c) polyglycolides;
(d) amino acids;
(e) peptides; and
(f) multivalent linkers.

In yet another alternative, the therapeutic agent is a modified dianhydrogalactitol or a modified diacetyldianhydrogalactitol and the modification is selected from the group consisting of:
(a) alteration of side chains to increase or decrease lipophilicity;
(b) addition of an additional chemical functionality to alter a property selected from the group consisting of reactivity, electron affinity, and binding capacity; and
(c) alteration of salt form.

In still another alternative, the therapeutic agent is dianhydrogalactitol or diacetyldianhydrogalactitol and the dianhydrogalactitol or diacetyldianhydrogalactitol is in the form of a prodrug system, wherein the prodrug system is selected from the group consisting of:
(a) the use of enzyme sensitive esters;
(b) the use of dimers;

(c) the use of Schiff bases;
(d) the use of pyridoxal complexes; and
(e) the use of caffeine complexes.

In yet another alternative, the therapeutic agent is dianhydrogalactitol or diacetyldianhydrogalactitol and the composition further comprises at least one additional therapeutic agent to form a multiple drug system, wherein the at least one additional therapeutic agent is selected from the group consisting of:
(a) an inhibitor of multi-drug resistance;
(b) a specific drug resistance inhibitor;
(c) a specific inhibitor of a selective enzyme;
(d) a signal transduction inhibitor;
(e) an inhibitor of a repair enzyme; and
(f) a topoisomerase inhibitor with non-overlapping side effects.

When a pharmaceutical composition according to the present invention includes a prodrug, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

When the pharmacologically active compound in a pharmaceutical composition according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, β-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

The amount of a given pharmacologically active agent that is included in a unit dose of a pharmaceutical composition according to the present invention will vary depending upon factors such as the particular compound, disease condition and its severity, the identity (e.g., weight) of the subject in need of treatment, but can nevertheless be routinely determined by one skilled in the art. Typically, such pharmaceutical compositions include a therapeutically effective quantity of the pharmacologically active agent and an inert pharmaceutically acceptable carrier or diluent. Typically, these compositions are prepared in unit dosage form appropriate for the chosen route of administration, such as oral administration or parenteral administration. A pharmacologically active agent as described above can be administered in conventional dosage form prepared by combining a therapeutically effective amount of such a pharmacologically active agent as an active ingredient with appropriate pharmaceutical carriers or diluents according to conventional procedures. These procedures may involve mixing, granulating and compressing or dissolving the ingredients as appropriate to the desired preparation. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a pharmacologically active agent as described above is dissolved in an aqueous solution of an organic or inorganic acid, such as 0.3 M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0-60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease and/or condition being treated. Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular therapeutic agent, the route of administration, the time of administration, the rate of excretion of the particular compound being employed, the severity of the condition, other health considerations affecting the subject, and the status of liver and kidney function of the subject. It also depends on the duration of the treatment, other drugs, compounds and/or materials used in combination with the particular therapeutic agent employed, as well as the age, weight, condition, general health and prior medical history of the subject being treated, and like factors. Methods for determining optimal dosages are described in the art, e.g., Remington: *The Science and Practice of Pharmacy*, Mack Publishing Co., 20$^{th}$ ed., 2000. Optimal dosages for a given set of conditions can be ascertained by those skilled in the art using conventional dosage-determination tests in view of the experimental data for an agent. For oral administration, an exemplary daily dose generally employed is from about 0.001 to about 3000 mg/kg of body weight, with courses of treatment repeated at appropriate intervals. In some embodiments, the daily dose is from about 1 to 3000 mg/kg of body weight.

Typical daily doses in a patient may be anywhere between about 500 mg to about 3000 mg, given once or twice daily, e.g., 3000 mg can be given twice daily for a total dose of 6000 mg. In one embodiment, the dose is between about 1000 to about 3000 mg. In another embodiment, the dose is between about 1500 to about 2800 mg. In other embodiments, the dose is between about 2000 to about 3000 mg.

Plasma concentrations in the subjects may be between about 100 µM to about 1000 µM. In some embodiments, the plasma concentration may be between about 200 µM to about 800 µM. In other embodiments, the concentration is about 300 µM to about 600 µM. In still other embodiments the plasma concentration may be between about 400 to about 800 µM. Administration of prodrugs is typically dosed at weight levels which are chemically equivalent to the weight levels of the fully active form.

The compositions of the invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, solutions, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Pharmaceutical formulations for parenteral administration can include aqueous solutions or suspensions. Suitable lipophilic solvents or vehicles include fatty oils such as sesame oil or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or modulators which increase the solubility or dispersibility of the composition to allow for the preparation of highly concentrated solutions, or can contain suspending or dispersing agents. Pharmaceutical preparations for oral use can be obtained by combining the pharmacologically active agent with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating modulators may be added, such as the cross-linked polyvinyl pyrrolidone, agar, or alginic acid or a salt thereof such as sodium alginate.

Other ingredients such as stabilizers, for example, antioxidants such as sodium citrate, ascorbyl palmitate, propyl gallate, reducing agents, ascorbic acid, vitamin E, sodium bisulfite, butylated hydroxytoluene, BHA, acetylcysteine, monothioglycerol, phenyl-α-naphthylamine, or lecithin can be used. Also, chelators such as EDTA can be used. Other ingredients that are conventional in the area of pharmaceutical compositions and formulations, such as lubricants in tablets or pills, coloring agents, or flavoring agents, can be used. Also, conventional pharmaceutical excipients or carriers can be used. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agents, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, particularly as described above. For administration of any of the compounds used in the present invention, preparations should meet sterility, pyrogenicity, general safety, and purity standards as required by the FDA Office of Biologics Standards or by other regulatory organizations regulating drugs.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

A pharmaceutical composition can be administered by a variety of methods known in the art. The routes and/or modes of administration vary depending upon the desired results. Depending on the route of administration, the pharmacologically active agent may be coated in a material to protect the targeting composition or other therapeutic agent from the action of acids and other compounds that may inactivate the agent. Conventional pharmaceutical practice can be employed to provide suitable formulations or compositions for the administration of such pharmaceutical compositions to subjects. Any appropriate route of administration can be employed, for example, but not limited to, intravenous, parenteral, intraperitoneal, intravenous, transcutaneous, subcutaneous, intramuscular, intraurethral, or oral administration. Depending on the severity of the malignancy or other disease, disorder, or condition to be treated, as well as other conditions affecting the subject to be treated, either systemic or localized delivery of the pharmaceutical composition can be used in the course of treatment. The pharmaceutical composition as described above can be administered together with additional therapeutic agents intended to treat a particular disease or condition, which may be the same disease or condition that the pharmaceutical composition is intended to treat, which may be a related disease or condition, or which even may be an unrelated disease or condition.

Pharmaceutical compositions according to the present invention can be prepared in accordance with methods well known and routinely practiced in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymers, lactide/glycolide copolymers, or polyoxyethylene-polyoxypropylene copolymers may be used to control the release of the compounds. Other potentially useful parenteral delivery systems for molecules of the invention include ethylene-vinyl acetate copolymer particles, osmotic pumps, and implantable infusion systems. Formulations for inhalation may contain excipients, for example, lactose, or may be aqueous solutions containing, e.g., polyoxyethylene-9-lauryl ether, glycocholate and deoxycholate, or can be oily solutions for administration or gels.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

For the purposes of the present application, treatment can be monitored by observing one or more of the improving symptoms associated with the disease, disorder, or condition being treated, or by observing one or more of the improving clinical parameters associated with the disease, disorder, or condition being treated, as described above.

Sustained-release formulations or controlled-release formulations are well-known in the art. For example, the sustained-release or controlled-release formulation can be (1) an oral matrix sustained-release or controlled-release formulation; (2) an oral multilayered sustained-release or controlled-release tablet formulation; (3) an oral multiparticulate sustained-release or controlled-release formulation; (4) an oral osmotic sustained-release or controlled-release formulation; (5) an oral chewable sustained-release or controlled-release formulation; or (6) a dermal sustained-release or controlled-release patch formulation.

The pharmacokinetic principles of controlled drug delivery are described, for example, in B. M. Silber et al., "Pharmacokinetic/Pharmacodynamic Basis of Controlled Drug Delivery" in *Controlled Drug Delivery: Fundamentals and Applications* (J. R. Robinson & V. H. L. Lee, eds, 2d ed., Marcel Dekker, New York, 1987), ch. 5, pp. 213-251, incorporated herein by this reference.

One of ordinary skill in the art can readily prepare formulations for controlled release or sustained release comprising a pharmacologically active agent according to the present invention by modifying the formulations described above, such as according to principles disclosed in V. H. K. Li et al, "Influence of Drug Properties and Routes of Drug Administration on the Design of Sustained and Controlled Release Systems" in *Controlled Drug Delivery: Fundamentals and Applications* (J. R. Robinson & V. H. L. Lee, eds, 2d ed., Marcel Dekker, New York, 1987), ch. 1, pp. 3-94, incorporated herein by this reference. This process of preparation typically takes into account physicochemical properties of the pharmacologically active agent, such as aqueous solubility, partition coefficient, molecular size, stability, and nonspecific binding to proteins and other biological macromolecules. This process of preparation also takes into account biological factors, such as absorption, distribution, metabolism, duration of action, the possible existence of side effects, and margin of safety, for the pharmacologically active agent. Accordingly, one of ordinary skill in the art could modify the formulations into a formulation having the desirable properties described above for a particular application.

U.S. Pat. No. 6,573,292 by Nardella, U.S. Pat. No. 6,921,722 by Nardella, U.S. Pat. No. 7,314,886 to Chao et al., and U.S. Pat. No. 7,446,122 by Chao et al., which disclose methods of use of various pharmacologically active agents and pharmaceutical compositions in treating a number of diseases and conditions, including cancer, and methods of determining the therapeutic effectiveness of such pharmacologically active agents and pharmaceutical compositions, are all incorporated herein by this reference.

ADVANTAGES OF THE INVENTION

The present invention provides more effective and efficient methods of using therapeutic drugs that have previously been evaluated for treatment of a number of diseases and conditions, especially hyperproliferative disorders, but whose evaluations resulted in a premature conclusion of lack of sufficient efficacy or of occurrence of side effects sufficient to prevent the use of the therapeutic drug. Such more effective and efficient methods of therapeutic drugs will improve efficacy, prevent or reduce the occurrence of significant side effects, and will identify categories of patients and situations in which such drugs can be effectively employed. These therapeutic drugs include, but are not limited to, dianhydrogalactitol and diacetyldianhydrogalactitol.

Methods according to the present invention possess industrial applicability for the preparation of a medicament for the treatment of a number of diseases and conditions, especially hyperproliferative diseases, and compositions according to the present invention possess industrial applicability as pharmaceutical compositions.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A composition to improve the efficacy and/or reduce the side effects of suboptimally administered drug therapy, wherein the composition possesses increased efficacy or reduced side effects for cancer therapy, wherein the composition comprises a drug combination comprising:
   (a) dianhydrogalactitol or diacetyldianhydrogalactitol; and
   (b) an additional therapeutic agent selected from the group consisting of:
      (i) topoisomerase inhibitors;
      (ii) fraudulent nucleosides;
      (iii) fraudulent nucleotides;
      (iv) thymidylate synthetase inhibitors;
      (v) signal transduction inhibitors;
      (vi) cisplatin or platinum analogs;
      (vii) alkylating agents;
      (viii) anti-tubulin agents;
      (ix) antimetabolites;
      (x) berberine;
      (xi) apigenin;
      (xii) amonafide;
      (xiii) vinca alkaloids;
      (xiv) 5-fluorouracil;
      (xv) curcumin;
      (xvi) NF-κB inhibitors;
      (xvii) rosmarinic acid;
      (xviii) mitoguazone; and
      (xix) tetrandrine.

2. A composition to improve the efficacy and/or reduce the side effects of suboptimally administered drug therapy, wherein the composition possesses increased efficacy or reduced side effects for cancer therapy, wherein the composition comprises:
   (a) dianhydrogalactitol or diacetyldianhydrogalactitol; and
   (b) a therapeutic agent subject to chemosensitization selected from the group consisting of:
      (i) topoisomerase inhibitors;
      (ii) fraudulent nucleosides;
      (iii) fraudulent nucleotides;
      (iv) thymidylate synthetase inhibitors;
      (v) signal transduction inhibitors;
      (vi) cisplatin or platinum analogs;
      (vii) alkylating agents;
      (viii) anti-tubulin agents;
      (ix) antimetabolites;
      (x) berberine;
      (xi) apigenin;
      (xii) amonafide;
      (xiii) vinca alkaloids;
      (xiv) 5-fluorouracil;
      (xv) curcumin;
      (xvi) NF-κB inhibitors;
      (xvii) rosmarinic acid;
      (xviii) mitoguazone; and
      (xix) tetrandrine;
   wherein the dianhydrogalactitol or diacetyldianhydrogalactitol acts as a chemosensitizer.

3. A composition to improve the efficacy and/or reduce the side effects of suboptimally administered drug therapy, wherein the composition possesses increased efficacy or reduced side effects for cancer therapy, wherein the composition comprises:
   (a) dianhydrogalactitol or di acetyl dianhydrogalactitol; and
   (b) a therapeutic agent subject to chemopotentiation selected from the group consisting of:
      (i) topoisomerase inhibitors;
      (ii) fraudulent nucleosides;
      (iii) fraudulent nucleotides;
      (iv) thymidylate synthetase inhibitors;
      (v) signal transduction inhibitors;
      (vi) cisplatin or platinum analogs;
      (vii) alkylating agents;
      (viii) anti-tubulin agents;
      (ix) antimetabolites;
      (x) berberine;
      (xi) apigenin;

(xii) amonafide;
(xiii) vinca alkaloids;
(xiv) 5-fluorouracil;
(xv) curcumin;
(xvi) NF-κB inhibitors;
(xvii) rosmarinic acid;
(xviii) mitoguazone;
(xix) tetrandrine; and
(xx) biotherapeutics;

wherein the dianhydrogalactitol or diacetyldianhydrogalactitol acts as a chemopotentiator.

4. A composition to improve the efficacy and/or reduce the side effects of suboptimally administered drug therapy, wherein the composition possesses increased efficacy or reduced side effects for cancer therapy, wherein the composition comprises a therapeutic agent that is dianhydrogalactitol or diacetyldianhydrogalactitol and the composition also comprises a diluent, wherein the diluent is selected from the group consisting of:
(i) an emulsion;
(ii) N-methylformamide (NMF);
(iii) DMF;
(iv) ethanol;
(v) benzyl alcohol;
(vi) dextrose-containing water for injection;
(vii) Cremophor;
(viii) cyclodextrin; and
(ix) PEG.

5. A composition to improve the efficacy and/or reduce the side effects of suboptimally administered drug therapy, wherein the composition possesses increased efficacy or reduced side effects for cancer therapy, wherein the composition comprises a therapeutic agent that is dianhydrogalactitol or diacetyldianhydrogalactitol and the composition also comprises a solvent system, wherein the solvent system is selected from the group consisting of:
(i) an emulsion;
(ii) N-methylformamide (NMF);
(iii) DMF;
(iv) ethanol;
(v) benzyl alcohol;
(vi) dextrose-containing water for injection;
(vii) Cremophor;
(viii) cyclodextrin; and
(ix) PEG.

6. A composition to improve the efficacy and/or reduce the side effects of suboptimally administered drug therapy, wherein the composition possesses increased efficacy or reduced side effects for cancer therapy, wherein the composition comprises a therapeutic agent that is dianhydrogalactitol or diacetyldianhydrogalactitol and the composition also comprises an excipient, wherein the excipient is selected from the group consisting of:
(i) mannitol;
(ii) albumin;
(iii) EDTA;
(iv) sodium bisulfite;
(v) benzyl alcohol;
(vi) a carbonate buffer; and
(vii) a phosphate buffer.

7. A composition to improve the efficacy and/or reduce the side effects of suboptimally administered drug therapy, wherein the composition possesses increased efficacy or reduced side effects for cancer therapy, wherein the composition comprises a therapeutic agent that is dianhydrogalactitol or diacetyldianhydrogalactitol and wherein the dianhydrogalactitol or diacetyldianhydrogalactitol is incorporated into a dosage form selected from the group consisting of:
(i) tablets;
(ii) capsules;
(iii) topical gels;
(iv) topical creams;
(v) patches;
(vi) suppositories; and
(vii) lyophilized dosage fills.

8. A composition to improve the efficacy and/or reduce the side effects of suboptimally administered drug therapy, wherein the composition possesses increased efficacy or reduced side effects for cancer therapy, wherein the composition comprises a therapeutic agent that is dianhydrogalactitol or diacetyldianhydrogalactitol and the composition also comprises a drug delivery system selected from the group consisting of:
(i) nanocrystals;
(ii) bioerodible polymers;
(iii) liposomes;
(iv) slow release injectable gels; and
(v) microspheres.

9. A composition to improve the efficacy and/or reduce the side effects of suboptimally administered drug therapy, wherein the composition possesses increased efficacy or reduced side effects for cancer therapy, wherein the composition comprises a therapeutic agent that is dianhydrogalactitol or diacetyldianhydrogalactitol and the dianhydrogalactitol or diacetyldianhydrogalactitol is present in the composition in a drug conjugate form selected from the group consisting of:
(i) a polymer system;
(ii) polylactides;
(iii) polyglycolides;
(iv) amino acids;
(v) peptides; and
(vi) multivalent linkers.

10. A composition to improve the efficacy and/or reduce the side effects of suboptimally administered drug therapy, wherein the composition possesses increased efficacy or reduced side effects for cancer therapy, wherein the composition comprises a therapeutic agent that is dianhydrogalactitol or diacetyldianhydrogalactitol and the dianhydrogalactitol or diacetyldianhydrogalactitol is in the form of a prodrug system, wherein the prodrug system is selected from the group consisting of:
(i) the use of enzyme sensitive esters;
(ii) the use of dimers;
(iii) the use of Schiff bases;
(iv) the use of pyridoxal complexes; and
(v) the use of caffeine complexes.

\* \* \* \* \*